United States Patent
Griffith et al.

(10) Patent No.: US 11,560,400 B2
(45) Date of Patent: Jan. 24, 2023

(54) SALTS OF DIPHOSPHATE PHOSPHORAMIDATE OF NUCLEOSIDES AS ANTICANCER COMPOUNDS

(71) Applicant: NuCana plc, Edinburgh (GB)

(72) Inventors: Hugh Griffith, Edinburgh (GB); Michaela Serpi, Cardiff South Glamorgan (GB); Fabrizio Pertusati, Cardiff South Glamorgan (GB); Magdalena Slusarczyk, Cardiff South Glamorgan (GB)

(73) Assignee: NuCana plc, Edinburgh (GB)

( * ) Notice: Subject to any disclaimer, the term of this patent is extended or adjusted under 35 U.S.C. 154(b) by 161 days.

(21) Appl. No.: 16/769,635

(22) PCT Filed: Dec. 5, 2018

(86) PCT No.: PCT/GB2018/053525
§ 371 (c)(1),
(2) Date: Jun. 4, 2020

(87) PCT Pub. No.: WO2019/110991
PCT Pub. Date: Jun. 13, 2019

(65) Prior Publication Data
US 2021/0171566 A1 Jun. 10, 2021

(30) Foreign Application Priority Data
Dec. 5, 2017 (GB) ..................... 1720279

(51) Int. Cl.
*C07H 19/207* (2006.01)
*A61P 35/02* (2006.01)
*C07H 19/10* (2006.01)

(52) U.S. Cl.
CPC ............ *C07H 19/207* (2013.01); *A61P 35/02* (2018.01); *C07H 19/10* (2013.01)

(58) Field of Classification Search
None
See application file for complete search history.

(56) References Cited

U.S. PATENT DOCUMENTS

| | | |
|---|---|---|
| 8,263,575 B2 | 9/2012 | McGuigan et al. |
| 8,933,053 B2 | 1/2015 | McGuigan et al. |
| 9,221,866 B2 | 12/2015 | McGuigan et al. |
| 9,321,798 B2 | 4/2016 | McGuigan |
| 9,655,915 B2 | 5/2017 | McGuigan et al. |
| 10,022,390 B2 | 7/2018 | McGuigan et al. |
| RE47,589 E | 9/2019 | McGuigan |
| 10,570,168 B2 | 2/2020 | Griffith et al. |
| 10,906,929 B2 | 2/2021 | Griffith et al. |
| 10,993,957 B2 | 5/2021 | McGuigan et al. |
| 2019/0375778 A1 | 12/2019 | Griffith et al. |
| 2020/0181189 A1 | 6/2020 | Griffith |
| 2021/0130387 A1 | 5/2021 | Griffith et al. |

FOREIGN PATENT DOCUMENTS

| | | | |
|---|---|---|---|
| CN | 105646629 | 6/2016 | |
| WO | WO-2005/012327 A2 | 2/2005 | |
| WO | WO-2006/100439 A1 | 9/2006 | |
| WO | WO-2010/135520 A1 | 11/2010 | |
| WO | WO-2012/117246 A1 | 9/2012 | |
| WO | WO-2014/124430 A1 | 8/2014 | |
| WO | WO-2014124430 A1 * | 8/2014 | ......... A61K 31/7068 |
| WO | WO 2015/038596 A1 | 3/2015 | |
| WO | WO-2016/083830 A1 | 6/2016 | |
| WO | WO-2016/099982 A2 | 6/2016 | |
| WO | WO-2016/106050 A1 | 6/2016 | |
| WO | WO-2017/106710 A1 | 6/2017 | |
| WO | WO-2017/155923 A1 | 9/2017 | |

OTHER PUBLICATIONS

International Search Report and Written Opinion for International Application No. PCT/GB2018/053525 dated Mar. 28, 2019.
Jessen et al., "Bioreversible Protection of Nucleoside Diphosphates," Angewandte Chemie International Edition, 47(45):8719-8722 (2008).
Pradere et al., "Synthesis of Nucleoside Phosphate and Phosphonate Prodrugs," Chemical Reviews, 114(18):9154-9218 (2014).
Shelton et al., "Metabolism, Biochemical Actions, and Chemical Synthesis of Anticancer Nucleosides, Nucleotides, and Base Analogs," Chem. Rev., 116(23):14379-14455 (2016).
United Kingdom Search Report for Application No. GB1720279.7 dated Aug. 14, 2018.
U.S. Appl. No. 17/223,241, McGuigan et al., filed Apr. 6, 2021.
U.S. Appl. No. 17/492,301, Griffith et al., filed Oct. 1, 2021.

* cited by examiner

*Primary Examiner* — Layla D Berry
(74) *Attorney, Agent, or Firm* — Knowles Intellectual Property Strategies, LLC

(57) ABSTRACT

The present invention relates to compounds comprising a salt of a diphosphate phosphoramidate of a nucleoside drug, e.g. clofarabine. The compounds are useful in the treatment of cancer, e.g. leukemia.

27 Claims, 5 Drawing Sheets

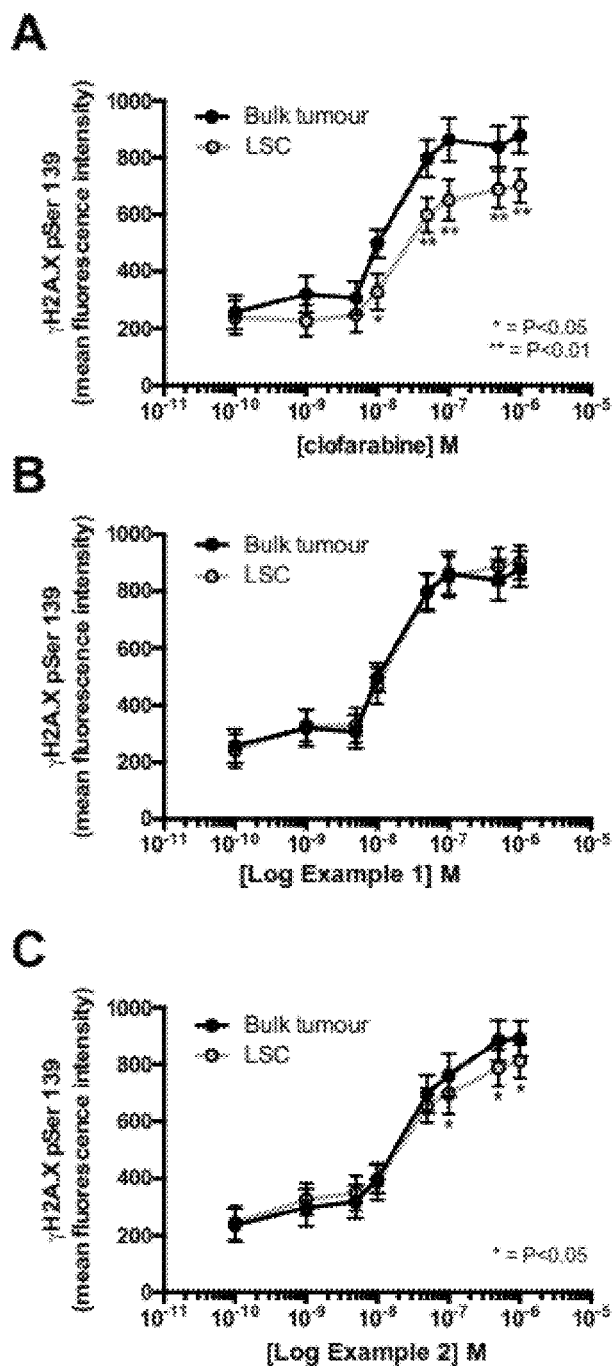
EXAMPLE 5

SALTS OF DIPHOSPHATE PHOSPHORAMIDATE OF NUCLEOSIDES AS ANTICANCER COMPOUNDS

RELATED APPLICATIONS

This application is the U.S. national phase of International Patent Application No. PCT/GB2018/053525, filed Dec. 5, 2018, which claims the benefit of priority of United Kingdom Patent Application No. GB 1720279.7, filed Dec. 5, 2017. The contents of the International Patent Application No. PCT/GB2018/053525 are hereby incorporated by reference in their entirety.

The present invention provides compounds useful in the treatment of cancer, e.g. leukaemia. The compounds comprise a salt of a diphosphate phosphoramidate. The present invention also provides formulations of said compounds and uses of said compounds.

BACKGROUND TO THE INVENTION

Nucleoside based drugs have become a powerful tool in the treatment of human disease. In the treatment of cancer, in particular, the use of nucleoside drugs such as gemcitabine, clofarabine, cytarabine, fludarabine is widespread.

The effectiveness of all nucleoside drugs however can be limited by both inherent and acquired resistance mechanisms.

One way in which the efficacy of nucleoside drugs can be improved is by administration as a drug of the ProTide class. Drugs of the ProTide class are prodrugs of monophosphorylated nucleosides and have been shown to be particularly potent therapeutic agents in the fields of both antivirals and oncology. These compounds appear to avoid many of the resistance mechanisms which limit the utility of the parent nucleosides (see, for example, 'Application of ProTide Technology to Gemcitabine: A Successful Approach to Overcome the Key Cancer Resistance Mechanisms Leads to a New Agent (NUC-1031) in Clinical Development'; Slusarczyk et al; *J. Med. Chem.*; 2014, 57, 1531-1542; McGuigan et al.; *Phosphoramidate ProTides of the anticancer agent FUDR successfully deliver the preformed bioactive monophosphate in cells and confer advantage over the parent nucleoside; J. Med. Chem.*; 2011, 54, 7247-7258; and Vande Voorde et al.; *The cytostatic activity of NUC-3073, a phosphoramidate prodrug of 5-fluoro-2'-deoxyuridine, is independent of activation by thymidine kinase and insensitive to degradation by phosphorolytic enzymes; Biochem. Pharmacol.*; 2011, 82, 441-452; WO2005/012327; WO2006/100439; WO2012/117246 and WO2016/083830). An exemplary ProTide is NUC-1031, a ProTide of gemcitabine:

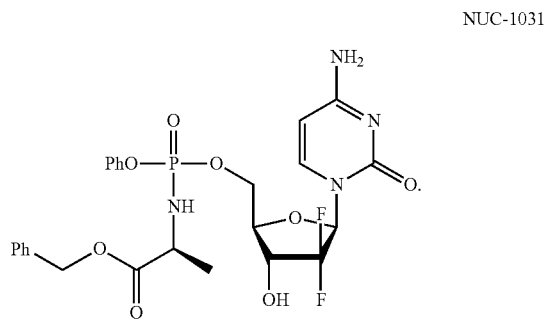

Whilst the ProTide strategy has proved to be very effective for certain nucleosides, it is not as effective with other nucleoside drugs. There is therefore a need to find further methods of potentiating nucleoside drug molecules.

Drugs of the ProTide class can also be poorly soluble in aqueous solvents and this can make administration challenging.

It is an aim of certain embodiments of the present invention to provide a therapeutic agent that, in use, has therapeutic efficacy in the prophylaxis or treatment of cancer.

It is an aim of certain embodiments of the present invention to provide a therapeutic agent that, in use, has a greater therapeutic efficacy in the prophylaxis or treatment of cancer than the parent nucleotide or the corresponding ProTide.

It is an aim of certain embodiments of the present invention to provide a therapeutic agent that is more conveniently administered than the corresponding ProTide.

Certain embodiments of the present invention solve some or all of the above stated objects.

STATEMENT OF THE INVENTION

In a first aspect of the invention there is provided a compound of formula (I), or a pharmaceutically acceptable salt thereof:

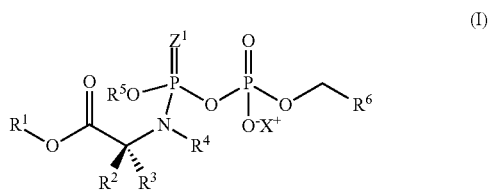

wherein $R^1$ is independently at each occurrence selected from: $C_1$-$C_{24}$-alkyl, $C_3$-$C_{24}$-alkenyl, $C_3$-$C_{24}$-alkynyl, $C_0$-$C_4$-alkylene-$C_3$-$C_8$-cycloalkyl and $C_0$-$C_4$-alkylene-aryl;

$R^2$ and $R^3$ are each independently at each occurrence selected from H, $C_1$-$C_6$-alkyl and $C_1$-$C_3$-alkylene-$R^7$; or $R^2$ and $R^3$ together with the atom to which they are attached form a 3- to 6-membered cycloalkyl or heterocycloalkyl group;

$R^4$ is independently at each occurrence H or $C_1$-$C_4$-alkyl;

or $R^4$, a group selected from $R^2$ and $R^3$ and the atoms to which they are attached may form a 3- to 6-membered heterocycloalkyl group;

$R^5$ is independently at each occurrence selected from aryl, 5-, 6-, 9- or 10-membered heteroaryl, $C_3$-$C_8$-cycloalkyl, 3- to 7-membered heterocycloalkyl, $C_1$-$C_3$-alkylene-$R^6$ and $C_1$-$C_8$-alkyl; said aryl being optionally fused to $C_6$-$C_8$-cycloalkyl;

$R^5$ is independently at each occurrence selected from aryl, 5-, 6-, 9- or 10-membered heteroaryl, $C_3$-$C_8$-cycloalkyl, 3- to 7-membered heterocycloalkyl, said aryl being optionally fused to $C_6$-$C_8$-cycloalkyl;

$R^6$ is independently selected from:

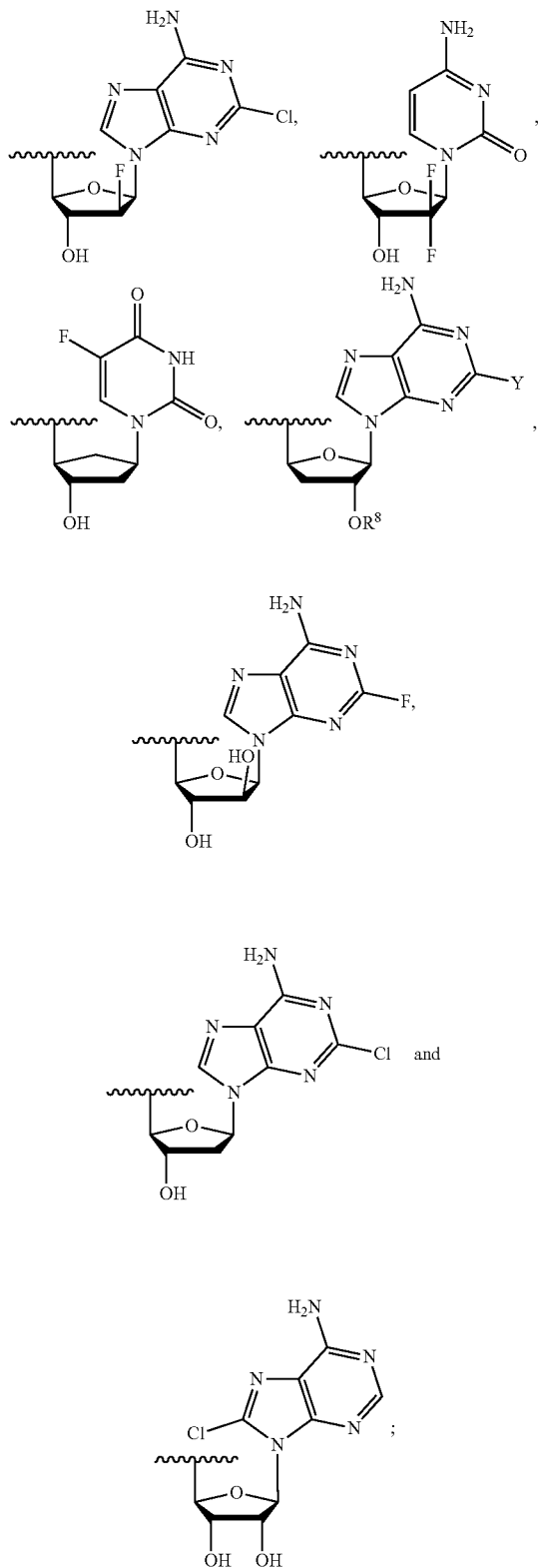

$R^7$ is independently at each occurrence selected from aryl, imidazole, indole, $SR^a$, $OR^a$, $CO_2R^a$, $CO_2NR^aR^a$, $NR^aR^b$ and $NH(\!=\!NH)NH_2$;

$R^8$ is independently selected from H and

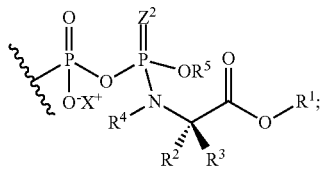

$Z^1$ and $Z^2$ are each independently selected from O and S;
Y is independently selected from H, F, Cl and OMe;
X is independently at each occurrence a pharmaceutically acceptable cation;
wherein any aryl group is either phenyl or naphthyl;
wherein where any of $R^1$, $R^2$, $R^3$, $R^4$, $R^5$ or $R^7$ is an alkyl, cycloalkyl, heterocycloalkyl, aryl or heteroaryl, that alkyl, cycloalkyl, heterocycloalkyl, aryl or heteroaryl group is optionally substituted with from 1 to 4 substituents selected from: halo, nitro, cyano, $NR^aR^a$, $NR^aS(O)_2R^a$, $NR^aC(O)R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^a$, $C(O)R^a$, $CONR^aR^a$, $CR^aR^aN\text{-}R^aR^a$, $C_1$-$C_4$-alkyl, $C_2$-$C_4$-alkenyl, $C_2$-$C_4$-alkynyl and $C_1$-$C_4$-haloalkyl;
wherein $R^a$ is independently at each occurrence selected from: H and $C_1$-$C_4$-alkyl; and $R^b$ is independently at each occurrence selected from: H, $C_1$-$C_4$-alkyl and $C(O)$—$C_1$-$C_4$-alkyl.

The inventors have found that phosphoramidated diphosphates of formula (I) have good activities against a range of cancer cell lines, including solid tumour and haematological cancer cell lines. In many cases the diphosphates of formula (I) are more active than the corresponding ProTide.

Diphosphate prodrugs reported in the literature such as for example nucleoside pyrophosphate diesters based on glicerides (K. Y. Hostetler et al. J. Biol. Chem. 1990, 265, 6112-6117; G. M. T. can Wijk, K. Y. Hostetler et al. *Biochim. Biophys. Acta Lipids Lipid Metab.* 1991, 1084, 307-310) are known to be unstable due to cleavage of a bond of the P—O—P group, thus releasing the corresponding nucleoside monophosphate instead of desired diphosphate. The inventors have found, however, that deprotonation of the α-phosphate group of diphosphate phosphoramidates provides high stability. The ionic nature of the compounds of the invention also means that they are more soluble in water than the corresponding ProTide.

A number of enzymatic processes are needed to convert a ProTide into the corresponding monophosphate nucleotide, including ester cleavage by carboxylesterases and cleavage of the resultant amino acid from the monophosphate nucleoside phosphoramidase-type enzymes. The diphosphate phosphoramidates of the invention are larger molecules, having a different shape and they are ionic, casting doubt over whether they will interact with the relevant enzymes in the same way for conversion to the diphosphate nucleotide. Indeed, in preliminary data, the inventors have shown that the diphosphate phosphoramidates of formula (I) are stable with respect to carboxypeptidases, for example, carboxypeptidase Y, the enzymes that carry out the ester cleavage step in the conversion of drugs of the ProTide class to monophosphates. Nevertheless, the diphosphate phosphoramidates of formula (I) are still active in cells, suggesting that an alternative mechanism of action is taking place compared to drugs of the ProTide class. The inventors have also shown that where there is an alkyloxy group on the phosphoramidate phosphorous ($OR^5$ in Formula I) the compounds of the invention are active. In drugs of the ProTide class, this is not typically the case and only compounds having aryloxy groups at this position provide good activity. This is understood to be because the aryloxy group acts as a leaving group during the activation of drugs of the ProTide class. Again, this indicates that the diphosphate phosphoramidates of the invention are activated via a different mechanism to drugs of the ProTide class.

In embodiments, the compound of formula (I) is a compound of formula (II):

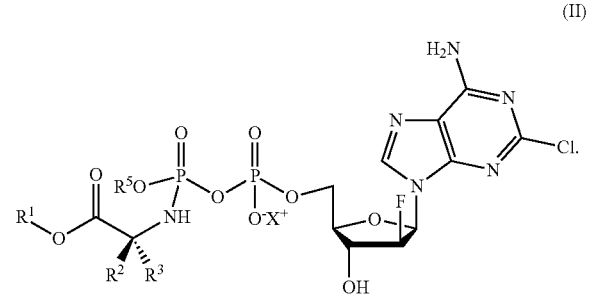

(II)

Diphosphate phosphoramidates of clofarabine such as those of formula (II) were more active than the corresponding ProTide against a number of cancer cell lines, including the haematological cell lines.

In embodiments, the compound of formula (I) is a compound of formula (III):

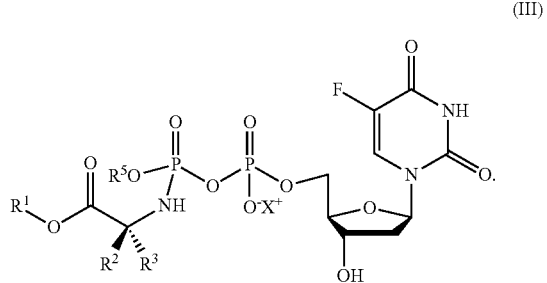

(III)

In embodiments, the compound of formula (I) is a compound of formula (IV):

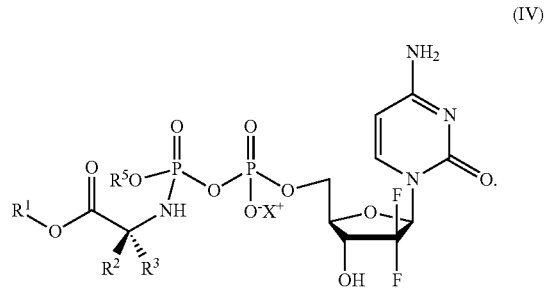

(IV)

In embodiments, the compound of formula (I) is a compound of formula (V):

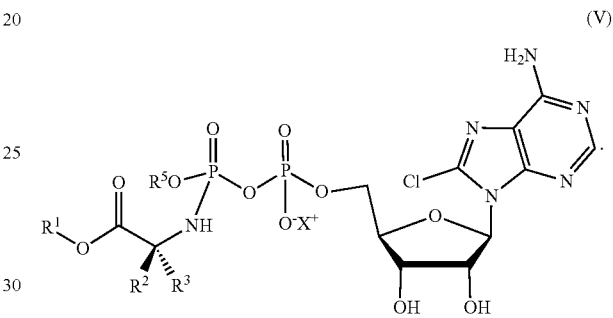

(V)

In embodiments, the compound of formula (I) is a compound of formula (VI):

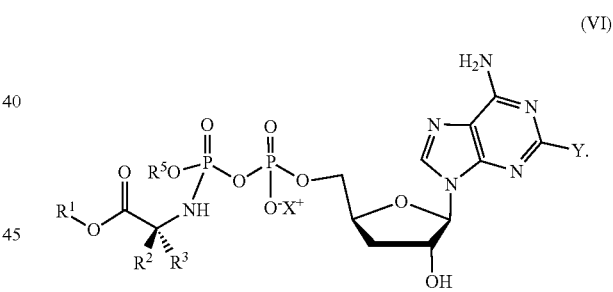

(VI)

In embodiments, the compound of formula (I) is a compound of formula (VII):

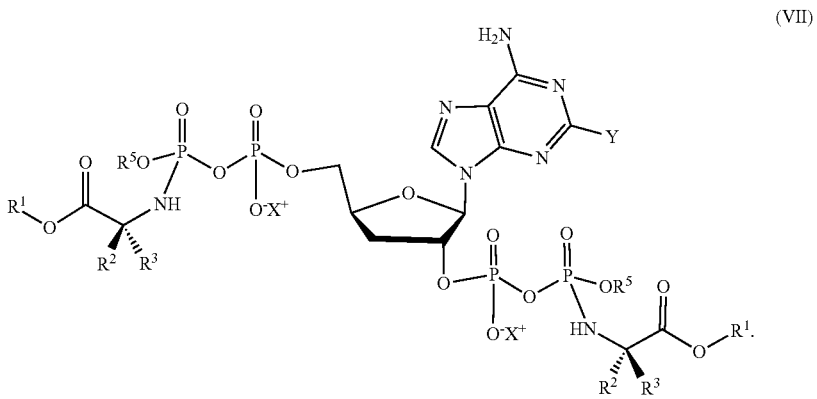

(VII)

In these embodiments, it may be that $R^1$, $R^2$, $R^3$, $R^5$ and X are the same at both occurrences.

The following statements apply to compounds of any of formulae (I) to (VII). These statements are independent and interchangeable. In other words, any of the features described in any one of the following statements may (where chemically allowable) be combined with the features described in one or more other statements below. In particular, where a compound is exemplified or illustrated in this specification, any two or more of the statements below which describe a feature of that compound, expressed at any level of generality, may be combined so as to represent subject matter which is contemplated as forming part of the disclosure of this invention in this specification.

$R^1$ may be independently at each occurrence selected from: $C_1$-$C_{24}$-alkyl, $C_3$-$C_{24}$-alkenyl, $C_3$-$C_{24}$-alkynyl, $C_0$-$C_4$-alkylene-$C_3$-$C_6$-cycloalkyl and $C_0$-$C_4$-alkylene-aryl.

$R^1$ may be independently at each occurrence selected from: $C_1$-$C_{24}$-alkyl, $C_0$-$C_4$-alkylene-$C_3$-$C_8$-cycloalkyl and $CH_2$-aryl. $R^1$ may be independently at each occurrence selected from: $C_1$-$C_{10}$-alkyl, $C_4$-$C_6$-cycloalkyl and benzyl. $R^1$ may be independently at each occurrence selected from: $C_1$-$C_8$-alkyl, $C_6$-cycloalkyl and benzyl.

$R^1$ may be $C_1$-$C_6$ alkyl.

$R^1$ may be selected such that it comprises three or more carbon atoms. $R^1$ may be selected such that it comprises five or more carbon atoms. $R^1$ may therefore be selected such that it includes six or more carbon atoms. $R^1$ is preferably selected such that it comprises only carbon and hydrogen atoms. $R^1$ may be selected from $C_5$-$C_7$-cycloalkyl, $C_5$-$C_8$-alkyl and benzyl, optionally wherein said groups are unsubstituted. $R^1$ may be unsubstituted benzyl. $R^1$ may be neopentyl. $R^1$ may be ethyl.

It may be that $R^3$ is H. It may be that $R^3$ is $C_1$-$C_4$-alkyl. It may be that $R^3$ is methyl. It may be that $R^2$ is selected from $C_1$-$C_6$-alkyl and $C_1$-$C_3$-alkylene-$R^7$. It may be that $R^2$ is $C_1$-$C_4$-alkyl. It may be that $R^2$ is selected from methyl and isopropyl. $R^2$ may be methyl. $R^2$ may be H.

$R^4$ is preferably H.

It may be that $R^4$, a group selected from $R^2$ and $R^3$, and the atoms to which they are attached form a 3- to 6-membered heterocycloalkyl group. It may be that $R^4$, a group selected from $R^2$ and $R^3$, and the atoms to which they are attached do not form a 3- to 6-membered heterocycloalkyl group. It may be that $R^2$ and $R^3$ are each independently at each occurrence selected from H, $C_1$-$C_6$-alkyl and $C_1$-$C_3$-alkylene-$R^7$; or $R^2$ and $R^3$ together with the atom to which they are attached form a 3- to 6-membered heterocycloalkyl group; and $R^4$ is independently at each occurrence H or $C_1$-$C_4$-alkyl.

It may be that $R^5$ is substituted or unsubstituted phenyl, which may be optionally fused to a $C_6$-$C_8$-cycloalkyl ring, e.g. a cyclohexane ring. It may be that $R^5$ is substituted or unsubstituted phenyl. It may be that $R^5$ is substituted or unsubstituted naphthyl (e.g. 1-naphthyl). Preferably, $R^5$ is selected from unsubstituted phenyl or unsubstituted naphthyl (e.g. 1-naphthyl). Thus, $R^5$ may be unsubstituted phenyl. Alternatively, $R^5$ may be unsubstituted naphthyl (e.g. 1-naphthyl).

$R^6$ may be

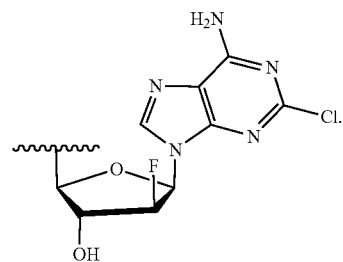

$R^6$ may be

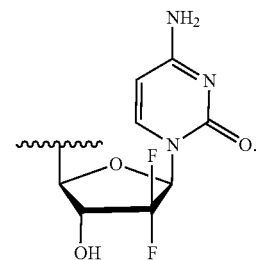 [SMILES: *[C@H]1O[C@@H](n2ccc(N)nc2=O)C(F)(F)[C@H]1O]

$R^6$ may be

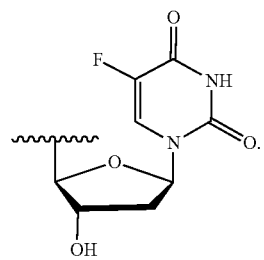 [SMILES: *[C@H]1O[C@@H](n2cc(F)c(=O)[nH]c2=O)C[C@H]1O]

$R^6$ may be

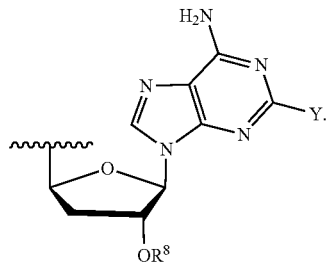

Y may be H. Y may be F.

$R^8$ may be H. $R^8$ may be R
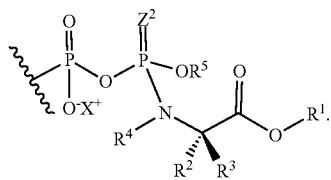
$Z^2$ may be S. $Z^2$ may be O.
Where $R^8$ is
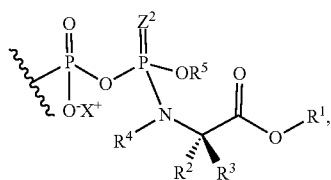
it may be that $R^1$, $R^2$, $R^3$, $R^5$, X and $Z^2$ are the same at both occurrences.
$R^6$ may be
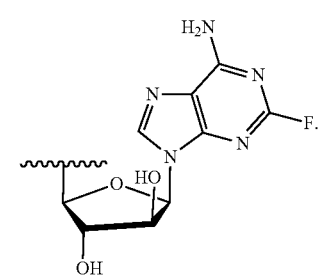
$R^6$ may be
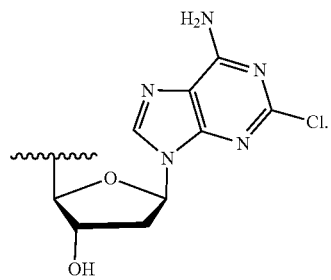 [SMILES: *[C@H]1O[C@@H](n2cnc3c(N)nc(Cl)nc32)C[C@H]1O]
$R^6$ may be
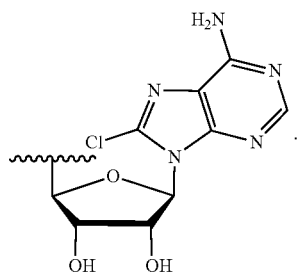
The compound of formula (I) may be selected from:
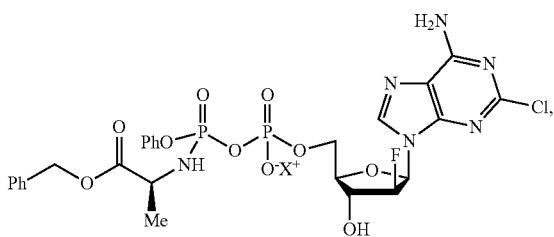
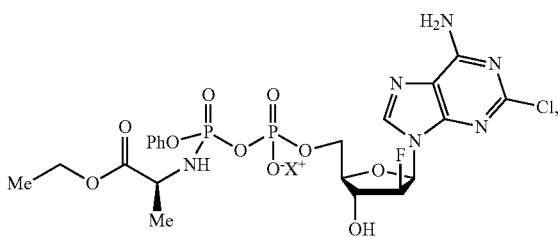
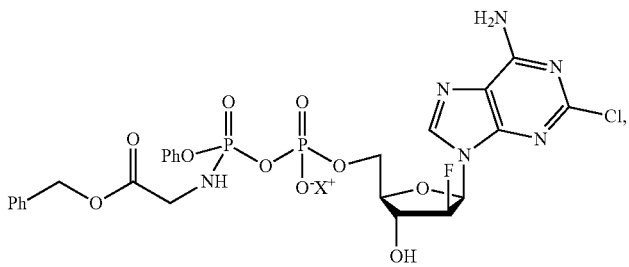
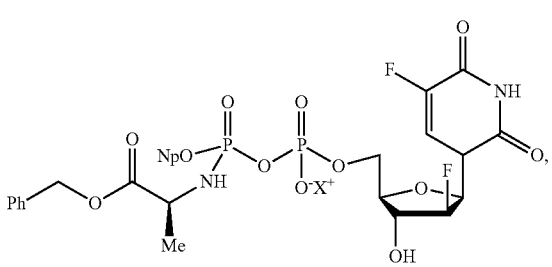

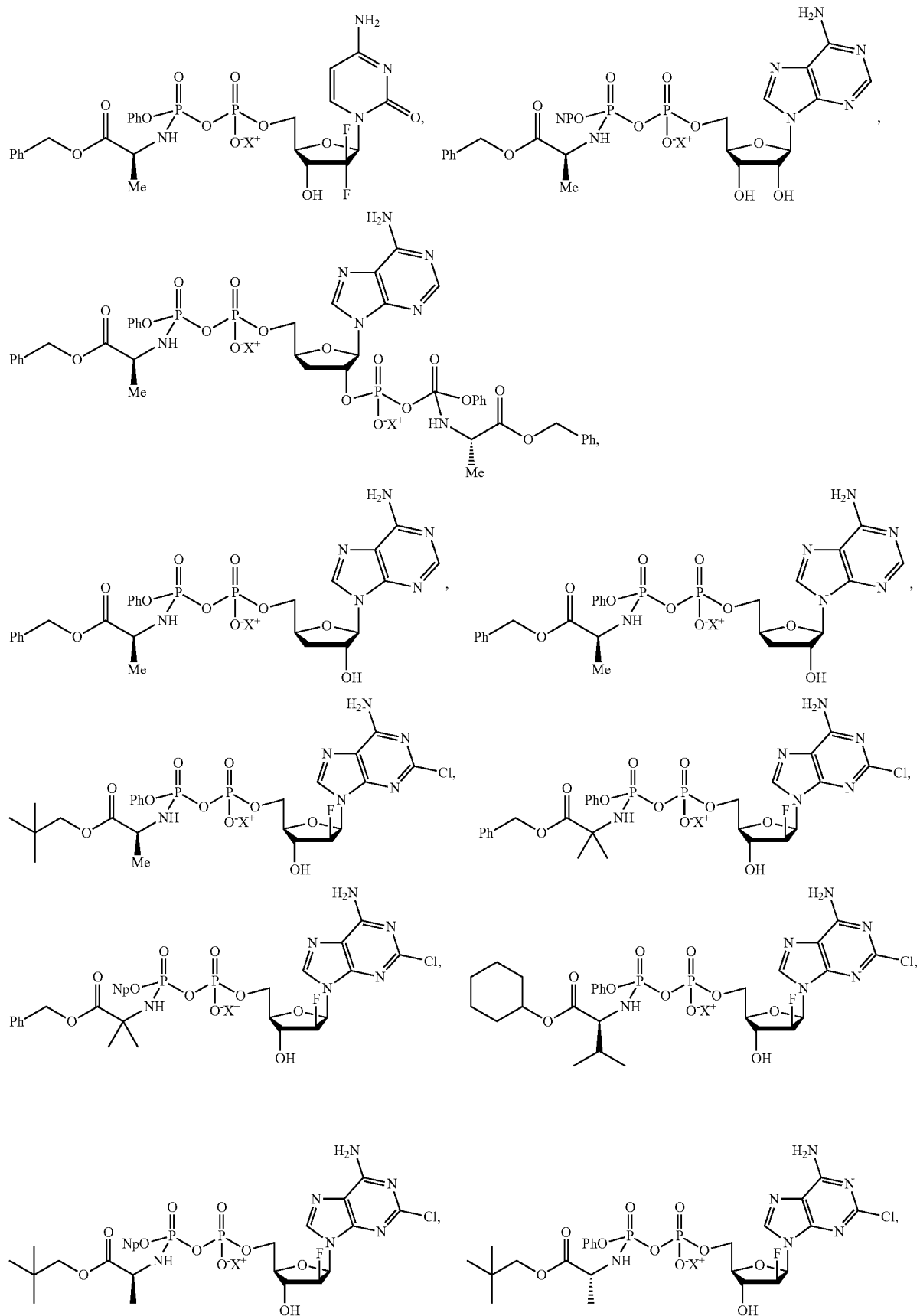

-continued

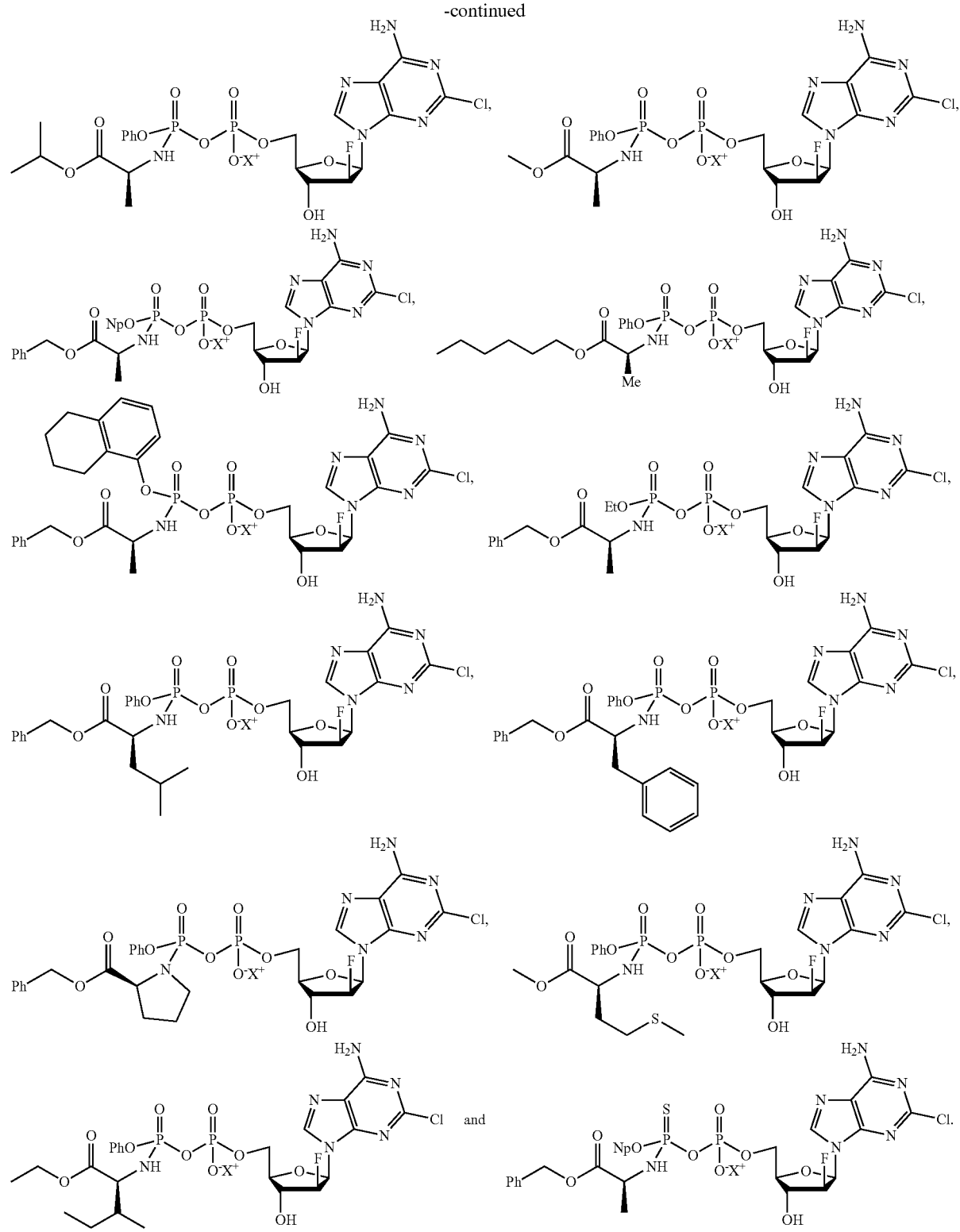

X+ may be a metal cation or it may be an ammonium cation. X+ may be a metal cation, e.g. a cation of an alkali or alkali earth metal. X+ may be an ammonium cation, e.g. a trialkylammonium cation or an ammonium cation of a nitrogen heterocycle. Illustrative cations include those derived from aluminium, arginine, benzathine, calcium, choline, diethylamine, diolamine, glycine, lysine, magnesium, meglumine, olamine, potassium, sodium, tromethamine, triethylamine and zinc cations. X+ may be a triethylamine cation.

Compounds of the invention comprise a chiral centre at the phosphorus atom (β-phosphorus) that is bonded to OR⁵.

The compound may be present as a mixture of phosphate diastereoisomers, as the (S)-epimer at the phosphorus atom in substantially diastereomerically pure form or as the (R)-epimer at the phosphorus atom in substantially diastereomerically pure form. 'Substantially diastereomerically pure' is defined for the purposes of this invention as a diastereomeric purity of greater than about 90%. If present as a substantially diastereoisomerically pure form, the compound may have a diastereoisomeric purity of greater than 95%, 98%, 99%, or even 99.5%. Alternatively, the compound may be present as a mixture of phosphate diastereoisomers.

The (R)- and/or (S)-epimers of the compound can be obtained in substantially diastereomerically pure form by chromatography, e.g. HPLC optionally using a chiral column. Alternatively, the (R)- and/or (S)-epimers of the compound can be obtained in substantially diastereomerically pure form by crystallisation from an appropriate solvent or solvent system.

According to a second aspect of the present invention, there is provided a compound of formula (I), or a pharmaceutically acceptable salt thereof, for use in a method of treatment.

According to a third aspect of the present invention, there is provided a compound of formula (I), or a pharmaceutically acceptable salt thereof, for use in the prophylaxis or treatment of cancer.

According to a fourth aspect of the present invention there is provided use of a compound of formula (I), or a pharmaceutically acceptable salt thereof, in the manufacture of a medicament for the prophylaxis or treatment of cancer.

According to a fifth aspect of the present invention, there is provided a method of prophylaxis or treatment of cancer comprising administration to a patient in need of such treatment an effective dose of a compound of formula (I), or a pharmaceutically acceptable salt thereof.

With respect to each of the third, fourth, and fifth aspects of the present invention, embodiments of the invention comprise a cancer selected from but not restricted to the group consisting of: pancreatic cancer, bladder cancer, other urothelial cancers (e.g. cancers of ureter and renal pelvis), gastrointestinal cancers (also known as cancer of the digestive tract, including: oesophageal cancer, gastric cancer, stomach cancer, bowel cancer, small intestine cancer, colon cancer, colorectal cancer, appendix mucinous, goblet cell carcinoid, liver cancer, biliary cancer, gallbladder cancer, anal cancer and rectal cancer), lung cancer, renal (or kidney) cancer, biliary cancer, prostate cancer, cholangiocarcinoma, neuroendocrine cancer, sarcoma, lymphoma, thymic cancer, glioblastoma multiforme, a cancer of an unknown primary origin, mesothelioma, adrenal cancer, testicular cancer, cancer of the central nervous system, basal cell carcinoma, Bowens disease, other skin cancers (such as malignant melanoma, merckel cell tumour and rare appendage tumours), ocular surface squamous neoplasia, germ cell tumours, leukaemia, multiple myeloma, lung cancer, liver cancer, breast cancer, head and neck cancer, neuroblastoma, thyroid carcinoma, oral squamous cell carcinoma, urinary bladder cancer, Leydig cell tumour, and gynaecological cancers (including ovarian cancer, cancer of the fallopian tube, peritoneal cancer, endometrial cancer, uterine cancer and cervical cancer, including epithelia cervix carcinoma).

In certain embodiments, the cancer is a leukaemia or a lymphoma.

The cancer may be a leukaemia.

There are four main types of leukaemia depending on whether they are chronic or acute, and myeloid or lymphoid in origin. These are: acute myeloblastic leukaemia (AML), acute lymphoblastic leukaemia (ALL), chronic myelogenous leukaemia (CML) and chronic lymphocytic leukaemia (CLL).

Mixtures of these are also known; e.g. biphenotypic acute leukaemia (BAL; which is a mix of AML and ALL).

In particular embodiments, the leukaemia is selected from the group consisting of: acute myeloblastic leukaemia (AML), acute lymphoblastic leukaemia (ALL), chronic myelogenous leukaemia (CML), chronic lymphocytic leukaemia (CLL) and biphenotypic acute leukaemia (BAL; which is a mix of AML and ALL).

Chronic lymphocytic leukaemia (CLL) includes the subtypes: B-cell CLL (B-CLL), B-cell prolymphocytic leukaemia (PLL) and T-cell chronic prolymphocytic leukaemia (T-PLL) and several subtypes that differ at the genetic level.

Acute lymphoblastic leukaemia (ALL) includes the subtypes: precursor B-cell ALL (B-ALL), precursor T-cell ALL (T-ALL), Burkitt-type ALL and Philadelphia chromosome positive (BCR-ABL fusion) ALL.

Acute myeloblastic leukaemia (AML) includes the subtypes: myeloid leukaemia, monocytic leukaemia and acute promyelocytic leukaemia (APL).

Chronic myelogenous leukaemia (CML) includes the subtypes: chronic granulocytic leukaemia (CGL) (CGL), Juvenile CML (JCML), chronic neutrophilic leukaemia (CNL), chronic myelomonocytic leukaemia (CMML) and atypical CML (aCML).

In particular embodiments, any of the above sub-types of CLL, ALL, AML and CML are suitable for treatment with the compounds of the invention or pharmaceutical compositions containing them Other forms of leukemia that can be considered to sit outside of these four main groups include: erythroleukemia, arising from red blood cell precursors; and a lymphoma that has gone into the blood.

The cancer may be a lymphoma, e.g. a solid lymphoma.

There are two main types of lymphoma: Hodgkin's lymphoma and non-Hodgkin's lymphoma. Within each of these there are various subtypes.

In particular embodiments, the lymphoma is selected from the group consisting of: Hodgkin's lymphoma and non-Hodgkin's lymphoma.

In particular embodiments, the lymphoma is selected from the group consisting of: Burkitt's lymphoma (BL), mantle cell lymphoma (MCL), follicular lymphoma (FL), small lymphocytic lymphoma (SLL) indolent B-cell non-Hodgkin's lymphoma, histiocytic lymphoma (aka immunoblastic lymphoma; IBL) and diffuse large B-cell lymphoma (DLBCL), including activated-cell like diffuse large B-cell lymphoma (DLBCL-ABC) and germinal center B-cell like diffuse large B-cell lymphoma (DLBCL-GCB).

In certain embodiments, the cancer is a gastrointestinal cancer and can be selected from the group consisting of: oesophageal cancer, gastric cancer, stomach cancer, bowel cancer, small intestine cancer, colon cancer, colorectal cancer, appendix mucinous, goblet cell carcinoid, liver cancer, biliary cancer, gallbladder cancer, anal cancer and rectal cancer.

In certain embodiments, the cancer is of gynaecological origin and can be selected from the group consisting of: a cancer of the uterus, cancer of the fallopian tube, cancer of the endometrium, cancer of the ovary, cancer of the peritoneum and cancer of the cervix).

Suitably the ovarian cancer may be epithelial ovarian cancer. Suitably the peritoneal cancer may be primary peritoneal cancer.

In particular, the cancer may be selected from, but not restricted to pancreatic cancer, lung cancer, bladder cancer, breast cancer, biliary cancer, lymphoma, a leukaemia, a gastrointestinal cancer and a gynaecological cancer.

The compounds of the invention have been found to retain activity even under hypoxic conditions. Cancers particularly associated with hypoxia are pancreatic and renal (or kidney) cancers.

The cancer may be relapsed. The cancer may be metastatic. The cancer may be previously untreated.

The cancer may be refractory cancer that has previously been treated but has proven unresponsive to prior treatment. Alternatively, the cancer patient may be intolerant of a previous therapy, for example, may develop side effects that make the patient intolerant to further treatment with the agent being administered.

According to a sixth aspect of the present invention, there is provided a pharmaceutical composition comprising a compound of formula (I), or a pharmaceutically acceptable salt thereof, and at least one pharmaceutically acceptable excipient. The pharmaceutical composition may be for use in the prophylaxis or treatment of cancer, e.g. a cancer or group of cancers mentioned above.

The compound of formula (I) may be as described in the following numbered paragraphs:

1. In a first aspect of the invention is provided a compound of formula (I), or a pharmaceutically acceptable salt thereof:

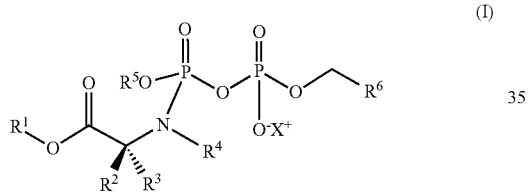

(I)

wherein $R^1$ is independently at each occurrence selected from: $C_1$-$C_{24}$-alkyl, $C_3$-$C_{24}$-alkenyl, $C_3$-$C_{24}$-alkynyl, $C_0$-$C_4$-alkylene-$C_3$-$C_6$-cycloalkyl or $C_0$-$C_4$-alkylene-aryl;

$R^2$ and $R^3$ are each independently at each occurrence selected from H, $C_1$-$C_6$-alkyl and $C_1$-$C_3$-alkylene-$R^7$; or $R^2$ and $R^3$ together with the atom to which they are attached form a 3- to 6-membered cycloalkyl or heterocycloalkyl group;

$R^4$ is independently at each occurrence H or $C_1$-$C_4$-alkyl;

$R^5$ is independently at each occurrence selected from aryl and 5-, 6-, 9- or 10-membered heteroaryl;

$R^6$ is independently selected from:

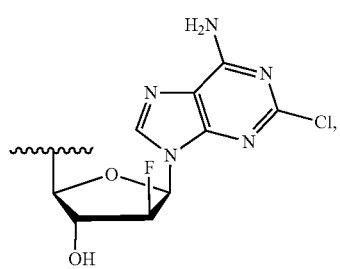

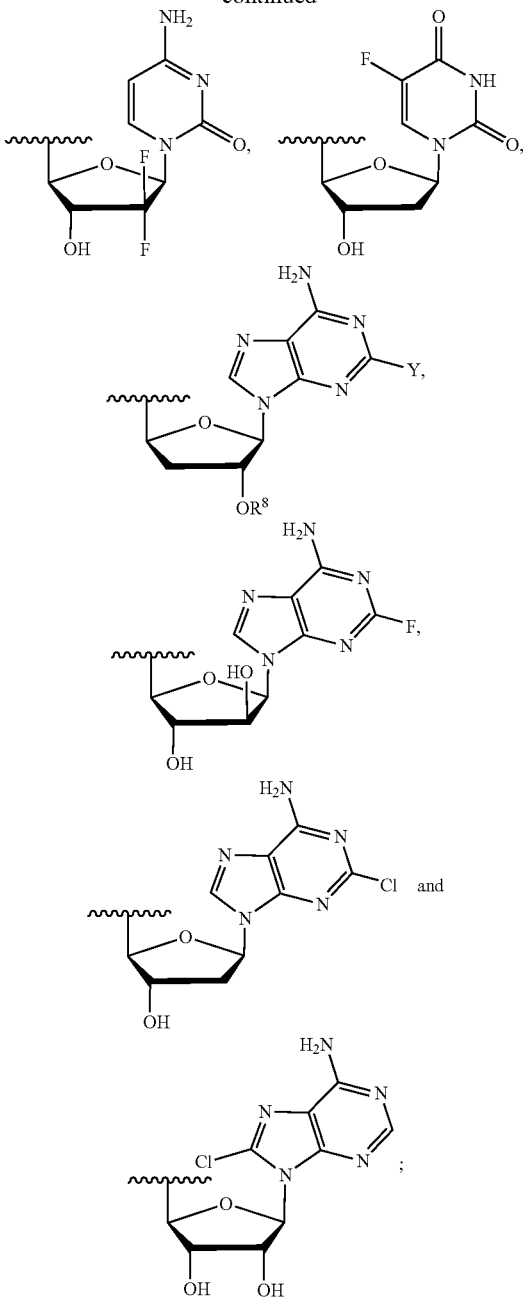

$R^7$ is independently at each occurrence selected from aryl, imidazole, indole, $SR^a$, $OR^a$, $CO_2R^a$, $CO_2NR^aR^a$, $NR^aR^b$ and $NH(\!=\!\!NH)NH_2$;

$R^8$ is independently selected from H and

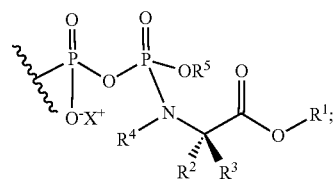

Y is independently selected from H, F, Cl and OMe;

X is independently at each occurrence a pharmaceutically acceptable cation;

wherein any aryl group is either phenyl or naphthyl;

wherein where any of $R^1$, $R^2$, $R^3$, $R^4$, $R^5$ or $R^7$ is an alkyl, cycloalkyl, heterocycloalkyl, aryl or heteroaryl, that alkyl, cycloalkyl, heterocycloalkyl, aryl or heteroaryl group is optionally substituted with from 1 to 4 substituents selected from: halo, nitro, cyano, $NR^aR^a$, $NR^aS(O)_2R^a$, $NR^aC(O)R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^a$, $C(O)R^a$, $CONR^aR^a$, $CR^aR^aN-R^aR^a$, $C_1$-$C_4$-alkyl, $C_2$-$C_4$-alkenyl, $C_2$-$C_4$-alkynyl and $C_1$-$C_4$-haloalkyl;

wherein $R^a$ is independently at each occurrence selected from: H and $C_1$-$C_4$-alkyl; and $R^b$ is independently at each occurrence selected from: H, and $C_1$-$C_4$-alkyl and $C(O)$—$C_1$-$C_4$-alkyl.

2. A compound of paragraph 1, wherein $R^4$ is H.

3. A compound of paragraph 1 or paragraph 2, wherein $R^6$ is

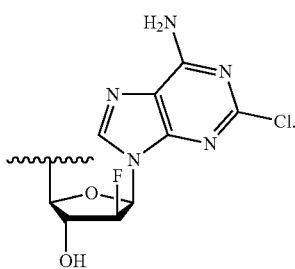

4. A compound of paragraph 1 or paragraph 2, wherein $R^6$ is

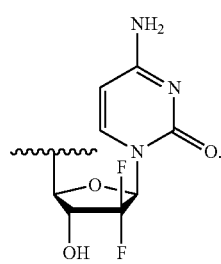

5. A compound of paragraph 1 or paragraph 2, wherein $R^6$ is

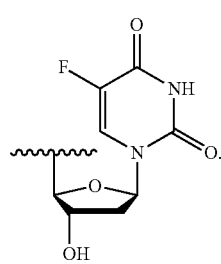

6. A compound of paragraph 1 or paragraph 2, wherein $R^6$ is

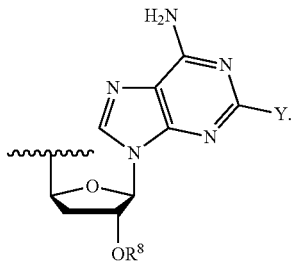

7. A compound of paragraph 6, wherein Y is H.

8. A compound of paragraph 6, wherein Y is F.

9. A compound of any one of paragraphs 6 to 8, wherein $R^8$ is H.

10. A compound of any one of paragraphs 6 to 8, wherein $R^8$ is

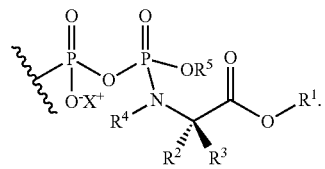

11. A compound of paragraph 1 or paragraph 2, wherein $R^6$ is

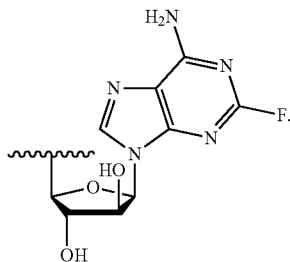

12. A compound of paragraph 1 or paragraph 2, wherein $R^6$ is

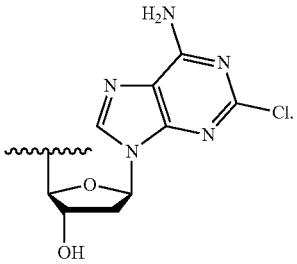

13. A compound of paragraph 1 or paragraph 2, wherein $R^6$ is

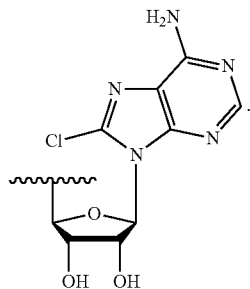

14. A compound of any one of paragraphs 1 to 13, wherein $R^1$ is selected from $C_5$-$C_7$-cycloalkyl, $C_1$-$C_8$-alkyl and benzyl.
15. A compound of paragraph 14, wherein $R^1$ is benzyl.
16. A compound of paragraph 14, wherein $R^1$ is $C_1$-$C_8$-alkyl, e.g. ethyl.
17. A compound of any one of paragraphs 1 to 16, wherein $R^3$ is H.
18. A compound of any one of paragraphs 1 to 17, wherein $R^2$ is $C_1$-$C_4$-alkyl.
19. A compound of any one of paragraphs 1 to 17, wherein $R^2$ is H.
20. A compound of any one of paragraphs 1 to 19, wherein $R^5$ is phenyl.
21. A compound of any one of paragraphs 1 to 19, wherein $R^5$ is naphthyl.
22. A compound of any one of paragraphs 1 to 21 wherein $X^+$ is a metal cation or an ammonium cation.
23. A compound of any one of paragraphs 1 to 22 for medical use.
24. A compound of any one of paragraphs 1 to 23 for use in treating cancer.
25. A compound for use of paragraph 24, wherein the cancer is leukaemia or lymphoma.
26. A compound for use of paragraph 25, wherein the cancer is a leukaemia selected from the group consisting of acute lymphoblastic leukaemia, acute myelogenous leukaemia, myelodysplastic syndromes, acute promyelocytic leukaemia, acute lymphocytic leukaemia, chronic myelogenous leukaemia, chronic lymphocytic leukaemia, monoblastic leukaemia and hairy cell leukaemia.
27. A pharmaceutical composition comprising compounds of any one of claims 1 to 22 and at least one pharmaceutically acceptable excipient.

BRIEF DESCRIPTION OF THE FIGURES

Embodiments of the invention are further described hereinafter with reference to the accompanying drawings, in which:

FIG. 5 shows comparison of the DNA damage, as measured by γH2A.X phosphorylation assay, induced in purified LSCs and bulk tumour cells following 2-hour exposure to (A) clofarabine, (B) Example 1 and (C) Example 2 under hypoxic conditions (5% $O_2$). All data are the mean (±SD) of three independent experiments.

DETAILED DESCRIPTION

Figure 1:
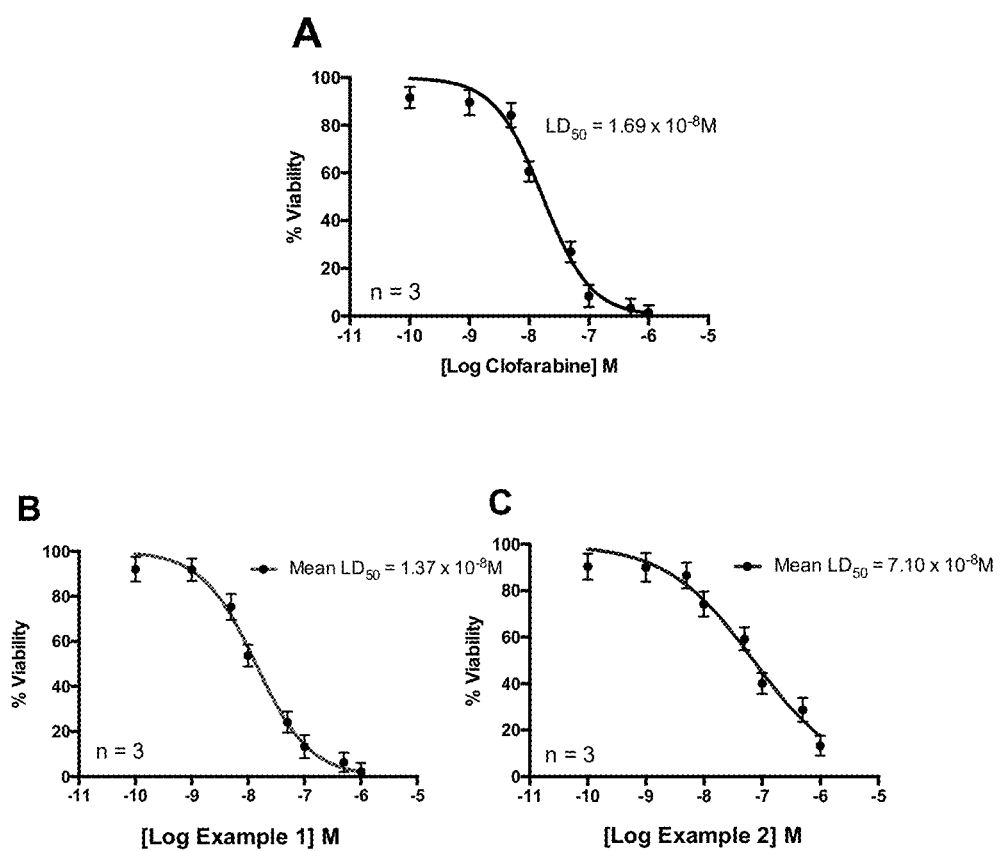
FIG. 1 shows sigmoidal dose-response curves for (A) clofarabine, (B) Example 1 and (C) Example 2. Clofarabine and Example 1 showed the highest potency. All assays were carried out using KG1a cells and data are presented as mean (±SD) of three independent experiments.
Figure 2:
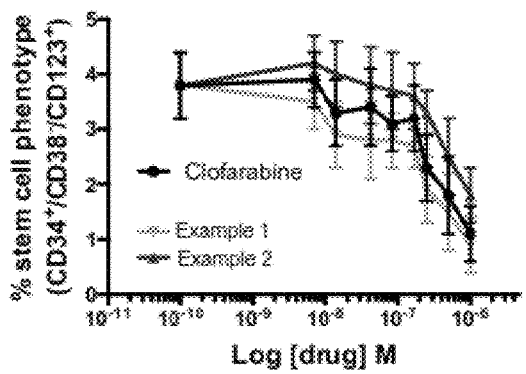
FIG. 2 shows analysis of the LSC targeting capacity of clofarabine Example 1 and Example 2. Under normoxic conditions, all of the compounds showed stem cell targeting at concentrations above $1\times10^7$M. All data are the mean (±SD) of three independent experiments.
Figure 2:
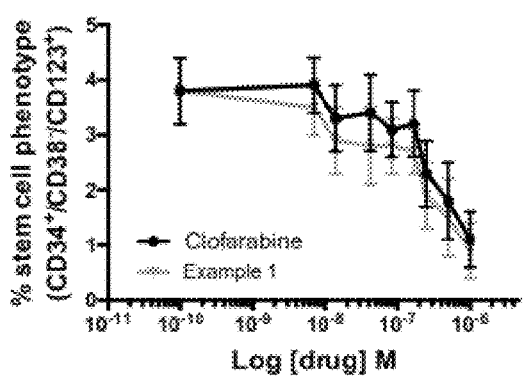
Figure 2:
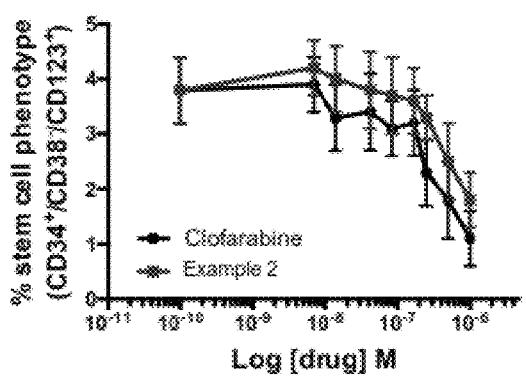

The term 'saline' is intended to refer to an aqueous solution of sodium chloride. Saline solutions of the present invention will typically be sterile and will typically be at a concentration suitable for use in parenteral administration. Suitable concentrations are up to 2 w/v % or up to 1 w/v %. To optimise osmolarity different concentrations of saline can be used in the formulations of the invention, e.g. 0.9% or 0.45%.

The formulations of the present invention can be used in the treatment of the human body. They may be used in the treatment of the animal body.

The compounds in the formulations of the invention may be obtained, stored and/or administered in the form of a pharmaceutically acceptable salt. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate, hemioxalate and hemicalcium salts.

For the above-mentioned formulations of the invention the dosage administered will, of course, vary with the compound employed, the precise mode of administration, the treatment desired and the disorder indicated. Dosage levels, dose frequency, and treatment durations of compounds of the invention are expected to differ depending on the formulation and clinical indication, age, and co-morbid medical conditions of the patient. The size of the dose for therapeutic purposes of compounds of the invention will naturally vary according to the nature and severity of the conditions, the age and sex of the animal or patient and the route of administration, according to well known principles of medicine.

A pharmaceutical formulation typically takes the form of a composition in which active compounds, or pharmaceutically acceptable salts thereof, are in association with a pharmaceutically acceptable adjuvant, diluent or carrier. One such pharmaceutically acceptable adjuvant, diluent or carrier in the formulations of the invention is the polar aprotic solvent. Conventional procedures for the selection and preparation of suitable pharmaceutical formulations are described in, for example, "Pharmaceuticals—The Science of Dosage Form Designs", M. E. Aulton, Churchill Livingstone, 1988.

The formulations may be suitable for topical application (e.g. to the skin or bladder), for oral administration or for parenteral (e.g. intravenous administration).

Any solvents used in pharmaceutical formulations of the invention should be pharmaceutical grade, by which it is meant that they have an impurity profile which renders them suitable for administration (e.g. intravenous administration) to humans.

For oral administration the formulations of the invention may comprise the active compound admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the active compounds may be admixed with, for example, a vegetable oil or polyethylene glycol. Hard gelatine capsules may contain granules of the compound using either the above-mentioned excipients for tablets. Also liquid or semisolid formulations of the active compounds may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

The formulations may be for parenteral (e.g. intravenous) administration. For parenteral (e.g. intravenous) administration the active compounds may be administered as a sterile aqueous or oily solution. Preferably, the active compounds are administered as a sterile aqueous solution. The aqueous solution may further comprise at least one surfactant and/or organic solvent. Illustrative organic solvents include dimethylacetamide, ethanol, ethyleneglycol, N-methyl-pyrrolidinone, dimethylsulfoxide, dimethylformamide and isopropanol. Illustrative surfactants include polyethoxylated fatty acids and fatty acid esters and mixtures thereof. Suitable surfactants include polyethoxylated castor oil (e.g. that sold under the trade name Kolliphor® ELP); or polyethoxylated stearic acid (e.g. that sold under the trade names Solutol® or Kolliphor® HS15); or polyethoxylated (e.g. polyoxyethylene (20)) sorbitan monooleate, (e.g. that are sold under the trade names Polysorbate 80 or Tween® 80).

The pharmaceutical composition of the invention will preferably comprise from 0.05 to 99% w (percent by weight) compound of the invention, more preferably from 0.05 to 80% w compound of the invention, still more preferably from 0.10 to 70% w compound of the invention, and even more preferably from 0.10 to 50% w compound of the invention, all percentages by weight being based on total composition.

Cyclodextrins have been shown to find wide application in drug delivery (Rasheed et al, *Sci. Pharm.,* 2008, 76, 567-598). Cyclodextrins are a family of cyclic oligosaccharides. They act as a 'molecular cage' which encapsulates drug molecules and alters properties of those drug molecules such as solubility. Cyclodextrins comprise (α-1,4)-linked α-D-glucopyranose units. Cyclodextrins may contains 6, 7 or 8 glucopyranose units (designated α-, β- and γ-cyclodextrins respectively). Cyclodextrins used in pharmaceutical formulations are often β-cyclodextrins. The pendant hydroxyl groups can be alkylated with a $C_1$-$C_6$ substituted or unsubstituted alkyl group. Examples of cyclodextrins are α-cyclodextrin, β-cyclodextrin, γ-cyclodextrin, 2-hydroxypropyl-β-cyclodextrin (HP-β-CD), sulfobutylether β-cyclodextrin sodium salt, partially methylated β-cyclodextrin. The formulations of the invention may also comprise at least one cyclodextrin.

The term $C_m$-$C_n$ refers to a group with m to n carbon atoms.

The term "alkyl" refers to a linear or branched hydrocarbon group. An alkyl group is monovalent. For example, $C_1$-$C_6$-alkyl may refer to methyl, ethyl, n-propyl, iso-propyl, n-butyl, sec-butyl, tert-butyl, n-pentyl and n-hexyl. The alkyl groups are preferably unsubstituted.

The term "alkylene" refers to a linear hydrocarbon chain. An alkylene group is divalent. For example, $C_1$-alkylene may refer to a $CH_2$ group. $C_2$-alkylene may refer to —$CH_2CH_2$— group. The alkylene groups are preferably unsubstituted.

The term "haloalkyl" refers to a hydrocarbon chain substituted with at least one halogen atom independently chosen at each occurrence from: fluorine, chlorine, bromine and iodine. The halogen atom may be present at any position on the hydrocarbon chain. For example, $C_1$-$C_4$-haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl. A halo alkyl group may be a fluoroalkyl group, i.e. a hydrocarbon chain substituted with at least one fluorine atom.

The term "alkenyl" refers to a branched or linear hydrocarbon chain containing at least one carbon-carbon double bond. The double bond(s) may be present as the E or Z isomer. The double bond may be at any possible position of the hydrocarbon chain. For example, "$C_2$-$C_4$-alkenyl" may refer to ethenyl, allyl and butenyl. The alkenyl groups are preferably unsubstituted.

The term "alkynyl" refers to a branched or linear hydrocarbon chain containing at least one carbon-carbon triple bond. The triple bond may be at any possible position of the hydrocarbon chain. For example, "$C_2$-$C_6$-alkynyl" may refer to ethynyl, propynyl, butynyl. The alkynyl groups are preferably unsubstituted.

The term "cycloalkyl" refers to a saturated hydrocarbon ring system containing 3, 4, 5 or 6 carbon atoms. For example, "3- to 6-membered cycloalkyl" may refer to cyclopropyl, cyclobutyl, cyclopentyl, cyclohexyl. The cycloalkyl groups are preferably unsubstituted.

The term "heterocycloalkyl" may refer to a saturated or partially saturated monocyclic group comprising 1 or 2 heteroatoms independently selected from O, S and N in the ring system (in other words 1 or 2 of the atoms forming the ring system are selected from O, S and N). Examples of heterocycloalkyl groups include; piperidine, piperazine, morpholine, thiomorpholine, pyrrolidine, tetrahydrofuran, tetrahydrothiophene, tetrahydropyran, dihydropyran, dioxane, azepine. The heterocycloalkyl groups are preferably unsubstituted or substituted.

The present invention also includes formulations of all pharmaceutically acceptable isotopically-labelled forms of compound wherein one or more atoms are replaced by atoms having the same atomic number, but an atomic mass or mass number different from the atomic mass or mass number of the predominant isotope usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds, for example, those incorporating a radioactive isotope, are useful in drug and/or substrate tissue distribution studies. The radioactive isotopes tritium, i.e. $^3H$, and carbon-14, i.e. $^{14}C$, and $^{18}F$ are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Isotopically-labelled compounds can generally be prepared by conventional techniques known to those skilled in the art or by processes analogous to those described using an appropriate isotopically-labelled reagent in place of the non-labelled reagent previously employed.

The method of treatment or the formulation for use in the treatment of cancer, including lymphoma or leukaemia, may involve, in addition to the formulations of the invention, conventional surgery or radiotherapy or chemotherapy. Such chemotherapy may include the administration of one or more other active agents.

Where a further active agent is administered as part of a method of treatment of the invention, such combination treatment may be achieved by way of the simultaneous, sequential or separate dosing of the individual components of the treatment. Such combination products employ the compounds of this invention within a therapeutically effective dosage range described hereinbefore and the one or more other pharmaceutically-active agent(s) within its approved dosage range.

Thus, the pharmaceutical formulations of the invention may comprise another active agent.

The one or more other active agents may be one or more of the following categories of anti-tumour agents:
(i) antiproliferative/antineoplastic drugs and combinations thereof, such as alkylating agents (for example cyclophosphamide, nitrogen mustard, bendamustin, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, pemetrexed, cytosine arabinoside, and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, mitoxantrone and camptothecin);
(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;
(iii) anti-invasion agents, for example dasatinib and bosutinib (SKI-606), and metalloproteinase inhibitors, inhibitors of urokinase plasminogen activator receptor function or antibodies to Heparanase;
(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors;
(v) antiangiogenic agents such as those which inhibit the effects of vascular endothelial growth factor, [for example the anti-vascular endothelial cell growth factor antibody bevacizumab (Avastin™); thalidomide; lenalidomide; and for example, a VEGF receptor tyrosine kinase inhibitor such as vandetanib, vatalanib, sunitinib, axitinib and pazopanib;
(vi) gene therapy approaches, including for example approaches to replace aberrant genes such as aberrant p53 or aberrant BRCA1 or BRCA2;
(vii) immunotherapy approaches, including for example adoptive cell transfer, such as CAR T-cell therapy; antibody therapy such as alemtuzumab, rituximab, ibritumomab tiuxetan (Zevalin@) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); and toll-like receptor modulators for example TLR-7 or TLR-9 agonists;

(viii) cytotoxic agents for example fludarabine (fludara), cladribine, pentostatin (Nipent™);
(ix) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;
(x) targeted therapies, for example PI3Kd inhibitors, for example idelalisib and perifosine; or checkpoint inhibitor compounds including anti-PD-1, anti-PD-L1 and anti-CTLA4 molecules, such as nivolumab, pembrolizumab, pidilizumab, atezolizumab, durvalumab and avelumab.

The one or more other active agents may also be antibiotic.

Throughout the description and claims of this specification, the words "comprise" and "contain" and variations of them mean "including but not limited to", and they are not intended to (and do not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

EXAMPLES

Throughout the specification, these abbreviations have the following meanings.

| | |
|---|---|
| AcCN | acetonitrile |
| aq | aqueous |
| DCM | dichloromethane |
| DMSO | dimethylsulphoxide |
| $EC_{50}$ | Half maximal effective concentration |
| eq. | equivalents |
| HPLC | high pressure liquid chromatography |
| h | hours |
| $IC_{50}$ | half maximal inhibitory concentration |
| MS | mass spectrometry |
| NMR | nuclear magnetic resonance |
| Np | 1-naphthyl |
| rt | room temperature |
| TEA | triethylamine |
| TEAB | triethylammonium hydrogen carbonate buffer |
| TEP | triethyl phosphate |
| $t_R$ | retention time |

General Procedure for the Synthesis of Diphosphate Phosphoramidates

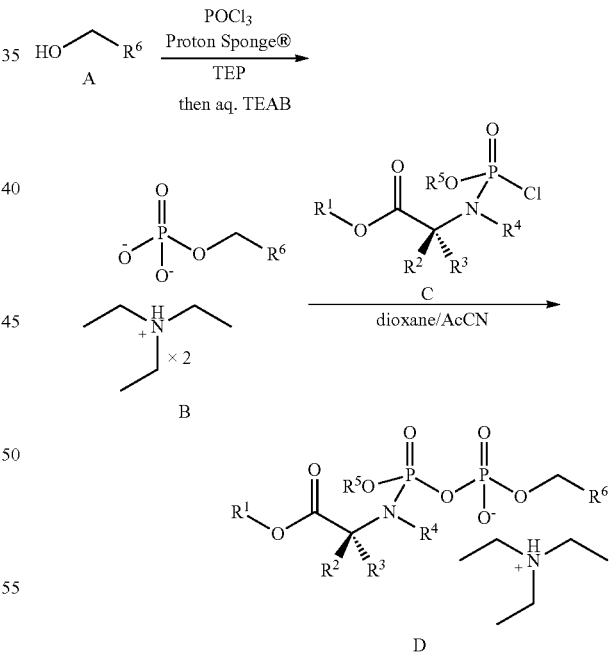

Dry nucleoside A (~1.0 mmol, 1.0 eq.) was dissolved in 5 mL of triethylphosphate (TEP) and stirred for 5 min at room temperature. The reaction mixture was cooled to 4° C. and dry 1,8-bis(dimethylamino)naphthalene (Proton Sponge®, 1.5 eq.) was added, followed by dropwise addition of $POCl_3$ (1.3 eq.). The resulting suspension was stirred at 4° C. for 2-3 hours. After this time, to the reaction mixture was added cold 0.5 M aq. triethylammonium hydrogen carbonate buffer (TEAB) (pH 7.5) and the resulting mixture was stirred for 30 minutes and then allowed to warm to room temperature and stirred for additional 1 h. TEP was extracted with tert-butylmethyl ether (4×50 mL), and aqueous solution was evaporated and dried under high vacuum overnight to yield the corresponding nucleoside 5'-monophosphate triethylammonium salt B as glassy colourless oil or white powder, which was used in the next step without further purification. The formation of the nucleoside 5'-monophosphate was confirmed by negative ion mass spectrometry.

A 0.5 M solution of TEAB was prepared by bubbling $CO_2$ through a 0.5 M triethylamine (TEA) solution in water at 0-4° C. for 30-45 min (pH of approximately 7.4-7.6, unless stated otherwise)

A synthesis of nucleoside 5'-monophosphate triethylammonium salt in the first step was accomplished following modified reference: El-Tayeb A. et al. *J. Med. Chem.* 2006, 49(24), 7076-7087.

A mixture of nucleoside 5'-monophosphate triethylammonium salt B (1 mmol) in 1:1 mixture of 1,4-dioxane/acetonitrile (20 mL) was stirred at room temperature (rt) under an argon atmosphere and an appropriate phosphorochloridate C (1.0 eq.) dissolved in anhydrous acetonitrile was added dropwise. The resulting reaction mixture was stirred for 18 h at rt. The crude mixture was evaporated under reduced pressure and the residue was re-dissolved in DCM and adsorbed on silica gel deactivated with TEA (3%) in a mixture of DCM/MeOH (92%/5%). Purification of crude materials (prepared for dry load) by automatic Biotage Isolera One on SNAP Ultra 50 g cartridge pre-primed with 3CV of TEA (3%) in a mixture of DCM/MeOH (92%/5%) with a gradient of MeOH in DCM (2% to 20%, flow 50 mL/min) afforded desired compounds, which were further re-purified on Biotage Isolera One (C18 SNAP Ultra 30 g cartridge with gradient of 0.1 M TEAB in AcCN (acetonitrile) from 100 to 0% as an eluent in 60 min., flow 15 mL/min.) or by HPLC on semi-preparative column (Varian Pursuit XRs 5C18, 150×21.22 mm) using gradient of 0.1 M TEAB in AcCN from 90/10 to 0/100 in 30 min.

Example 1: 2-Chloro-9-(2'-Deoxy-2'-fluoro-β-D-arabinofuranosyl)adenine-5'-O-[phenyl(benzoxy-L-alaninyl)] Diphosphate Triethylammonium Salt

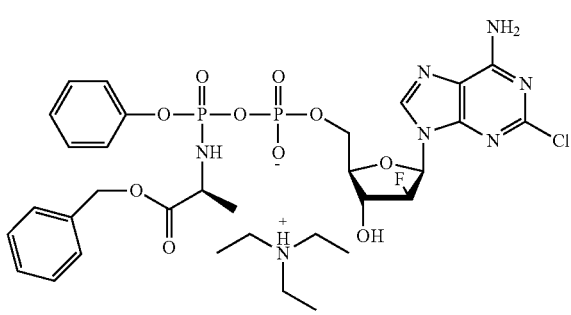

(1)

Prepared according to the general procedure from 2-chloro-9-(2'-deoxy-2'-fluoro-β-D-arabinofuranosyl)adenine-5'-monophosphate TEA salt (0.58 g, 0.98 mmol), phenyl(benzoxy-L-alaninyl)phosphorochloridate (0.35 g, 0.98 mmol) as a white foam (0.04 g, 6%).

$^{31}$P NMR (202 MHz, MeOD): $\delta_P$ −7.73 (d, J=21.0 Hz), −7.93 (d, J=21.2 Hz), −11.96 (d, J=18.4 Hz), −12.06 (d, J=20.8 Hz). $^1$H NMR (500 MHz, MeOD): $\delta_H$ 8.29, 8.28 (2×0.5H, H-8), 7.33-7.24 (9H, m, H—Ar), 7.18-7.14 (1H, m, H—Ar), 6.44, 6.41 (2×0.5H, 2×d, J=3.5 Hz, H-1'), 5.20-5.19 (0.5H, m, H-2'), 5.11 (2H, apparent s, OCH$_2$Ph), 5.10-5.08 (0.5H, m, H-2'), 4.58-4.54 (1H, m, H-3'), 4.26-4.24 (2H, m, 2×H-5'), 4.16-4.13 (2H, m, H-4', NHCHCH$_3$), 3.08 (6H, q, J=7.0 Hz, 3×CH$_2$CH$_3$), 1.39, 1.35 (3H, 2×d, J=7.0 Hz, NHCHCH$_3$), 1.26 (9H, t, J=7.0 Hz, 3×CH$_2$CH$_3$). MS (ES) negative mode m/z: 699 ([M+H]$^-$), Accurate mass: $C_{25}H_{28}ClFN_6O_{10}P_2$ required 700.93 found 699.20 ([M+H]$^-$). Reverse-phase HPLC, eluting with 0.1 M TEAB/AcCN from 90/10 to 0/100 in 30 min, F=1 mL/min, λ=254 nm, $t_R$=14.05 min.

Example 2: 2-Chloro-9-(2'-Deoxy-2'-fluoro-β-D-arabinofuranosyl)adenine-5'-O-[phenyl(ethoxy-L-alaninyl)] Diphosphate Triethylammonium Salt

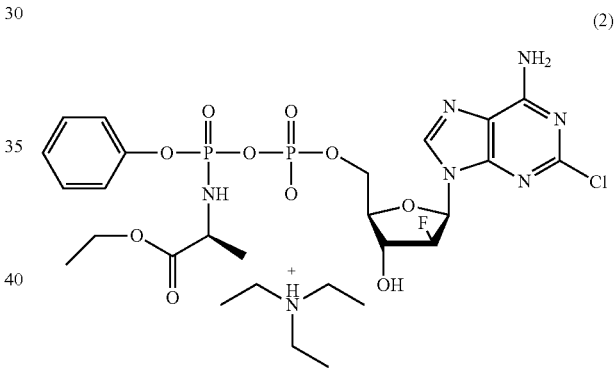

(2)

Prepared according to the general procedure from 2-chloro-9-(2'-deoxy-2'-fluoro-β-D-arabinofuranosyl)adenine-5'-monophosphate TEA salt (0.58 g, 0.98 mmol), phenyl (ethoxy-L-alaninyl)phosphorochloridate (0.28 g, 0.98 mmol) as a white solid (0.07 g, 10%). $^{31}$P NMR (202 MHz, MeOD): $\delta_P$ −7.72 (d, J=20.2 Hz), −7.89 (d, J=20.2 Hz), −11.94 (d, J=18.2 Hz), −12.10 (d, J=18.2 Hz). $^1$H NMR (500 MHz, MeOD): $\delta_H$ 8.29 (1H, s, H-8), 7.34-7.27 (4H, m, H—Ar), 7.17-7.15 (1H, m, H-Ar), 6.45, 6.42 (2×0.5H, 2× apparent t, J=1.5 Hz, H-1'), 5.24, 5.10 (2×0.5H, 2× apparent t, J=1.5 Hz, H-2'), 4.59, 4.55 (2×0.5H, 2× apparent t, J=2.0 Hz, H-3'), 4.26-4.24 (2H, m, OCH$_2$CH$_3$), 4.17-4.07 (4H, m, H-5', NHCHCH$_3$, H-4'), 3.05 (6H, q, J=7.0 Hz, 3×CH$_2$CH$_3$), 1.39, 1.34 (2×1.5H, 2×d, J=7.0 NHCHCH$_3$), 1.26-1.20 (12H, m, OCH$_2$CH$_3$, 3×CH$_2$CH$_3$). MS (ES) negative mode m/z: 637 ([M+H]$^-$), Accurate mass: $C_{21}H_{26}ClFN_6O_{10}P_2$ required 638.86 found 637.12 ([M+H]$^-$). Reverse-phase HPLC, eluting with H$_2$O/AcCN from 90/10 to 0/100 in 30 min, F=1 mL/min, λ=254 nm, two peaks for two diastereoisomers with $t_R$=14.20 min.

Example 3: 2-Chloro-9-(2'-Deoxy-2'-fluoro-β-D-arabinofuranosyl)adenine-5'-O-[phenyl(benzoxy-L-glycinyl)] Diphosphate Triethylammonium Salt

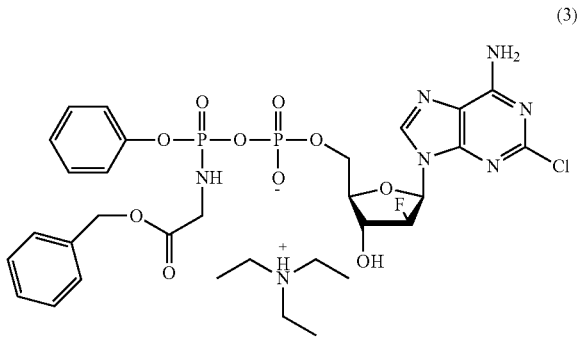

(3)

Prepared according to the general procedure from 2-chloro-9-(2'-deoxy-2'-fluoro-β-D-arabinofuranosyl)adenine-5'-monophosphate TEA salt (0.58 g, 0.98 mmol), phenyl (benzoxy-L-glycinyl)phosphorochloridate (0.335 g, 0.98 mmol) as a white solid (0.10 g, 13%).

$^{31}$P NMR (202 MHz, MeOD): $\delta_P$ −6.70 (d, J=20.2 Hz), −11.86 (d, J=22.2 Hz). $^1$H NMR (500 MHz, MeOD): $\delta_H$ 8.30, 8.29 (2×0.5H, 2×d, J=2.0 Hz, H-8), 7.36-7.28 (9H, m, H-Ar), 7.18-7.14 (1H, m, H-Ar), 6.44, 6.41 (2×0.5H, 2×d, J=4.5 Hz, H-1'), 5.20-5.18 (0.5H, m, H-2'), 5.16 (2H, apparent s, OCH$_2$Ph), 5.09-5.07 (0.5H, m, H-2'), 4.61-4.55 (1H, m, H-3'), 4.29-4.25 (2H, m, 2×H-5'), 4.17-4.13 (1H, m, H-4'), 3.96-3.84 (2H, m, NHCH$_2$), 2.89 (6H, q, J=7.0 Hz, 3×CH$_2$CH$_3$), 1.19 (9H, t, J=7.0 Hz, 3×CH$_2$CH$_3$). MS (ES) negative mode m/z: 685 ([M+H]$^−$), Accurate mass: C$_{25}$H$_{26}$ClFN$_6$O$_{10}$P$_2$ required 686 found 685.119 ([M+H]$^−$). Reverse-phase HPLC, eluting with 0.1 M TEAB/AcCN from 90/10 to 0/100 in 30 min, F=1 mL/min, λ=254 nm, $t_R$=13.6 min.

Example 4: 5-Fluoro-2'-deoxyuridine-5'-O-[1-naphthyl-(benzoxy-L-alaninyl)] Diphosphate Triethylammonium Salt

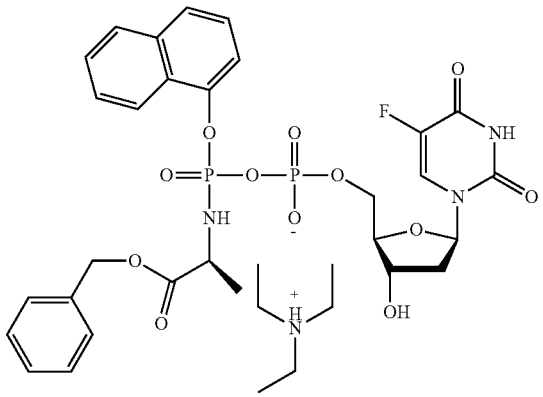

(4)

Prepared according to the general procedure from 5-fluoro-2'-deoxyuridine-5'-monophosphate TEA salt (1.07 g, 2.03 mmol), 1-naphthyl(benzoxy-L-alaninyl)phosphorochloridate (0.82 g, 2.03 mmol) as a white solid (0.16 g, 10%).

$^{31}$P NMR (202 MHz, MeOD): $\delta_P$ −7.43 (d, J=22.2 Hz), −7.79 (d, J=22.2 Hz), −11.89 (d, J=20.2 Hz), −12.02 (d, J=20.2 Hz). $^1$H-NMR (MeOD, 500 MHz) $\delta_H$ 8.39-8.35 (1H, m, H-Ar), 7.99 (1H, apparent t, J=6.0 Hz, H-Ar), 7.87-7.86 (1H, m, H-Ar), 7.69 (1H, t, J=7.0 Hz, H-Ar), 7.58 (1H, apparent d, J=7.0 Hz, H-Ar), 7.53-7.51 (2H, m, H—Ar, H-6), 7.43-7.36 (1H, m, H-Ar), 7.29-7.26 (5H, m, H-Ar), 6.26 (1H, apparent q, J=6.5 Hz, H-1'), 5.02-4.94 (2H, 2× apparent d, J=13.5, J=12.5 Hz, OCH$_2$Ph), 4.46-4.43 (1H, m, H-3'), 4.24-4.16 (3H, m, 3H, 2×H-5', NHCHCH$_3$), 4.03 (1H, apparent s, H-4'), 3.09 (6H, q, J=7.0 Hz, 3×CH$_2$CH$_3$), 2.22-2.19 (1H, m, H-2'), 2.16-2.4 (1H, m, H-2'), 1.37 (1.5H, d, J=7.0 Hz, NHCHCH$_3$), 1.29 (1.5H, d, J=7.0 Hz, NHCHCH$_3$), 1.26 (9H, t, J=7.0 Hz, 3×CH$_2$CH$_3$). MS (ES) negative mode m/z: 692 ([M+H]$^−$), Accurate mass: C$_{29}$H$_{30}$FN$_3$O$_{12}$P$_2$ required 693 found 692.128 ([M+H]$^−$). Reverse-phase HPLC, eluting with 0.1 M TEAB/AcCN from 90/10 to 0/100 in 30 min, F=1 mL/min, λ=254 nm, $t_R$=14.24 min., 14.34 min.

Example 5: 8-Chloroadenosine-5'-O-[1-naphthyl-(benzoxy-L-alaninyl)]diphosphate Triethylammonium Salt

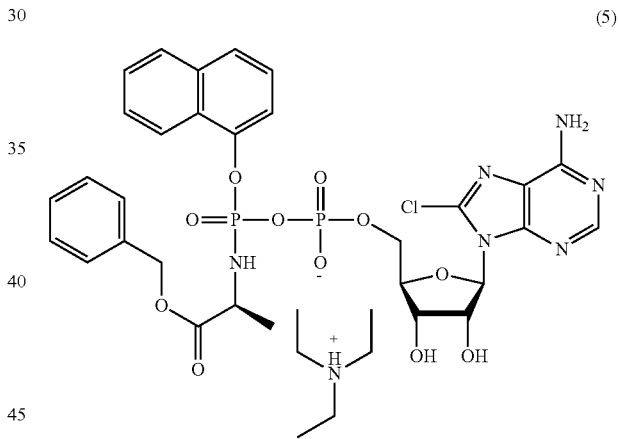

(5)

Prepared according to the general procedure from 8-chloroadenosine-5'-monophosphate TEA salt (0.46 g, 0.795 mmol), 1-naphthyl(benzoxy-L-alaninyl)phosphorochloridate (0.32 g, 0.795 mmol) after two re-purifications on Biotage Isolera One (C18 30 g cartridge) and HPLC (semi-preparative C18 column) as a white solid (0.02 g, 4%).

$^{31}$P NMR (202 MHz, MeOD): $\delta_P$ −7.58 (d, J=22.2 Hz), −8.0 (d, J=20.2 Hz), −11.85 (d, J=22.2 Hz), −12.05 (d, J=20.2 Hz). $^1$H NMR (500 MHz, CD$_3$OD): $\delta_H$ 8.36-8.33 (1H, m, H-Ar), 8.14, 8.10 (2×0.5H, 2×s, H-2), 7.86-7.84 (1H, m, H-Ar), 7.66 (1H, d, J=8.0 Hz, H-Ar), 7.56-7.45 (3H, m, H-Ar), 7.38-7.33 (1H, m, H-Ar), 7.29-7.24 (5H, m, H-Ar), 6.02 (1H, t, J=6.0 Hz, H-1'), 5.35-5.32 (1H, m, H-2'), 5.00, 4.98, 4.97, 4.94 (2H, AB, J$_{AB}$=12.3 Hz, OCH$_2$Ph), 4.54-4.50 (1H, m, H-3'), 4.40-4.33 (1H, m, H-5'), 4.26-4.13 (3H, m, H-5', H-4', NHCHCH$_3$), 3.06 (6H, q, J=7.0 Hz, 3×CH$_2$CH$_3$), 1.36 (1.5H, d, J=7.0 Hz, NHCHCH$_3$), 1.26 (1.5H, d, J=7.0 Hz, NHCHCH$_3$), 1.25 (9H, t, J=7.0 Hz, 3×CH$_2$CH$_3$). MS (ES) negative mode m/z: 747 ([M+H]$^−$), Accurate mass: C$_3$H$_{31}$ClN$_6$O$_{11}$P$_2$ required 749 found 747.1102 ([M+H]⁻). Reverse-phase HPLC, eluting with 0.1 M TEAB/AcCN from 90/10 to 0/100 in 30 min, F=1 mL/min, λ=254 nm, $t_R$=14.32, 14.48 min.

Examples 6 and 7: 3'-Deoxyadenosine-5'-O-[phenyl (benzoxy-L-alaninyl)] Diphosphate Triethylammonium Salt (6) and 3'-Deoxyadenosine-5',2'-Bis-O-[phenyl(benzoxy-L-alaninyl)]-diphosphate Triethylammonium Salt (7)

Prepared according to the general procedure from 3'-deoxyadenosine-5'-monophosphate TEA salt (0.63 g, 1.186 mmol), phenyl(benzoxy-L-alaninyl)phosphorochloridate (0.42 g, 1.186 mmol). Two products were isolated: 3'-deoxyadenosine-5',2'-O-[phenyl(benzoxy-L-alaninyl)]diphosphate triethylammonium salt (0.05 g, 5%) and 3'-deoxyadenosine-5'-O-[phenyl(benzoxy-L-alaninyl)] diphosphate as a colorless film (0.01 g, 1.3%).

(7)

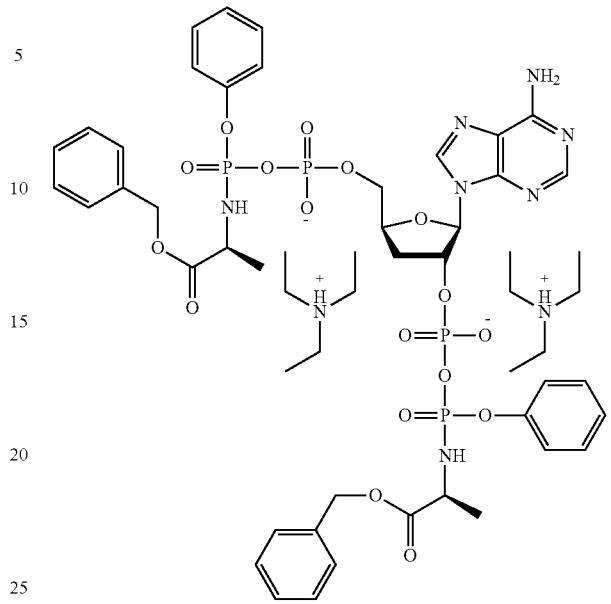

(6)

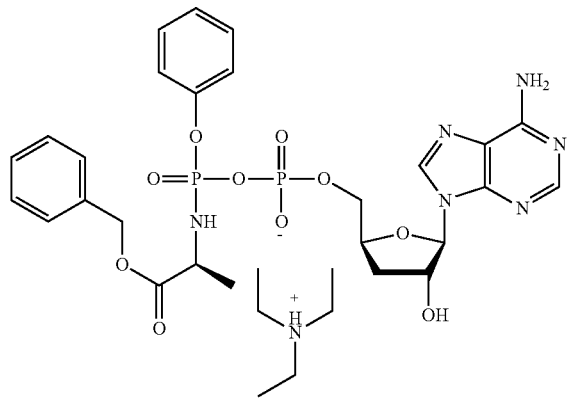

$^{31}$P NMR (202 MHz, MeOD): $\delta_P$ -7.76 (d, J=21.0 Hz), -8.03 (d, J=21.8 Hz), -11.70 (d, J=20.4 Hz), -11.81 (d, J=16.76 Hz). $^1$H NMR (500 MHz, CD$_3$OD): $\delta_H$ 8.45 (1H, s, H-8), 8.21 (1H, s, H-2), 7.34-7.23 (9H, m, H-Ar), 7.14-7.11 (1H, m, H-Ar), 6.02 (1H, apparent s, H-1'), 5.10 (2H, AB system apparent t, $J_{AB}$=16.5 Hz, OCH$_2$Ph), 4.66-4.60 (2H, m, H-2', H-4'), 4.29-4.27 (1H, m, H-5'), 4.19-4.13 (2H, m, H-5', NHCHCH$_3$), 3.06 (6H, q, J=7.0 Hz, 3×CH$_2$CH$_3$), 2.42-2.33 (1H, m, H-3'), 2.11-2.06 (1H, m, H-3'), 1.40 (1.5H, d, J=7.0 Hz, NHCHCH$_3$), 1.35 (1.5H, d, J=7.0 Hz, NHCHCH$_3$), 1.25 (9H, t, J=7.0 Hz, 3×CH$_2$CH$_3$). MS (ES) negative mode m/z: 647 ([M+H]⁻), Accurate mass: C$_{26}$H$_{30}$N$_6$O$_{10}$P$_2$ required 648 found 647.154 ([M+H]⁻). Reverse-phase HPLC, eluting with 0.1 M TEAB/AcCN from 90/10 to 0/100 in 20 min, F=1 mL/min, λ=254 nm, $t_R$=8.20 min.

$^{31}$P NMR (202 MHz, MeOD): $\delta_P$ -7.78 (d, J=20.4 Hz), -7.84 (d, J=22.08 Hz), -8.01 (d, J=21.0 Hz), -12.08 (d, J=21.6 Hz), -12.18 (d, J=22.0 Hz), -13.50 (d, J=20.6 Hz), -13.56 (d, J=20.2 Hz). $^1$H NMR (500 MHz, CD$_3$OD): $\delta_H$ 8.20 (0.5H, s, H-8), 8.19 (0.5H, s, H-8), 8.04 (1H, s, H-2), 7.21-7.19 (12H, m, H-Ar), 7.14-6.97 (8H, m, H-Ar), 6.16 (0.5H, s, H-1'), 6.15 (0.5H, s, H-1'), 5.27 (0.5H, apparent t, J=7.0 Hz, H-2'), 5.15 (0.5H, apparent t, J=5.0 Hz, H-2'), 5.0-4.94 (4H, m, 2×OCH$_2$Ph), 4.48-4.60 (1H, m, H-4'), 4.13-4.08 (1H, m, H-5'), 4.05-3.95 (3H, m, H-5', 2×NHCHCH$_3$), 3.06 (12H, q, J=7.0 Hz, 3×CH$_2$CH$_3$), 2.50-2.42 (1H, m, H-3'), 2.27-2.20 (1H, m, H-3'), 1.26-1.17 (6H, m, 2×NHCHCH$_3$), 1.25 (18H, t, J=7.0 Hz, 3×CH$_2$CH$_3$). MS (ES) negative mode m/z: 1044 ([M+H]⁻), Accurate mass: C$_{42}$H$_{47}$N$_7$O$_{17}$P$_4$ required 1045 found 1044.232 ([M+H]⁻). Reverse-phase HPLC, eluting with 0.1 M TEAB/AcCN from 90/10 to 0/100 in 30 min, F=1 mL/min, λ=254 nm, $t_R$=9.75 min, 10.37 min.

Example 8: 2'-Deoxy-2',2'-difluoro-D-cytidine-5'-O-[phenyl(benzoxy-L-alaninyl)] Diphosphate Triethylammonium Salt (8)

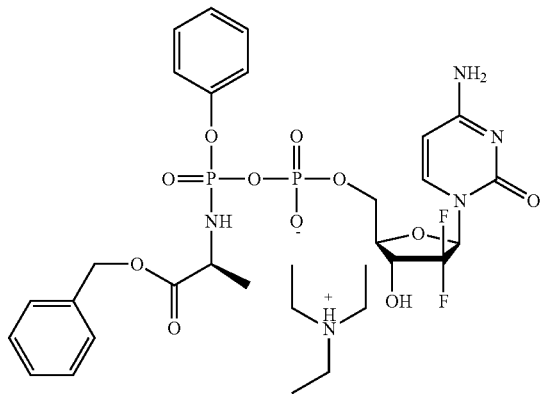

Prepared according to the general procedure from 2'-deoxy-2',2'-difluoro-D-cytidine 5'-monophosphate TEA salt (0.62 g, 1.13 mmol), phenyl(benzoxy-L-alaninyl)phosphorochloridate (0.40 g, 1.13 mmol) as a white solid (0.05 g, 6%). $^{31}$P NMR (202 MHz, MeOD): $\delta_P$ −7.65 (d, J=21.0 Hz), −7.87 (d, J=21.0 Hz), −12.12 (d, J=16.9 Hz), −12.21 (d, J=21.4 Hz). $^1$H NMR (500 MHz, MeOD): $\delta_H$ 7.83 (1H, d, J=7.5 Hz, H-6), 7.35-7.25 (9H, m, H-Ar), 7.16 (1H, apparent t, J=7.0 Hz, H-Ar), 6.27-6.24 (1H, m, H-1'), 5.96, 5.95 (1H, 2×d, J=5.0 Hz, H-5), 5.13 (2H, AB system, apparent s, OCH$_2$Ph), 4.37-4.25 (3H, m, 2×H-5', H-3'), 4.18-4.12 (1H, m, H-4'), 4.00-3.97 (1H, m, NHCHCH$_3$), 3.20 (6H, q, J=7.0 Hz, 3×CH$_2$CH$_3$), 1.40, 1.35 (3H, 2×d, J=7.5 Hz, NHCHCH$_3$), 1.31 (9H, t, J=7.5 Hz, 3×CH$_2$CH$_3$). MS (ES) negative mode m/z: 659 ([M+H]$^-$), Accurate mass: C$_{25}$H$_{28}$F$_2$N$_4$O$_{11}$P$_4$ required 660 found 659 ([M+H]$^-$). Reverse-phase HPLC, eluting with 0.1 M TEAB/AcCN from 90/10 to 0/100 in 30 min, F=1 mL/min, $\lambda$=254 nm, $t_R$=12.55 min, 12.85 min.

Example 9: 2-Chloro-9-(2'-Deoxy-2'-fluoro-β-D-arabinofuranosyl)adenine-5'-O-[phenyl(neopentoxy-L-alaninyl)] Diphosphate Triethylammonium Salt (9)

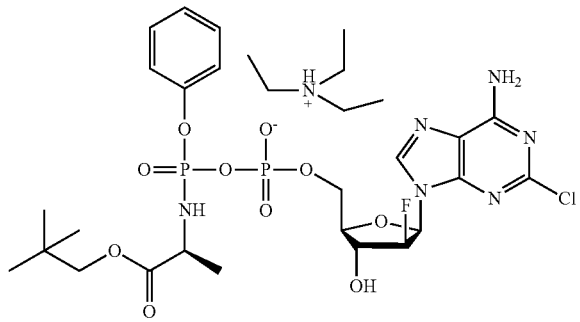

Prepared according to the general procedure from 2-chloro-9-(2'-deoxy-2'-fluoro-β-D-arabinofuranosyl)adenine-5'-monophosphate TEA salt (0.77 g, 1.32 mmol), phenyl (neopentoxy-L-alaninyl)phosphorochloridate (0.43 g, 1.32 mmol) and TEA (0.53 mL, 3.81 mmol) as a white solid (0.065 g, 6%).

$^{31}$P NMR (202 MHz, CD$_3$OD): $\delta_P$ −7.67 (d, J=21.0 Hz), −7.93 (d, J=21.0 Hz), −11.93 (d, J=21.21 Hz), −12.04 (d, J=21.21 Hz).

$^1$H NMR (500 MHz, CD$_3$OD): $\delta_H$ 8.18 (0.5H, s, H-8), 8.17 (0.5H, s, H-8), 7.22-7.15 (4H, m, H-Ar), 7.12-7.09 (1H, m, H-Ar), 6.33 (0.5H, t, J=1.5 Hz, H-1'), 6.30 (0.5H, t, J=1.5 Hz, H-1'), 5.08 (0.5H, apparent t, J=1.5 Hz, H-2'), 4.96 (0.5H, apparent t, J=1.5 Hz, H-2'), 4.46 (0.5H, apparent t, J=2.0 Hz, H-3'), 4.43 (0.5H, apparent t, J=2.0 Hz, H-3'), 4.15-4.11 (2H, m, H-5'), 4.05-3.99 (2H, m, NHCHCH$_3$, H-4'), 3.72, 3.69, 3.63, 3.61 (2H, AB system, J=10.50 Hz, OCH$_2$C(CH$_3$)$_3$), 3.05 (6H, q, J=7.0 Hz, N(CH$_2$CH$_3$)$_3$), 1.31, 1.25 (2×1.5H, 2×d, J=7.0 NHCHCH$_3$), 1.31 (9H, t, J=7.5 Hz, N(CH$_2$CH$_3$)$_3$), 0.80 (9H, s, OCH$_2$C(CH$_3$)$_3$).

$^{13}$C NMR (125 MHz, CD$_3$OD): $\delta_C$ 175.10 (d, $^3J_{C-P}$=6.4 Hz, C=O, ester), 173.56 (d, $^3J_{C-P}$=6.4 Hz, C=O, ester), 156.72 (C-6), 154.16 (C-2), 153.42 (d, $^2J_{C-P}$=3.8 Hz, C-Ar), 150.90 (d, $^2J_{C-P}$=5.8 Hz, C-Ar), 150.26 (C-4), 142.68 (C-8), 129.26, 128.73, 124.65, 124.60, 122.40 (CH—Ar), 120.38, 120.15 (2×d, $^3J_{C-P}$=4.6 Hz, CH-Ar), 117.15 (C-5), 94.99 (d, $^1J_{C-F}$=191.4 Hz, C-2'), 82.92 (d, $^3J_{C-F}$=8.25 Hz, C-4'), 82.78 (d, $^2J_{C-F}$=8.5 Hz, C-1'), 73.96, 73.66 (OCH$_2$C(CH$_3$)$_3$), 73.61 (d, $^2J_{C-F}$=24.5 Hz, C-3'), 65.05 (C-5'), 50.59, 50.29 (NHCHCH$_3$), 46.26 (N(CH$_2$CH$_3$)$_3$), 30.91 (OCH$_2$C(CH$_3$)$_3$), 25.36 (OCH$_2$C(CH$_3$)$_3$), 19.75, 19.63 (2×d, $^3J_{C-P}$=5.4 Hz, NHCHCH$_3$), 7.84 (N(CH$_2$CH$_3$)$_3$).

C$_{24}$H$_{32}$ClFN$_6$O$_{10}$P$_2$ mass required m/z 680.94; found MS (ES$^-$) m/z: 679.19 ([M+H]$^-$).

Reverse-phase HPLC, eluting with 0.1 M TEAB/AcCN from 90/10 to 0/100 in 30 min, F=1 mL/min, $\lambda$=254 nm, one peak for two diastereoisomers with $t_R$=15.83 min.

Example 10: 2-Chloro-9-(2'-Deoxy-2'-fluoro-β-D-arabinofuranosyl)adenine-5'-O-[phenyl(benzoxy-dimethylglycinyl)] Diphosphate Triethylammonium Salt (10)

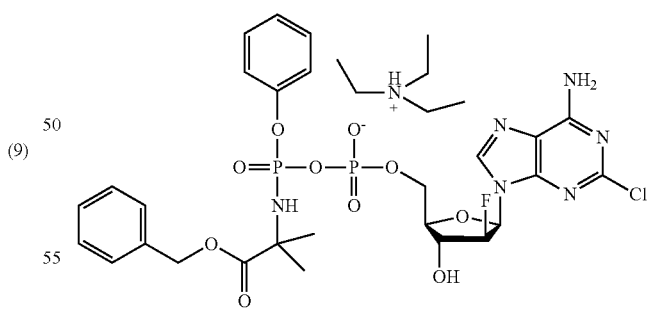

Prepared according to the general procedure from 2-chloro-9-(2'-deoxy-2'-fluoro-β-D-arabinofuranosyl)adenine-5'-monophosphate TEA salt (0.96 g, 1.64 mmol), phenyl (benzoxy-dimethylglycinyl)phosphorochloridate (0.60 g, 1.64 mmol) and TEA (0.66 mL, 4.75 mmol) as a white solid (0.085 g, 6%).

$^{31}$P NMR (202 MHz, CD$_3$OD): $\delta_P$ −9.79 (d, J=22.6 Hz), −9.82 (d, J=22.6 Hz), −12.17 (d, J=21.20 Hz), −12.20 (d, J=21.0 Hz).

¹H NMR (500 MHz, CD₃OD): δ_H 8.29 (0.5H, s, H-8), 8.27 (0.5H, s, H-8), 7.36-7.26 (9H, m, H-Ar), 7.16-7.13 (1H, m, H-Ar), 6.43 (0.5H, d, J=1.5 Hz, H-1'), 6.39 (0.5H, d, J=1.5 Hz, H-1'), 5.20-5.17 (0.5H, m, H-2'), 5.15-5.13 (2H, m, OCH₂Ph), 5.11-5.07 (0.5H, m, H-2'), 4.60-4.52 (1H, m, H-3'), 4.26-4.23 (2H, m, H-5'), 4.15-4.11 (1H, m, H-4'), 3.05 (6H, q, J=7.0 Hz, N(CH₂CH₃)₃), 1.54 (6H, s, NHC(CH₃)₂), 1.31 (9H, t, J=7.5 Hz, N(CH₂CH₃)₃).

¹³C NMR (125 MHz, CD₃OD): δ_C 174.96 (d, ³J_{C–P}=6.6 Hz, C=O, ester), 156.69 (C-6), 154.13 (C-2), 151.06 (d, ²J_{C–P}=7.3 Hz, C-Ar), 150.22 (C-4), 140.21 (C-8), 136.04 (C-Ar), 129.15. 128.12. 127.76, 127.68, 124.48, 120.47, 120.43 (CH-Ar), 117.12 (C-5), 95.49 (d, ¹J_{C–F}=192.5 Hz, C-2'), 82.84 (d, ³J_{C–F}=3.6 Hz, C-4'), 82.68 (d, ²J_{C–F}=11.5 Hz, C-1'), 73.59 (d, ²J_{C–F}=11.5 Hz, C-3'), 73.41 (d, ²J_{C–F}=10.5 Hz, C-3'), 66.74 (OCH₂Ph), 64.90 (C-5'), 48.47 (NHC(CH₃)₂), 46.35 (N(CH₂CH₃)₃), 26.14, 26.12 (NHC(CH₃)₂, 9.85 (N(CH₂CH₃)₃).

C₂₇H₃₀ClFN₆O₁₀P₂ mass required m/z 714.96; found MS (ES⁻) m/z: 713.13 ([M+H]⁻).

Reverse-phase HPLC, eluting with 0.1 M TEAB/AcCN from 90/10 to 0/100 in 30 min, F=1 mL/min, λ=254 nm, one peak for two diastereoisomers with t_R=14.51 min.

Example 11: 2-Chloro-9-(2'-Deoxy-2'-fluoro-β-D-arabinofuranosyl)adenine-5'-O-[1-naphthyl(benzoxy-dimethylglycinyl)] Diphosphate Triethylammonium Salt (11)

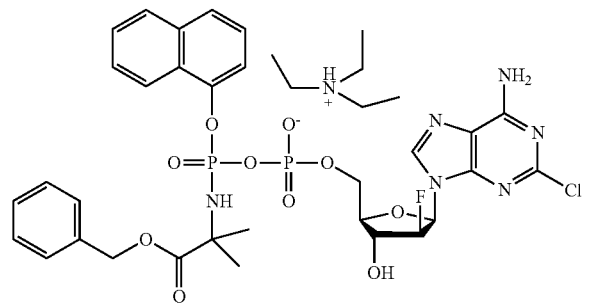

Prepared according to the general procedure from 2-chloro-9-(2'-deoxy-2'-fluoro-β-D-arabinofuranosyl)adenine-5'-monophosphate TEA salt (0.96 g, 1.64 mmol), 1-naphthyl(benzoxy-dimethylglycinyl)phosphorochloridate (0.68 g, 1.64 mmol) and TEA (0.66 mL, 4.75 mmol) as a white solid, which was further repurified by preparative HPLC (0.14 g, 10%).

³¹P NMR (202 MHz, CD₃OD): δ_P −9.79 (d, J=22.6 Hz), −9.82 (d, J=22.6 Hz), −12.17 (d, J=21.20 Hz), −12.20 (d, J=21.0 Hz).

¹H NMR (500 MHz, CD₃OD): δ_H 8.38-8.34 (2H, m, H-Ar), 8.24 (0.5H, d, ⁵J_{H–F}=2.0 Hz, H-8), 8.22 (0.5H, d, ⁵J_{H–F}=2.0 Hz, H-8), 7.85-7.83 (2H, m, H-Ar), 7.65-7.60 (3H, m, H-Ar), 7.48-7.44 (3H, m, H-Ar), 7.38-7.29 (2H, m, H-Ar), 6.39 (0.5H, t, J=1.5 Hz, H-1'), 6.36 (0.5H, t, J=1.5 Hz, H-1'), 5.17-5.15 (0.5H, m, H-2'), 5.14-5.07 (2H, m, OCH₂Ph), 5.05-5.02 (0.5H, m, H-2'), 4.57-4.50 (1H, m, H-3'), 4.27-4.24 (2H, m, H-5'), 4.15-4.10 (1H, m, H-4'), 3.05 (6H, q, J=7.0 Hz, N(CH₂CH₃)₃), 1.90 (6H, s, NHC(CH₃)₂), 1.31 (9H, t, J=7.5 Hz, N(CH₂CH₃)₃).

¹³C NMR (125 MHz, CD₃OD): δ_C 176.53, 174.95 (2×d, ³J_{C–P}=6.7 Hz, C=O, ester), 156.64 (C-6), 154.08 (C-2), 150.16, 149.36 (2×d, ³J_{C–P}=7.0 Hz, C-Ar), 146.91, 146.85 (C-4), 142.89 (C-8), 136.23, 135.99, 134.79 (C-Ar), 128.07, 127.70, 127.65, 127.61, 127.16, 126.99, 126.18, 125.83, 125.59, 125.43, 125.06, 124.76, 124.20, 122.57, 122.25, 122.20, 121.44 (CH-Ar), 117.07 (C-5), 115.9 (d, ⁴J_{C–P}=3.2 Hz, CH-Ar), 113.15 (d, ⁴J_{C–P}=3.2 Hz, CH-Ar), 94.98, 94.95 (2×d, ¹J_{C–F}=191.5 Hz, C-2'), 82.80 (d, ³J_{C–F}=3.8 Hz C-4'), 82.68 (d, ²J_{C–F}=24.5 Hz C-1'), 73.57, 73.45 (2×d, ²J_{C–F}=24.5 Hz, C-3'), 66.69, 66.37 (OCH₂Ph), 64.94 (C-5'), 56.95, 55.87 (NHC(CH₃)₂), 46.28 (N(CH₂CH₃)₃), 26.10 (d, ³J_{C–P}=4.1 Hz, NHC(CH₃)₂), 7.86 (N(CH₂CH₃)₃).

C₃₁H₃₂ClFN₆O₁₀P₂ mass required m/z 764.13; found MS (ES⁻) m/z: 763.15 ([M+H]⁻).

Reverse-phase HPLC, eluting with 0.1 M TEAB/AcCN from 90/10 to 0/100 in 30 min, F=1 mL/min, λ=254 nm, one peak for two diastereoisomers with t_R=14.85 min.

Example 12: 2-Chloro-9-(2'-Deoxy-2'-fluoro-β-D-arabinofuranosyl)adenine-5'-O-[phenyl(cyclohexoxy-L-valinyl)] Diphosphate Triethylammonium Salt (12)

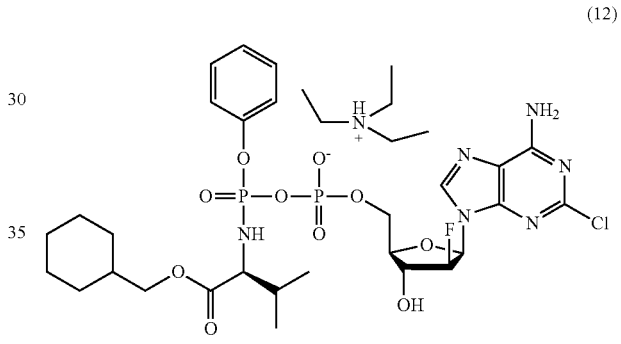

Prepared according to the general procedure from 2-chloro-9-(2'-deoxy-2'-fluoro-β-D-arabinofuranosyl)adenine-5'-monophosphate TEA salt (0.96 g, 1.64 mmol), phenyl(cyclohexoxy-L-valinyl)phosphorochloridate (0.61 g, 1.64 mmol) and TEA (0.66 mL, 4.75 mmol) as a white solid (0.19 g, 14%).

³¹P NMR (202 MHz, CD₃OD): δ_P −6.74 (d, J=21.2 Hz), −6.78 (d, J=21.0 Hz), −12.0 (d, J=21.4 Hz).

¹H NMR (500 MHz, CD₃OD): δ_H 8.18 (0.5H, d, ⁵J_{H–F}=1.0 Hz, H-8), 8.17 (0.5H, d, ⁵J_{H–F}=1.0 Hz, H-8), 7.22-7.15 (4H, m, H-Ar), 7.01-6.98 (1H, m, H-Ar), 6.34 (0.5H, t, J=1.5 Hz, H-1'), 6.30 (0.5H, t, J=1.5 Hz, H-1'), 5.08-5.06 (0.5H, m, H-2'), 4.97-4.96 (0.5H, m, H-2'), 4.62-4.54 (1H, m, OCH), 4.46 (0.5H, apparent t, J=2.0 Hz, H-3'), 4.43 (0.5H, apparent t, J=2.0 Hz, H-3'), 4.15-4.12 (2H, m, H-5'), 4.06-4.02 (1H, m, H-4'), 3.68 (0.5H, apparent dd, J=10.0 Hz, J=5.5 Hz, NHCHCH(CH₃)₂), 3.64 (0.5H, apparent dd, J=10.0 Hz, J=5.5 Hz, NHCHCH(CH₃)₂), 3.05 (6H, q, J=7.0 Hz, N(CH₂CH₃)₃), 1.91-1.80 (1H, m, NHCHCH (CH₃)₂), 1.67-1.58 (5H, m, CH₂), 1.39-1.37 (1H, m, CH₂), 1.36-1.31 (3H, m, CH₂), 1.31 (9H, t, J=7.5 Hz, N(CH₂CH₃)₃), 0.86-0.78 (6H, m, NHCHCH(CH₃)₂).

¹³C NMR (125 MHz, CD₃OD): δ_C 171.98, 171.95 (2×d, ³J_{C–P}=4.5 Hz, C=O, ester), 156.69 (C-6), 154.14 (C-2), 151.02 (d, ²J_{C–P}=3.8 Hz, C-Ar), 150.23 (C-4), 142.25 (C-8), 129.16, 128.60, 124.56, 124.47, 120.44 (CH-Ar), 117.13 (C-5), 94.96 (d, ¹J_{C–F}=191.4 Hz, C-2'), 82.90 (d, $^3J_{C-F}$=3.8 Hz C-4'), 82.81 (d, $^2J_{C-F}$=32.5 Hz C-1'), 73.59, (d, $^2J_{C-F}$=24.5 Hz, C-3'), 73.42 (d, $^2J_{C-F}$=16.8 Hz, C-3'), 62.88 (d, $^2J_{C-P}$=7.5 Hz, C—C-5'), 60.45, 60.20 (NHCHCH (CH$_3$)$_2$), 46.42 (N(CH$_2$CH$_3$)$_3$), 32.56, 32.09 (NHCHCH (CH$_3$)$_2$), 31.14 (CH$_2$), 25.00 (CH$_2$), 23.25 (CH$_2$), 17.79, 16.76 (NHCHCHCH$_3$), 7.82 (N(CH$_2$CH$_3$)$_3$).

C$_{27}$H$_{36}$ClFN$_6$O$_{10}$P$_2$ mass required m/z 720.16; found MS (ES$^-$) m/z: 719.17 ([M+H]$^-$).

Reverse-phase HPLC, eluting with 0.1 M TEAB/AcCN from 90/10 to 0/100 in 30 min, F=1 mL/min, λ=254 nm, one peak for two diastereoisomers with t$_R$=15.73 min.

Example 13: 2-Chloro-9-(2'-Deoxy-2'-fluoro-β-D-arabinofuranosyl)adenine-5'-O-[1-naphthyl(neopentoxy-L-alaninyl)] Diphosphate Triethylammonium Salt (13)

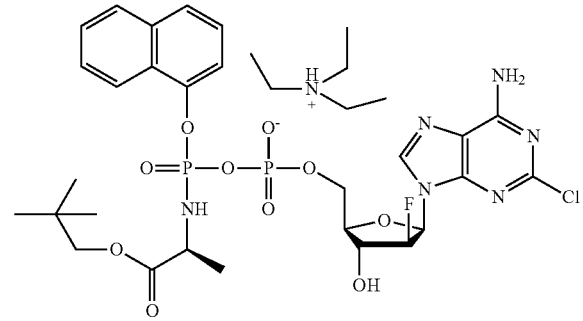

Prepared according to the general procedure from 2-chloro-9-(2'-deoxy-2'-fluoro-β-D-arabinofuranosyl)adenine-5'-monophosphate TEA salt (0.57 g, 0.97 mmol), 1-naphthyl(neopentoxy-L-alaninyl)phosphorochloridate (0.37 g, 0.97 mmol) and TEA (0.39 mL, 2.86 mmol) as a white solid (0.13 g, 16%).

$^{31}$P NMR (202 MHz, CD$_3$OD): δ$_P$ −7.41 (d, J=23.5 Hz), −7.82 (d, J=22.5 Hz), −11.82 (d, J=22.69 Hz), −11.95 (d, J=21.80 Hz).

$^1$H NMR (500 MHz, CD$_3$OD): δ$_H$ 8.36-8.25 (2H, m, H-Ar), 7.85-7.79 (2H, m, H-Ar), 7.68-7.65 (2H, m, H-8), 7.58-7.36 (2H, m, H-Ar), (6H, m, H-Ar), 6.4 (1H, dd J=16.68 Hz, 4.1 Hz, H-1'), 5.19-5.05 (1H, m, H-2'), 4.58-4.53 (1H m, H-3'), 4.29-4.25 (2H, m, H-5'), 4.17-4.14 (1.5H, m, H-4' and NHCHCH$_3$), 4.06-4.01 (0.5H, m, NHCHCH$_3$), 3.75-3.66 (2H, m, OCH$_2$C(CH$_3$)$_3$), 3.14 (6H, q, J=7.0 Hz, N(CH$_2$CH$_3$)$_3$), 1.31-1.26 (12H, m, NHCHCH$_3$, N(CH$_2$CH$_3$)$_3$).

C$_{28}$H$_{34}$ClFN$_6$O$_{10}$P$_2$ mass required m/z 730.15; found MS (ES$^-$) m/z: 729.09 ([M+H]$^-$).

Reverse-phase HPLC, eluting with 0.1 M TEAB (pH 7.2)/AcCN from 90/10 to 0/100 in 30 min, F=1 mL/min, λ=254 nm, one peak for two diastereoisomers with t$_R$=14.63 min.

Example 14: 2-Chloro-9-(2'-Deoxy-2'-fluoro-β-D-arabinofuranosyl)adenine-5'-O-[phenyl(neopentoxy-D-alaninyl)] Diphosphate Triethylammonium Salt (14)

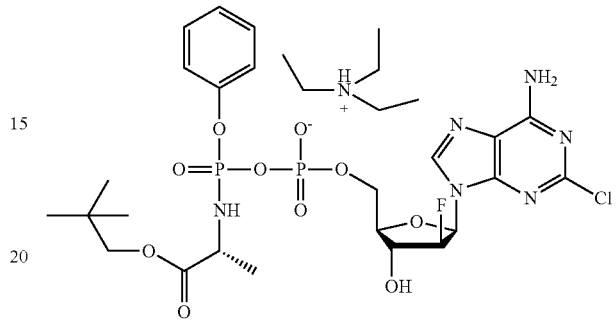

Prepared according to the general procedure from 2-chloro-9-(2'-deoxy-2'-fluoro-β-D-arabinofuranosyl)adenine-5'-monophosphate TEA salt (0.86 g, 1.48 mmol), phenyl(neopentoxy-D-alaninyl)phosphorochloridate (0.49 g, 1.48 mmol) and TEA (0.59 mL, 4.25 mmol) as a white solid (0.16 g, 14%).

$^{31}$P NMR (202 MHz, CD$_3$OD): δ$_P$ −7.68 (d, J=21.0 Hz), −7.91 (d, J=21.0 Hz), −12.04 (d, J=20.08 Hz), −12.14 (d, J=20.08 Hz).

$^1$H NMR (500 MHz, CD$_3$OD): δ$_H$ 8.30 (0.5H, d, J$_{H-F}$=2.0 Hz, H-8), 8.29 (0.5H, d, J$_{H-F}$=2.0 Hz, H-8), 7.35-7.27 (4H, m, H-Ar), 7.18-7.14 (1H, m, H-Ar), 6.45 (0.5H, t, J=3.5 Hz, H-1'), 6.42 (0.5H, t, J=3.5 Hz, H-1'), 5.20 (0.5H, apparent t, J=3.5 Hz, H-2'), 5.09 (0.5H, apparent t, J=3.5 Hz, H-2'), 4.61-4.54 (1H, m, H-3'), 4.27-4.23 (2H, m, H-5'), 4.17-4.10 (2H, m, NHCHCH$_3$, H-4'), 3.80-3.72 (2H, m, OCH$_2$C(CH$_3$)$_3$), 3.33 (6H, q, J=7.0 Hz, N(CH$_2$CH$_3$)$_3$), 1.42 (1.5H, dd, J=7.0 Hz, J=0.5 Hz, NHCHCH$_3$), 1.36 (1.5H, dd, J=7.0 Hz, J=0.5 Hz, NHCHCH$_3$), 1.31 (9H, t, J=7.5 Hz, N(CH$_2$CH$_3$)$_3$), 0.80 (9H, s, OCH$_2$C(CH$_3$)$_3$).

$^{13}$C NMR (125 MHz, CD$_3$OD): δ$_C$ 173.56, 173.48 (apparent t, $^3J_{C-P}$=7.6 Hz, C=O, ester), 156.70 (C-6), 154.13 (C-2), 150.89 (apparent t, $^2J_{C-P}$=6.6 Hz, C-Ar), 150.24 (C-4), 142.68 (C-8), 129.22, 128.67, 124.65, 124.60, 122.34 (CH-Ar), 120.38, 120.36 (2×d, $^3J_{C-P}$=4.6 Hz, CH-Ar), 117.14 (C-5), 95.0, 94.99 (2×d, $^1J_{C-F}$=191.6 Hz, C-2'), 82.76 (d, $^3J_{C-F}$=8.25 Hz, C-4'), 82.68 (d, $^2J_{C-F}$=8.5 Hz, C-1'), 73.95, 73.92 (OCH$_2$C(CH$_3$)$_3$), 73.58, 73.50 (2×d, $^2J_{C-F}$=24.5 Hz, C-3'), 64.98, 64.86 (2×d, $^2J_{C-P}$=4.6 Hz, C-5'), 50.36, 50.27 (2×d, $^3J_{C-P}$=2.4 Hz, NHCHCH$_3$), 46.36 (N(CH$_2$CH$_3$)$_3$), 30.92, 30.89 (OCH$_2$C(CH$_3$)$_3$), 25.35, 25.33 (OCH$_2$C(CH$_3$)$_3$), 19.75, 19.61 (2×d, $^3J_{C-P}$=5.6 Hz, NHCHCH$_3$), 7.82 (N(CH$_2$CH$_3$)$_3$).

C$_{24}$H$_{32}$ClFN$_6$O$_{10}$P$_2$ mass required m/z 680.94; found MS (ES$^-$) m/z: 679.19 ([M+H]$^-$).

Reverse-phase HPLC, eluting with 0.1 M TEAB/AcCN from 90/10 to 0/100 in 30 min, F=1 mL/min, λ=254 nm, one peak for two diastereoisomers with t$_R$=14.23 min.

Example 15: 2-Chloro-9-(2'-Deoxy-2'-fluoro-β-D-arabinofuranosyl)adenine-5'-O-[1-phenyl(isopropoxy-L-alaninyl)] Diphosphate Triethylammonium Salt

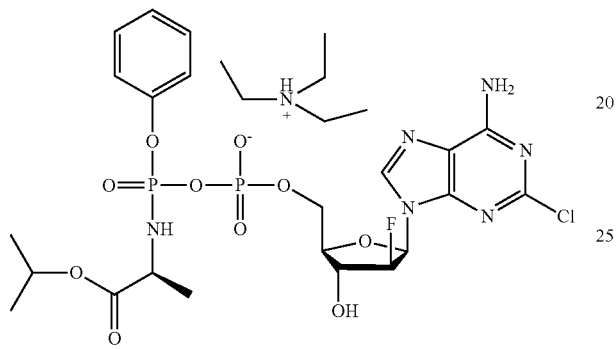

(15)

Prepared according to the general procedure from 2-chloro-9-(2'-deoxy-2'-fluoro-β-D-arabinofuranosyl)adenine-5'-monophosphate TEA salt (0.86 g, 1.48 mmol), phenyl(isopropoxy-L-alaninyl)phosphorochloridate (0.45 g, 1.48 mmol) and TEA (0.59 mL, 4.25 mmol) as a white solid (0.126 g, 11%).

$^{31}$P NMR (202 MHz, CD$_3$OD): δ$_P$ −7.62 (d, J=21.0 Hz), −7.85 (d, J=21.0 Hz), −12.14 (apparent t, J=20.2 Hz).

$^1$H NMR (500 MHz, CD$_3$OD): δ$_H$ 8.30 (1H, d, 5J$_{H-F}$=2.0 Hz, H-8), 7.35-7.27 (4H, m, H-Ar), 7.18-7.14 (1H, m, H-Ar), 6.45 (0.5H, t, J=3.5 Hz, H-1'), 6.42 (0.5H, t, J=3.5 Hz, H-1'), 5.22 (0.5H, q, J=3.5 Hz, H-2'), 5.13 (0.5H, q, J=3.5 Hz, H-2'), 4.96-4.94 (1H, m, OCH(CH$_3$)$_2$), 4.61-4.58 (0.5H, m, H-3'), 4.57-4.55 (0.5H, m, H-3'), 4.29-4.25 (2H, m, H-5'), 4.19-4.15 (1H, m, NHCHCH$_3$), 4.07-4.00 (1H, m, H-4'), 3.33 (6H, q, J=7.0 Hz, N(CH$_2$CH$_3$)$_3$), 1.38 (1H, d, J=7.5 Hz, NHCHCH$_3$), 1.33 (2H, dd, J=7.5 Hz, NHCHCH$_3$), 1.31 (9H, t, J=7.5 Hz, N(CH$_2$CH$_3$)$_3$), 1.20 (6H, apparent t, J=6.0 Hz, OCH(CH$_3$)$_2$).

$^{13}$C NMR (125 MHz, CD$_3$OD): δ$_C$ 173.10 (d, $^3$J$_{C-P}$=7.1 Hz, C=O, ester), 173.02 (C=O, ester), 156.73 (C-6), 154.16 (C-2), 150.92, 150.86 (2×d, $^2$J$_{C-P}$=5.2 Hz, C-Ar), 150.24 (C-4), 142.55 (C-8), 129.26, 124.64, 124.62 (CH-Ar), 120.34 (d, $^3$J$_{C-P}$=4.5 Hz, CH-Ar), 117.16 (C-5), 95.00 (d, $^1$J$_{C-F}$=191.5 Hz, C-2'), 82.90 (d, $^3$J$_{C-F}$=6.5 Hz C-4'), 82.80, 82.76 (2×d, $^2$J$_{C-F}$=10.5 Hz C-1'), 73.60, 73.59 (2×d, $^2$J$_{C-F}$=24.5 Hz C-3'), 68.71 (OCH(CH$_3$)$_2$), 65.08 (d, $^2$J$_{C-P}$=4.2 Hz, C-5'), 50.39, 50.34 (2×d, $^2$J$_{C-P}$=1.8 Hz, NHCHCH$_3$), 46.23 (N(CH$_2$CH$_3$)$_3$), 20.61, 20.54 (OCH(CH$_3$)$_2$), 19.60, 19.47 (2×d, $^3$J$_{C-P}$=6.0 Hz, NHCHCH$_3$), 7.86 (N(CH$_2$CH$_3$)$_3$).

C$_{22}$H$_{28}$ClFN$_6$O$_{10}$P$_2$ mass required m/z 652.10; found MS (ES$^-$) m/z: 651.13 ([M+H]$^-$).

Reverse-phase HPLC, eluting with 0.1 M TEAB/AcCN from 90/10 to 0/100 in 30 min, F=1 mL/min, λ=254 nm, one peak for two diastereoisomers with t$_R$=12.32 min.

Example 16: 2-Chloro-9-(2'-Deoxy-2'-fluoro-β-D-arabinofuranosyl)adenine-5'-O-[1-phenyl(methoxy-L-alaninyl)] Diphosphate Triethylammonium Salt

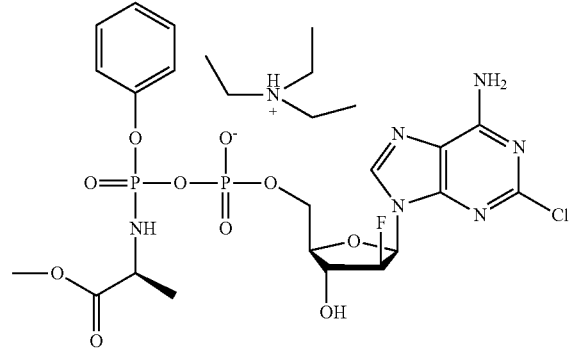

(16)

Prepared according to the general procedure from 2-chloro-9-(2'-deoxy-2'-fluoro-β-D-arabinofuranosyl)adenine-5'-monophosphate TEA salt (0.86 g, 1.48 mmol), phenyl(methoxy-L-alaninyl)phosphorochloridate (0.41 g, 1.48 mmol) and TEA (0.59 mL, 4.25 mmol) as a white solid (0.182 g, 17%).

$^{31}$P NMR (202 MHz, CD$_3$OD): δ$_P$ −7.73 (d, J=20.7 Hz), −7.84 (d, J=20.8 Hz), −12.04 (d, J=21.0 Hz), −12.11 (d, J=20.8 Hz).

$^1$H NMR (500 MHz, CD$_3$OD): δ$_H$ 8.31 (0.5H, d, J$_{H-F}$=2.5 Hz, H-8), 8.30 (0.5H, d, J$_{H-F}$=2.0 Hz, H-8), 7.35-7.27 (4H, m, H-Ar), 7.18-7.14 (1H, m, H-Ar), 6.44 (0.5H, dd, J$_{H-F}$=16.4 Hz, J=3.9 Hz, H-1'), 6.42 (0.5H, dd, J$_{H-F}$=16.4 Hz, J=3.7 Hz, H-1'), 5.20-5.09 (1H, m, H-2'), 4.68-4.52 (1H, m, H-3'), 4.28-4.24 (2H, m, H-5'), 4.18-4.15 (1H, m, H-4'), 4.12-4.07 (1H, m, NHCHCH$_3$), 3.66 (1.5H, s, OCH$_3$), 3.65 (1.5H, s, OCH$_3$), 3.78 (6H, q, J=7.0 Hz, N(CH$_2$CH$_3$)$_3$), 1.37 (1.5H, dd, J=7.0 Hz, J=0.5 Hz, NHCHCH$_3$), 1.32 (1.5H, dd, J=7.0 Hz, J=0.5 Hz, NHCHCH$_3$), 1.14 (9H, t, J=7.5 Hz, N(CH$_2$CH$_3$)$_3$).

C$_{20}$H$_{24}$ClFN$_6$O$_{10}$P$_2$ mass required m/z 724.07; found MS (ES$^-$) m/z: 723.01 ([M+H]$^-$).

Reverse-phase HPLC, eluting with 0.1 M TEAB/AcCN from 90/10 to 0/100 in 30 min, F=1 mL/min, λ=254 nm, one peak for two diastereoisomers with t$_R$=12.24 min.

Example 17: 2-Chloro-9-(2'-Deoxy-2'-fluoro-β-D-arabinofuranosyl)adenine-5'-O-[1-1-naphthyl(benzoxy-L-alaninyl)] Diphosphate Triethylammonium Salt

Example 18: 2-Chloro-9-(2'-Deoxy-2'-fluoro-β-D-arabinofuranosyl)adenine-5'-O-[1-phenyl(hexoxy-L-alaninyl)] Diphosphate Triethylammonium Salt

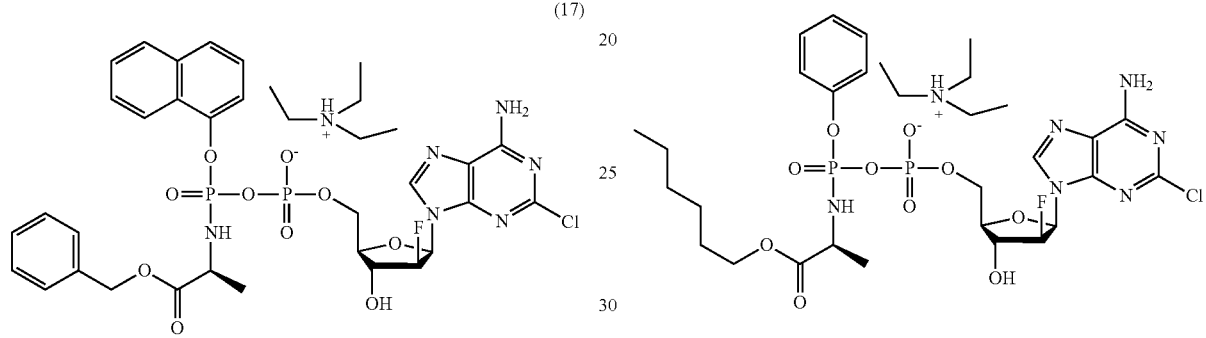

(17)

(18)

Prepared according to the general procedure from 2-chloro-9-(2'-deoxy-2'-fluoro-β-D-arabinofuranosyl)adenine-5'-monophosphate TEA salt (0.86 g, 1.48 mmol), 1-naphthyl(benzoxy-L-alaninyl)phosphorochloridate (0.59 g, 1.48 mmol) and TEA (0.59 mL, 4.25 mmol) as a white solid (0.226 g, 18%).

$^{31}$P NMR (202 MHz, CD$_3$OD): δ$_P$ −7.26 (d, J=20.2 Hz), −7.61 (d, J=20.2 Hz), −12.07 (d, J=20.40 Hz), −12.27 (d, J=20.40 Hz).

$^1$H NMR (500 MHz, CD$_3$OD): δ$_H$ 8.19-8.17 (2H, m, H-Ar), 8.13 (0.5H, d, J$_{H-F}$=2.0 Hz, H-8), 8.12 (0.5H, d, J$_{H-F}$=2.0 Hz, H-8), 7.72-7.68 (2H, m, H-Ar), 7.54-7.52 (1H, apparent d, J=9.5 Hz, H-Ar), 7.44-7.40 (4H, m, H-Ar), 7.37-7.35 (1H, m, H-Ar), 6.28 (0.5H, t, J=4.0 Hz, H-1'), 6.25 (0.5H, t, J=4.0 Hz, H-1'), 5.06-5.02 (0.5H, m, H-2'), 4.95-4.93 (0.5H, m, H-2'), 4.89-4.80 (2H, OCH$_2$Ph), 4.43-4.43 (0.5H, m, H-3'), 4.41-4.40 (0.5H, m, H-3'), 4.15-4.12 (2H, m, H-5'), 4.09-4.06 (1H, m, H-4'), 3.33 (6H, q, J=7.0 Hz, N(CH$_2$CH$_3$)$_3$), 1.23 (1.5H, dd, J=7.0 Hz, J=0.5 Hz, NHCHCH$_3$), 1.20 (1.5H, dd, J=7.0 Hz, J=0.5 Hz, NHCHCH$_3$), 1.31 (9H, t, J=7.5 Hz, N(CH$_2$CH$_3$)$_3$).

C$_{30}$H$_{30}$ClFN$_6$O$_{10}$P$_2$ mass required m/z 750.99; found MS (ES$^−$) m/z: 749.19 ([M+H]$^−$).

Reverse-phase HPLC, eluting with 0.1 M TEAB/AcCN from 90/10 to 0/100 in 30 min, F=1 mL/min, λ=254 nm, t$_R$=14.69, 14.81 min.

Prepared according to the general procedure from 2-chloro-9-(2'-deoxy-2'-fluoro-β-D-arabinofuranosyl)adenine-5'-monophosphate TEA salt (0.86 g, 1.48 mmol), 1-phenyl(hexoxy-L-alaninyl)phosphorochloridate (0.51 g, 1.48 mmol) and TEA (0.59 mL, 4.25 mmol) as a white solid (0.235 g, 20%).

$^{31}$P NMR (202 MHz, CD$_3$OD): δ$_P$ −7.55 (d, J=23.00 Hz), −7.77 (d, J=19.40 Hz), −12.09 (d, J=19.40 Hz), −12.19 (d, J=20.10 Hz).

$^1$H NMR (500 MHz, CD$_3$OD): δ$_H$ 8.18 (0.5H, d, J$_{H-F}$=2.0 Hz, H-8), 8.17 (0.5H, d, J$_{H-F}$=2.0 Hz, H-8), 7.23-7.11 (4H, m, H-Ar), 7.08-7.03 (1H, m, H-Ar), 6.33 (0.5H, dd, J=4.0, 1.5 Hz, H-1'), 6.29 (0.5H, dd, J=4.0 Hz, J=1.5 Hz, H-1'), 5.08-5.06 (0.5H, m, H-2'), 4.98-4.96 (0.5H, m, H-2'), 4.47-4.45 (0.5H, m, H-3'), 4.44-4.42 (0.5H, m, H-3'), 4.15-4.11 (2H, m, H-5'), 4.06-4.03 (1H, m, NHCHCH$_3$), 3.97-3.90 (5H, m, H-4', 2×CH$_2$, OCH$_2$(CH$_2$)$_4$CH$_3$), 3.84-3.78 (1H, m, OCH$_2$(CH$_2$)$_4$CH$_3$), 3.33 (6H, q, J=7.0 Hz, N(CH$_2$CH$_3$)$_3$, 1.50-1.43 (4H, m, 2×CH$_2$, OCH$_2$(CH$_2$)$_4$CH$_3$), 1.31-1.22 (6H, m, CH$_2$, OCH$_2$(CH$_2$)$_4$CH$_3$, NHCHCH$_3$), 1.31 (9H, t, J=7.5 Hz, N(CH$_2$CH$_3$)$_3$), 0.81-0.76 (3H, m, OCH$_2$(CH$_2$)$_4$CH$_3$).

C$_{25}$H$_{34}$ClFN$_6$O$_{10}$P$_2$ mass required m/z 694.97; found MS (ES$^−$) m/z: 693.14 ([M+H]$^−$).

Reverse-phase HPLC, eluting with 0.1 M TEAB/AcCN from 90/10 to 0/100 in 30 min, F=1 mL/min, λ=254 nm, t$_R$=15.13 and 15.21 min.

Example 19: 2-Chloro-9-(2'-Deoxy-2'-fluoro-β-D-arabinofuranosyl)adenine-5'-O-[1-5,6,7,8-tetrahydro-1-naphthyl(benzoxy-L-alaninyl)] Diphosphate Triethylammonium Salt

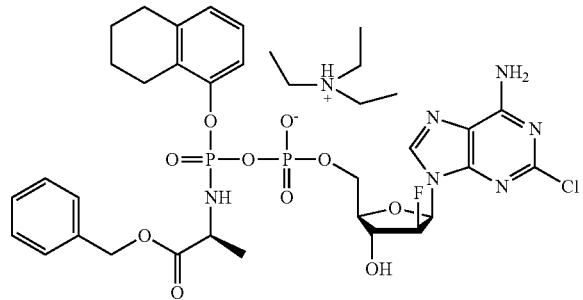

(19)

Prepared according to the general procedure from 2-chloro-9-(2'-deoxy-2'-fluoro-β-D-arabinofuranosyl)adenine-5'-monophosphate TEA salt (0.86 g, 1.48 mmol), 5,6,7,8-tetrahydro-1-naphthyl(benzoxy-L-alaninyl)phosphorochloridate (0.603 g, 1.48 mmol) and TEA (0.59 mL, 4.25 mmol) as a white solid (0.19 g, 15%).

$^{31}$P NMR (202 MHz, CD$_3$OD): δ$_P$ −7.06 (d, J=24.0 Hz), −7.55 (d, J=21.2 Hz), −11.24 (d, J=21.2 Hz), −11.38 (d, J=24.0 Hz).

$^1$H NMR (500 MHz, CD$_3$OD): δ$_H$ 8.27 (0.5H, d, J$_{H-F}$=2.0 Hz, H-8), 8.25 (0.5H, d, J$_{H-F}$=2.0 Hz, H-8), 7.33-7.30 (3H, m, H-Ar), 7.22-7.18 (2H, m, H-Ar), 7.00-6.93 (2H, m, H-Ar), 6.84 (1H, apparent t, J=6.5 Hz, H-Ar), 6.72 (1H, apparent d, J=7.5 Hz, H-Ar), 6.43 (0.5H, dd, J=4.0 Hz, J=2.0 Hz, H-1'), 6.39 (0.5H, dd, J=4.0 Hz, J=2.0 Hz, H-1'), 5.19-5.16 (0.5H, m, H-2'), 5.09-5.06 (0.5H, m, H-2'), 5.06-5.03 (2H, m, OCH$_2$Ph), 4.56-4.49 (1H, m, H-3'), 4.27-4.10 (3H, m, H-5', H-4'), 4.02-3.97 (1H, m, NHCHCH$_3$), 3.33 (6H, q, J=7.0 Hz, N(CH$_2$CH$_3$)$_3$), 2.73 (4H, bt, 2×CH$_2$), 1.75-1.72 (4, m, 2×CH$_2$), 1.42 (1.5H, d, J=7.5 Hz, NHCHCH$_3$), 1.38 (1.5H, dd, J=7.0 Hz, NHCHCH$_3$), 1.31 (9H, t, J=7.5 Hz, N(CH$_2$CH$_3$)$_3$).

$C_{30}H_{34}ClFN_6O_{10}P_2$ mass required m/z 754.15, found MS (ES$^-$) m/z: 753.23 ([M+H]$^-$).

Reverse-phase HPLC, eluting with 0.1 M TEAB/AcCN from 90/10 to 0/100 in 30 min, F=1 mL/min, λ=254 nm, t$_R$=15.32 and 15.44 min.

Example 20: 2-Chloro-9-(2'-Deoxy-2'-fluoro-β-D-arabinofuranosyl)adenine-5'-O-[1-ethyl(benzoxy-L-alaninyl)] Diphosphate Triethylammonium Salt

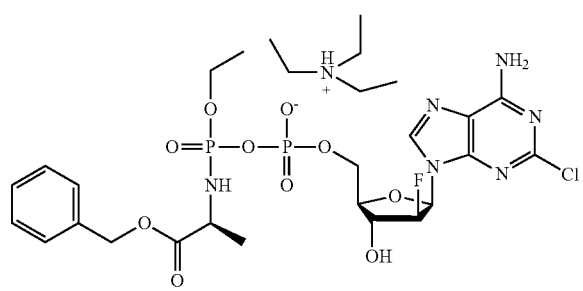

(20)

Prepared according to the general procedure from 2-chloro-9-(2'-deoxy-2'-fluoro-β-D-arabinofuranosyl)adenine-5'-monophosphate TEA salt (0.86 g, 1.48 mmol), ethyl(benzoxy-L-alaninyl)phosphorochloridate (0.45 g, 1.48 mmol) and TEA (0.59 mL, 4.25 mmol) as a white solid (0.218 g, 20%).

$^{31}$P NMR (202 MHz, CD$_3$OD): δ$_P$ −2.73 (d, J=20.2 Hz), −3.04 (d, J=20.4 Hz), −11.96 (d, J=20.2 Hz), −12.07 (d, J=20.04 Hz).

$^1$H NMR (500 MHz, CD$_3$OD): δ$_H$ 8.32 (0.5H, d, J$_{H-F}$=2.0 Hz, H-8), 8.31 (0.5H, d, J$_{H-F}$=2.0 Hz, H-8), 7.37-7.27 (5H, m, H-Ar), 6.46 (0.5H, dd, J=4.0 Hz, J=2.0 Hz, H-1'), 6.43 (0.5H, dd, J=4.0 Hz, J=2.0 Hz, H-1'), 5.24-5.22 (0.5H, m, H-2'), 5.20-5.14 (2H, m, OCH$_2$Ph), 5.13-5.11 (0.5H, m, H-2'), 4.62-4.60 (0.5H, m, H-3'), 4.59-4.57 (0.5H, m, H-3'), 4.29-4.26 (2H, m, H-5'), 4.19-4.17 (2H, m, NHCHCH$_3$), 4.12-4.04 (3H, m, H-4', OCH$_2$CH$_3$), 2.86 (6H, q, J=7.0 Hz, N(CH$_2$CH$_3$)$_3$), 1.43 (1.5H, dd, J=7.0 Hz, J=0.5 Hz, NHCHCH$_3$), 1.42 (1.5H, dd, J=7.0 Hz, J=0.5 Hz, NHCHCH$_3$), 1.27-1.23 (3H, m, OCH$_2$CH$_3$), 1.19 (9H, t, J=7.5 Hz, N(CH$_2$CH$_3$)$_3$).

$C_{22}H_{28}ClFN_6O_{10}P_2$ mass required m/z 652.89; found MS (ES$^-$) m/z: 651.15 ([M+H]$^-$).

Reverse-phase HPLC, eluting with 0.1 M TEAB/AcCN from 90/10 to 0/100 in 30 min, F=1 mL/min, λ=254 nm, one peak for two diastereoisomers with t$_R$=14.12 min.

Example 21: 2-Chloro-9-(2'-Deoxy-2'-fluoro-β-D-arabinofuranosyl)adenine-5'-O-[1-phenyl(benzoxy-L-leucinyl)] Diphosphate Triethylammonium Salt

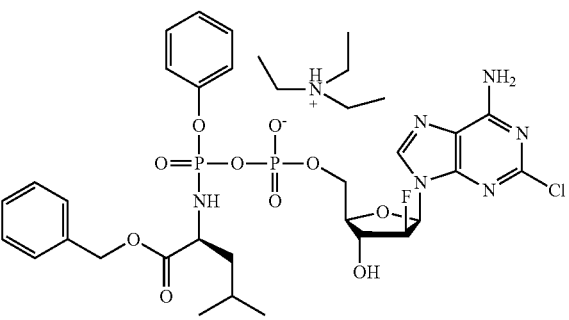

(21)

Prepared according to the general procedure from 2-chloro-9-(2'-deoxy-2'-fluoro-β-D-arabinofuranosyl)adenine-5'-monophosphate TEA salt (0.86 g, 1.48 mmol), phenyl(benzoxy-L-leucinyl)phosphorochloridate (0.58 g, 1.48 mmol) and TEA (0.59 mL, 4.25 mmol) as a white solid (0.30 g, 24%).

$^{31}$P NMR (202 MHz, CD$_3$OD): δ$_P$ −7.28 (d, J=21.4 Hz), −7.57 (d, J=21.6 Hz), −12.18 (d, J=21.6 Hz).

$^1$H NMR (500 MHz, CD$_3$OD): δ$_H$ 8.18 (1H, s, H-8), 7.19-7.10 (8H, m, H-Ar), 7.06-6.99 (2H, m, H-Ar), 6.32 (0.5H, t, J=3.5 Hz, H-1'), 6.29 (0.5H, t, J=3.5 Hz, H-1'), 5.10-5.08 (0.5H, m, H-2'), 4.97-4.88 (2.5H, m, H-2', OCH$_2$Ph), 4.46 (0.5H, apparent t, J=3.5 Hz, H-3'), 4.43 (0.5H, apparent t, J=3.5 Hz, H-3'), 4.17-4.13 (2H, m, H-5'), 4.06-4.04 (1H, m, H-4'), 3.94-3.88 (1H, m, NHCHCH$_2$CH(CH$_3$)$_2$), 3.33 (6H, q, J=7.0 Hz, N(CH$_2$CH$_3$)$_3$), 1.13 (9H, t, J=7.5 Hz, N(CH$_2$CH$_3$)$_3$), 1.43-1.37 (3H, m, NHCHCH$_2$CH(CH$_3$)$_2$), 0.75-0.72 (3H, m, NHCHCH$_2$CH(CH$_3$)$_2$), 0.65-0.64 (3H, apparent dd, J=14.0 Hz, J=6.0 Hz, NHCHCH$_2$CH(CH$_3$)$_2$).

$^{13}$C NMR (125 MHz, CD$_3$OD): δ$_C$ 173.43, 173.22 (2×d, $^3J_{C—P}$=3.5 Hz, C=O, ester), 156.78, 156.72 (C-6), 154.16 (C-2), 150.92 (d, $^2J_{C—P}$=7.0 Hz, C-Ar), 150.24 (C-4), 135.84, 84, 135.81 (C-8), 129.26, 128.74, 128.26, 128.13, 127.95, 127.90, 127.88, 127.83, 124.68, 124.57, 122.30 (CH-Ar), 120.44 (d, $^3J_{C—P}$=4.6 Hz, CH-Ar), 120.27 (d, $^3J_{C—P}$=5.2 Hz, CH-Ar), 119.98, 119.94 (CH-Ar), 117.17 (C-5), 95.00 (d, $^1J_{C—F}$=191.6 Hz, C-2'), 82.90 (d, $^3J_{C—F}$=4.1 Hz C-4'), 82.74 (d, $^2J_{C—P}$=11.0 Hz C-1'), 73.63, 73.58 (2×d, $^2J_{C—F}$=24.5 Hz, C-3'), 66.43, 66.05 (OCH$_2$Ph), 65.10 (d, $^2J_{C—P}$=5.5 Hz, C-5), 53.70 (NHCH), 53.31 (d, $^2J_{C—P}$=5.5 Hz, NHCH), 46.21 (N(CH$_2$CH$_3$)$_3$), 43.20, 43.00 (2×d, $^3J_{C—P}$=7.0 Hz, NHCHCH$_2$), 24.13, 24.08 (NHCHCH$_2$CH(CH$_3$)$_2$), 21.66, 21.45, 21.07, 20.99 (NHCHCH$_2$CH(CH$_3$)$_2$), 7.83 (N(CH$_2$CH$_3$)$_3$).

C$_{29}$H$_{34}$ClFN$_6$O$_{10}$P$_2$ mass required m/z 742.15, found MS (ES$^-$) m/z: 741.18 ([M+H]$^-$).

Reverse-phase HPLC, eluting with 0.1 M TEAB/AcCN from 90/10 to 0/100 in 30 min, F=1 mL/min, λ=254 nm, one peak for two diastereoisomers with t$_R$=14.91 min.

Example 22: 2-Chloro-9-(2'-Deoxy-2'-fluoro-β-D-arabinofuranosyl)adenine-5'-O-[1-phenyl(benzoxy-L-phenylalaninyl)] Diphosphate Triethylammonium Salt

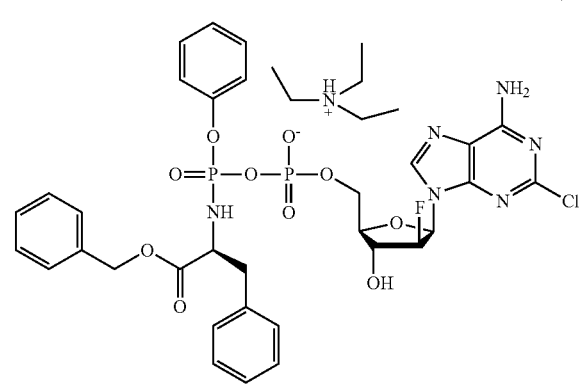

(22)

Prepared according to the general procedure from 2-chloro-9-(2'-deoxy-2'-fluoro-β-D-arabinofuranosyl)adenine-5'-monophosphate TEA salt (0.86 g, 1.48 mmol), phenyl(benzoxy-L-phenylalaninyl)phosphorochloridate (0.63 g, 1.48 mmol) and TEA (0.59 mL, 4.25 mmol) as a white solid (0.185 g, 14%).

$^{31}$P NMR (202 MHz, CD$_3$OD): δ$_P$ −7.88 (d, J=20.6 Hz), −7.98 (d, J=20.0 Hz), −12.00 (d, J=21.21 Hz).

$^1$H NMR (500 MHz, CD$_3$OD): δ$_H$ 8.17 (0.5H, d, $^5J_{H—F}$=2.5 Hz, H-8), 8.14 (0.5H, d, $^5J_{H—F}$=2.5 Hz, H-8), 7.18-7.08 (10, m, H-Ar), 6.97-6.87 (5H, m, H-Ar), 6.30 (0.5H, dd, J=4.0 Hz, J=1.5 Hz, H-1'), 6.27 (0.5H, dd, J=4.0 Hz, J=1.5 Hz, H-1'), 5.08-5.05 (0.5H, m, H-2'), 4.97-4.95 (0.5H, m, H-2'), 4.86-4.77 (4H, m OCH$_2$Ph, NHCHCH$_2$Ph), 4.46-4.44 (0.5H, m, H-3'), 4.43-4.41 (0.5H, m, H-3'), 4.25-4.17 (1H, m, NHCHCH$_2$Ph), 4.16-4.12 (2H, m, H-5'), 4.10-4.05 (1H, m, H-4'), 3.33 (6H, q, J=7.0 Hz, N(CH$_2$CH$_3$)$_3$), 1.31 (9H, t, J=7.5 Hz, N(CH$_2$CH$_3$)$_3$).

$^{13}$C NMR (125 MHz, CD$_3$OD): δ$_C$ 173.46 (d, $^3J_{C—P}$=4.6 Hz, C=O, ester), 172.05 (d, $^3J_{C—P}$=4.5 Hz, C=O, ester), 156.68 (C-6), 154.13 (C-2), 153.36 (d, $^2J_{C—P}$=7.1 Hz, C-Ar), 150.85, 150.83 (C-4), 150.23 (C-Ar), 136.73, 136.11 (d, $^2J_{C—P}$=4.7 Hz, C-Ar), 135.69 (C-8), 135.52, 135.50 (C-Ar), 129.20 (d, $^3J_{C—P}$=3.1 Hz, CH-Ar), 128.74, 128.09, 128.05 (d, $^3J_{C—P}$=2.8 Hz, CH-Ar), 127.90, 127.84, 127.78, 126.44, 126.25, 124.59, 122.40, 120.38, 120.34, 120.30, 120.26, 120.15, 120.11 (CH-Ar), 117.15 (C-5), 95.01 (d, $^1J_{C—F}$=191.0 Hz, C-2'), 95.00 (d, $^1J_{C—F}$=191.0 Hz, C-2'), 82.84 (d, $^3J_{C—F}$=3.8 Hz C-4'), 82.68 (d, $^2J_{C—F}$=32.5 Hz C-1'), 73.58 (d, $^2J_{C—F}$=24.5 Hz C-3'), 66.45, 66.44 (OCH$_2$Ph), 66.11 (OCH$_2$Ph), 65.04 (d, $^2J_{C—P}$=4.8 Hz, C-5'), 56.44 (NHCHCH$_2$Ph), 56.19 (NHCHCH$_2$Ph), 46.21 (N(CH$_2$CH$_3$)$_3$), 40.79, 40.74 (CH$_2$Ph), 9.85 (N(CH$_2$CH$_3$)$_3$).

C$_{32}$H$_{32}$ClFN$_6$O$_{10}$P$_2$ mass required m/z 776.13; found MS (ES$^-$) m/z: 775.17 ([M+H]$^-$).

Reverse-phase HPLC, eluting with 0.1 M TEAB/AcCN from 90/10 to 0/100 in 30 min, F=1 mL/min, λ=254 nm, one peak for two diastereoisomers with t$_R$=24.28 min.

Example 23: 2-Chloro-9-(2'-Deoxy-2'-fluoro-β-D-arabinofuranosyl)adenine-5'-O-[1-phenyl(benzoxy-L-prolinyl)] Diphosphate Triethylammonium Salt

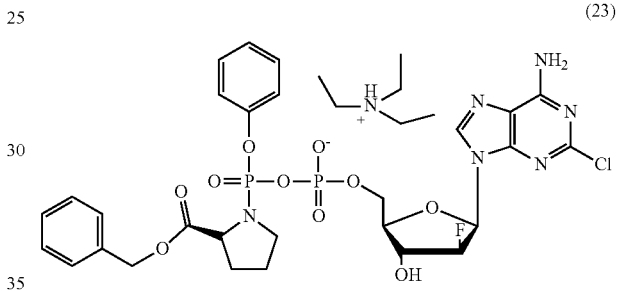

(23)

Prepared according to the general procedure from 2-chloro-9-(2'-deoxy-2'-fluoro-β-D-arabinofuranosyl)adenine-5'-monophosphate TEA salt (0.86 g, 1.48 mmol), phenyl(benzoxy-L-prolinyl)phosphorochloridate (0.55 g, 1.48 mmol) and TEA (0.59 mL, 4.25 mmol) as a white solid (0.17 g, 14%).

$^{31}$P NMR (202 MHz, CD$_3$OD): δ$_P$ −9.05 (d, J=17.6 Hz), −9.72 (d, J=21.6 Hz), −11.75 (d, J=17.6 Hz), −12.12 (d, J=21.6 Hz).

$^1$H NMR (500 MHz, CD$_3$OD): δ$_H$ 8.17 (0.5H, d, J$_{H—F}$=2.5 Hz, H-8), 8.16 (0.5H, d, J$_{H—F}$=2.5 Hz, H-8), 7.21-7.15 (8H, m, H-Ar), 7.11-7.09 (1H, m, H-Ar), 7.04-7.00 (1H, m, H-Ar), 6.32 (0.5H, d, J=4.0 Hz, H-1'), 6.31 (0.5H, d, J=4.0 Hz, H-1'), 5.08-5.06 (0.5H, m, H-2'), 5.01-4.99 (0.5H, m, H-2'), 4.98-4.91 (2H, m, OCH$_2$Ph), 4.48-4.45 (1H, m, NCH), 4.43-4.41 (0.5H, m, H-3'), 4.34-4.30 (0.5H, m, H-3'), 4.16-4.09 (2H, m, H-5'), 4.05-4.00 (1H, m, H-4'), 3.46-3.38 (2H, m, NCH$_2$), 2.21-2.05 (1H, m, one H of NCH$_2$CH$_2$), 1.85-1.76 (3H, m, 1×H, NCH$_2$CH$_2$, 2×H, NCH$_2$CH$_2$CH$_2$), 3.33 (6H, q, J=7.0 Hz, N(CH$_2$CH$_3$)$_3$, 1.31 (9H, t, J=7.5 Hz, N(CH$_2$CH$_3$)$_3$).

$^{13}$C NMR (125 MHz, CD$_3$OD): δ$_C$ 173.60, 173.31 (C=O, ester), 156.69 (C-6), 154.14 (C-2), 150.78 (d, $^2J_{C—P}$=3.8 Hz, C-Ar), 150.22 (C-4), 136.37 (C-8), 136.03, 135.96 (C-Ar), 129.29, 129.23, 128.13, 127.80, 127.76, 127.67, 124.57 (CH-Ar), 120.15 (d, $^3J_{C—P}$=5.2 Hz, CH-Ar), 119.96 (d, $^3J_{C—P}$=5.2 Hz, CH-Ar), 117.14 (C-5), 95.02 (d, $^1J_{C—F}$=191.7 Hz, C-2'), 94.99 (d, $^1J_{C—F}$=191.7 Hz, C-2'), 82.85 (d, $^3J_{C—F}$=5.6 Hz C-4'), 82.71 (d, $^2J_{C—F}$=32.5 Hz C-1'), 73.59 (d, $^2J_{C—F}$=24.5 Hz C-3'), 73.55 (d, $^2J_{C—F}$=24.5 Hz, C-3'), 66.32, 66.25 (OCH$_2$Ph), 65.02 (d, $^2J_{C—P}$=4.0 Hz, C-5'), 64.90 (d, $^2J_{C-P}$=4.0 Hz, C-5'), 60.72 ($^2J_{C-P}$=7.75 Hz, NCH), 60.35 ($^2J_{C-P}$=7.75 Hz, NCH), 46.31 (N(CH$_2$CH$_3$)$_3$), 30.99 ($^2J_{C-P}$=11.0 Hz, NCH$_2$), 30.89 ($^2J_{C-P}$=11.0 Hz, NCH$_2$), 24.84 ($^3J_{C-P}$=9.0 Hz, NCH$_2$CH$_2$), 24.40 ($^3J_{C-P}$=9.0 Hz, NCHCH$_2$), 7.85 (N(CH$_2$CH$_3$)$_3$).

C$_{28}$H$_{30}$ClFN$_6$O$_{10}$P$_2$ mass required m/z 726.97; found MS (ES$^-$) m/z: 725.67 ([M+H]$^-$).

Reverse-phase HPLC, eluting with 0.1 M TEAB/AcCN from 90/10 to 0/100 in 30 min, F=1 mL/min, λ=254 nm, one peak for two diastereoisomers with t$_R$=15.39 min.

Example 24: 2-Chloro-9-(2'-Deoxy-2'-fluoro-β-D-arabinofuranosyl)adenine-5'-O-[1-phenyl(methoxy-L-metioninyl)] Diphosphate Triethylammonium Salt

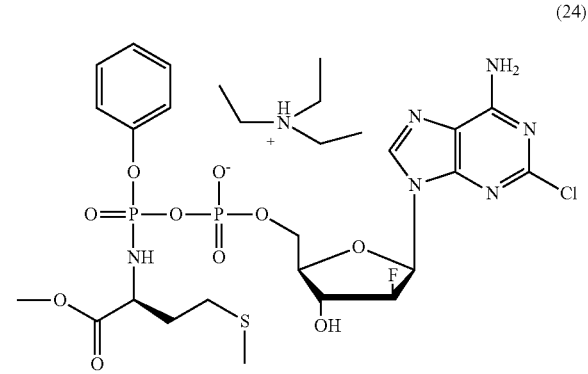

(24)

Prepared according to the general procedure from 2-chloro-9-(2'-deoxy-2'-fluoro-β-D-arabinofuranosyl)adenine-5'-monophosphate TEA salt (0.86 g, 1.48 mmol), phenyl(methoxy-L-methioninyl)phosphorochloridate (0.49 g, 1.48 mmol) and TEA (0.59 mL, 4.25 mmol) as a white solid (0.25 g, 22%).

$^{31}$P NMR (202 MHz, CD$_3$OD): δ$_P$ −7.41 (d, J=21.33 Hz), −7.69 (d, J=21.6 Hz), −12.29 (d, J=20.6 Hz).

$^1$H NMR (500 MHz, CD$_3$OD): δ$_H$ 8.19 (0.5H, d, J$_{H-F}$=2.1 Hz, H-8), 8.18 (0.5H, d, J$_{H-F}$=2.0 Hz, H-8), 7.21-7.16 (4H, m, H-Ar), 7.09-7.02 (1H, m, H-Ar), 6.32 (0.5H, dd, J$_{H-F}$=16.6 Hz, J=4.3 Hz, H-1'), 6.31 (0.5H, dd, J$_{H-F}$=16.6 Hz, J=4.2 Hz, H-1'), 5.02 (0.5H, dd J$_{H-F}$=51.9 Hz, J$_{H-F}$=2.2 Hz, H-2') 5.00 (0.5H, dd, J$_{H-F}$=51.9 Hz, J$_H$-H=2.2 Hz, H-2'), 4.48-4.43 (1H, m, H-3'), 4.17-4.13 (2H, m, H-5'), 4.08-4.00 (m, 2H, NHCHCH$_3$, H-4'), 3.56, 3.43 (3H, 2s, OCH$_3$), 2.80 (6H, q, J=7.0 Hz, N(CH$_2$CH$_3$)$_3$), 2.42-2.39 (1H, m, CH$_3$SCH$_2$CH$_2$a), 2.28-2.24 (1H, m, CH$_3$SCH$_2$CH$_{2b}$), 1.90, 1.86 (3H, 2×s, SCH$_3$), 1.90-1.71 (2H, m, CH$_3$SCH$_2$CH$_2$a).

C$_{22}$H$_{28}$ClFN$_6$O$_{10}$P$_2$S mass required 684.96; found MS (ES$^-$) m/z: 683 ([M+H]$^-$).

Reverse-phase HPLC, eluting with 0.1 M TEAB/AcCN from 90/10 to 0/100 in 30 min, F=1 mL/min, λ=254 nm, one peak for two diastereoisomers with t$_R$=12.28 min.

Example 25: 2-Chloro-9-(2'-Deoxy-2'-fluoro-β-D-arabinofuranosyl)adenine-5'-O-[1-phenyl(ethoxy-L-isoleucinyl)] Diphosphate Triethylammonium Salt

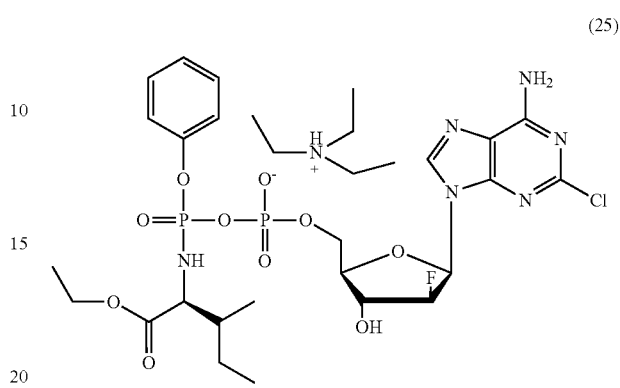

(25)

Prepared according to the general procedure from 2-chloro-9-(2'-deoxy-2'-fluoro-β-D-arabinofuranosyl)adenine-5'-monophosphate TEA salt (0.86 g, 1.48 mmol), phenyl(ethoxy-L-isoleucinyl)phosphorochloridate (0.49 g, 1.48 mmol) and TEA (0.59 mL, 4.25 mmol) as a white solid (0.26 g, 23%).

$^{31}$P NMR (202 MHz, CD$_3$OD): δ$_P$ −6.84 (d, J=21.5 Hz), −6.99 (d, J=22.3 Hz), −12.00 (d, J=21.6 Hz).

$^1$H NMR (500 MHz, CD$_3$OD): δ$_H$ 8.30, (0.5H, d, J$_{H-F}$=2.4 Hz, H-8), 8.29 (0.5H, d, J$_{H-F}$=2.3 Hz, H-8), 7.35-7.23 (4H, m, H-Ar), 7.19-7.13 (1H, m, H-Ar), 6.44 (0.5H, dd, J$_{H-F}$=16.7 Hz, J=3.9 Hz, H-1'), 6.43 (0.5H, dd, J$_{H-F}$=16.7 Hz, J$_H$-H=4.2 Hz, H-1'), 5.21-5.08 (1H, m, H-2'), 4.59-4.54 (1H, m, H-3'), 4.28-4.25 (2H, m, OCH$_2$CH$_3$), 4.18-4.07 (3H, m, H-5'$_a$, H-4', NHCHCH$_3$), 3.83 (0.5H, dd, J=9.8 Hz, J=5.7 Hz, H-5'$_b$), 3.82 (0.5H, dd, J=9.8 Hz, J=5.7 Hz, H$_b$-5'), 3.33 (6H, q, J=7.0 Hz, N(CH$_2$CH$_3$)$_3$), 1.77-1.68 (1H, m, CHCH$_3$), 1.55-1.42 (1H, m, CHCH$_2$a), 1.15-1.09 (1H, m, CHCH$_{2b}$), 1.27-1.20 (12H, m, N(CH$_2$CH$_3$)$_3$, OCH$_2$CH$_3$), 0.91-0.82 (6H, CHCH$_3$, CH$_2$CH$_3$).

C$_{24}$H$_{32}$ClFN$_6$O$_{10}$P$_2$ mass required 680.14; found MS (ES$^-$) m/z: 680.18 ([M+H]$^-$).

Reverse-phase HPLC, eluting with 0.1 M TEAB/AcCN from 90/10 to 0/100 in 30 min, F=1 mL/min, λ=254 nm, one peak for two diastereoisomers with t$_R$=13.57 min.

Example 26: 2-Chloro-9-(2'-Deoxy-2'-fluoro-β-D-arabinofuranosyl)adenine-5'-O-[1-naphthyl(benzoxy-L-alaninyl)] phosphorothiol-phosphate Triethylammonium Salt

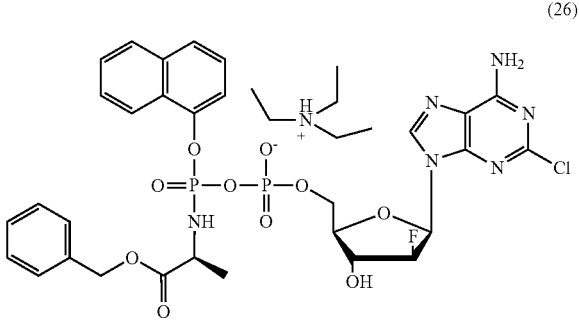

(26)

Prepared according to the general procedure from 2-chloro-9-(2'-deoxy-2'-fluoro-β-D-arabinofuranosyl)adenine-5'-monophosphate TEA salt (0.86 g, 1.48 mmol), 1-naphthyl(benzoxy-L-alaninyl)phosphorothiolchloridate (0.62 g, 1.48 mmol) and TEA (0.59 mL, 4.25 mmol) as a white solid (0.054 g, 4%).

$^{31}$P NMR (202 MHz, CD$_3$OD): δ$_P$ 55.05 (d, J=28.5 Hz), 53.71 (d, J=28.5 Hz), −12.24 (broad d, J=28.7 Hz).

$^1$H NMR (500 MHz, CD$_3$OD): δ$_H$ 8.37-8.34 (1H, m, H-Ar), 8.28 (0.5H, d, J$_{H-F}$=2.0 Hz, H-8), 8.26 (0.5H, d, J$_{H-F}$=2.0 Hz, H-8), 7.85-7.82 (1H, m, H-Ar), 7.66-7.64 (2H, m, H-Ar), 7.50-7.43 (2H, m, H-Ar), 7.38-7.19 (5H, m, H-Ar), 6.42 (0.5H, t, J=4.0 Hz, H-1'), 6.39 (0.5H, t, J=4.0 Hz, H-1'), 5.19-5.16 (1H, m, H-2'), 5.11-5.02 (2H, m, OCH$_2$Ph), 4.60-4.57 (0.5H, m, H-3'), 4.56-4.54 (0.5H, m, H-3'), 4.44-4.28 (3H, m, H-5', NHCHCH$_3$), 4.20-4.17 (1H, m, H-4'), 3.33 (6H, q, J=7.0 Hz, N(CH$_2$CH$_3$)$_3$), 1.47-1.41 (3H, m, NHCHCH$_3$), 1.31 (9H, t, J=7.5 Hz, N(CH$_2$CH$_3$)$_3$).

C$_{30}$H$_{30}$ClFN$_6$O$_9$P$_2$S mass required m/z 767.06; found MS (ES$^-$) m/z 766.12 ([M+H]$^-$).

Reverse-phase HPLC, eluting with 0.1 M TEAB/AcCN from 90/10 to 0/100 in 30 min, F=1 mL/min, λ=254 nm, one peak for two diastereoisomers with t$_R$=16.39 min.

Example 27—In Vitro Cytotoxicity Analyses

A subset of compounds of the invention were assayed for their cytotoxic activity in an array of different solid tumours and haematological malignancies using the following assay.

Solid Tumour and Haematological Malignancy Assay.

In vitro viability assay were performed to assess the effects of compounds on cell viability in selected cell lines over 72 h using the CellTiterGlo (CTG, Promega-G7573) assay. The tests were performed in duplicates with treatment of compounds at 9 points, 3.16 folds titration in 96 well plates over ~72 h. The compound starting concentrations were 198 μM. Cell viability assay using CellTiterGlo in 96-well plate were performed. Compound treatment 72 h, standard growth conditions, duplicates. Compounds were dissolved to 40 mM with thawed 100%. Compounds were serially diluted at 3.16 fold in thawed DMSO, and warmed to 37° C. before being dissolved in media (2 μL+200 μL). After compounds were dissolved in media, media containing compounds were warmed to 37° C. in incubator and then compounds in media were added to cell plates (50 μL+50 μL) in duplicates. The compounds' final concentrations were from 198 μM to 19.8 nM. All compound solubilities were checked and recorded again, then the plates were transferred to CO$_2$ tissue culture incubator immediately and incubated for 3 days. DMSO final concentration is 0.5%. The parent nucleoside in each case was tested as a comparator, as was an exemplary ProTide. The drugs of the ProTide class that were tested were as follows:

A

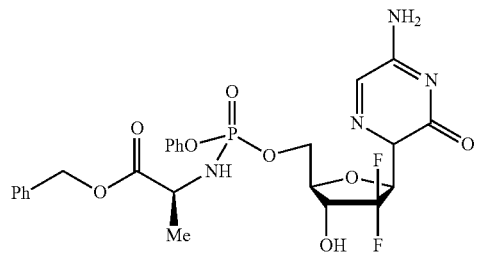

B

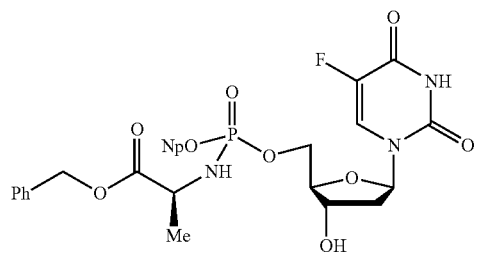

C

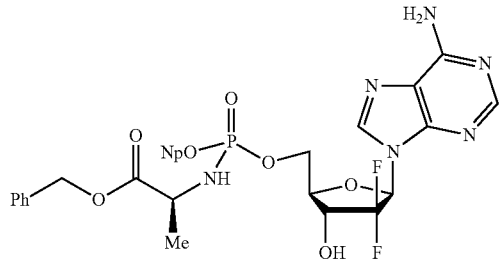

D

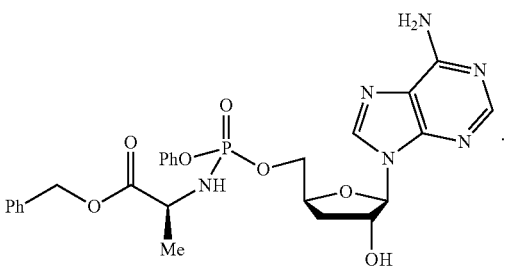

E

The following cell lines were tested and are referred to in the Table 1 below:

TABLE 1

| Cell line | Malignancy | Cell line | Malignancy |
|---|---|---|---|
| MOLT-4 | Acute T lymphoblastic leukaemia | MCF-7 | Breast adenocarcinoma |
| CCRF-CEM | Acute lymphoblastic leukaemia | HL-60 | Promyelocytic leukaemia |
| RL | Non-Hodgkin's lymphoma | MV4-11 | Biphenotypic B myelomonocytic leukaemia |
| RPMI-8226 | Human multiple myeloma | HepG2 | Hepatocellular carcinoma |
| K562 | Chronic myelogenous leukaemia | HT29 | Colon adenocarcinoma |
| OVCAR-3 | Ovarian adenocarcinoma | Mia-Pa-Ca-2 | Pancreatic carcinoma |

TABLE 1-continued

| Cell line | Malignancy | Cell line | Malignancy |
|---|---|---|---|
| KG-1 | Acute myelogenous leukaemia | | |

The results of this screening are presented in Tables 2, 3 and 4.

In Table 3, A represents an $EC_{50}$ of no more than 0.2 μm; B represents an $EC_{50}$ of greater than 0.2 μm but no more than 2 μm; C represents an $EC_{50}$ of greater than 2 μm but no more than 5 μm; D represents an $EC_{50}$ of greater than 5 μm but no more than 10 μm; and E represents an $EC_{50}$ of greater than 10 μm. No entry means that screening of the indicated compound against the indicated cell line was not carried out.

In Table 4, A represents an $EC_{50}$ of no more than 0.2 μm; B represents an $EC_{50}$ of greater than 0.2 μm but no more than 1 μm; C represents an $EC_{50}$ of greater than 1 μm but no more than 5 μm; D represents an $EC_{50}$ of greater than 5 μm but no more than 10 μm; and E represents an $EC_{50}$ of greater than 10 μm. Letters in bold represent an $EC_{50}$ less than that of the exemplary ProTide A.

In Tables 2, 3 and 4, 'Ab $EC_{50}$' refers to the absolute EC50 and 'Top inhibit' refers to the percentage inhibition achieved at the highest concentration tested.

TABLE 2

| | Mia-Pa-Ca-2 | | HT29 | | HepG2 | | OVCAR 3 | | MCF-7 | |
|---|---|---|---|---|---|---|---|---|---|---|
| Compound | Ab $EC_{50}$ (μM) | Top Inhibit (%) | Ab $EC_{50}$ (μM) | Top Inhibit (%) | Ab $EC_{50}$ (μM) | Top Inhibit (%) | Ab $EC_{50}$ (μM) | Top Inhibit (%) | Ab $EC_{50}$ (μM) | Top Inhibit (%) |
| Gemcitabine | 0.03 | 79 | 0.22 | 65 | 28.0 | 54 | >198 | 44 | 0.011 | 53 |
| 8 | 0.07 | 79 | 0.48 | 62 | 83.13 | 52 | >198 | 48.5 | 0.07 | 52 |
| B | 0.53 | 82 | 8.55 | 62 | 21.33 | 57 | >198 | 33.5 | 2.71 | 54 |
| FUDR | 0.35 | 90 | 0.22 | 82 | 84.02 | 61 | 2.32 | 66 | 7.23 | 73 |
| 4 | 0.11 | 67 | 0.25 | 77 | >198 | 48 | 2.81 | 67.5 | 15.80 | 66 |
| C | 1.01 | 89 | 1.91 | 81 | 70.60 | 65 | — | — | 27.25 | 89 |
| 8-Cl-Adenosine | 0.42 | 85 | 1.96 | 73 | — | — | — | — | 1.83 | 85.7 |
| 5 | 0.43 | 87.6 | 1.41 | 76.5 | — | — | — | — | 1.69 | 88 |
| D | 1.97 | 99.7 | 3.82 | 94 | — | — | — | — | 4.30 | 99.6 |
| Cordycepin | 84.73 | 88 | 32.74 | 87 | — | — | — | — | — | — |
| 7 | 3.32 | 98.90 | 7.79 | 79 | — | — | — | — | — | — |
| 6 | 40.89 | 95.7 | 24.34 | 82 | — | — | — | — | — | — |
| E | 7.92 | 98 | 10.75 | 97 | — | — | — | — | — | — |

| | CCRF-CEM | | MOLT-4 | | K562 | | HL-60 | | RL | | RPMI-8226 | |
|---|---|---|---|---|---|---|---|---|---|---|---|---|
| Compound | Ab $EC_{50}$ (μM) | Top Inh (%) | Ab $EC_{50}$ (μM) | Top Inh (%) | Ab $EC_{50}$ (μM) | Top Inh (%) | Ab $EC_{50}$ (μM) | Top Inh (%) | Ab $EC_{50}$ (μM) | Top Inh (%) | Ab $EC_{50}$ (μM) | Top Inh (%) |
| Gemcitabine | 0.02 | 101 | 0.004 | 88 | — | — | — | — | — | — | — | — |
| 8 | 0.04 | 99.9 | 0.009 | 84 | >198 | 29 | 0.08 | 98 | 0.20 | 66.5 | — | — |
| B | — | — | 0.24 | 76.4 | — | — | — | — | — | — | — | — |
| FUDR | 0.04 | 91.9 | — | — | — | — | — | — | — | — | 0.11 | 99 |
| 4 | 0.03 | 97.1 | — | — | — | — | — | — | — | — | 0.05 | 95 |
| C | — | — | — | — | — | — | — | — | — | — | — | — |
| 8-Cl-Adenosine | — | — | — | — | — | — | — | — | — | — | — | — |
| 5 | — | — | — | — | — | — | — | — | — | — | — | — |
| D | — | — | — | — | — | — | — | — | — | — | — | — |
| Cordycepin | — | — | 100.65 | 76.5 | 117.51 | 94 | 117.58 | 56 | >198 | 16.6 | >198 | 17 |
| 7 | — | — | 25.30 | 90 | 9.16 | 94 | 6.97 | 100 | 11.10 | 93 | 1.60 | 98 |
| 6 | — | — | 14.19 | 95 | 52.28 | 81 | 62.50 | 80 | 88.81 | 72 | — | — |
| E | — | — | 5.23 | 96 | 10.95 | 87 | 31.13 | 97 | 18.29 | 90.5 | 19.89 | 97.8 |

TABLE 3

| | HT29 | | HepG2 | | OVCAR 3 | | MCF-7 | |
|---|---|---|---|---|---|---|---|---|
| Compound | Ab $EC_{50}$ (μM) | Top Inhibit (%) | Ab $EC_{50}$ (μM) | Top Inhibit (%) | Ab $EC_{50}$ (μM) | Top Inhibit (%) | Ab $EC_{50}$ (μM) | Top Inhibit (%) |
| Clofarabine | B | 64 | C | 64 | E | 48 | B | 55 |
| 1 | B | 66 | — | — | E | — | B | 59 |
| 2 | B | 62 | — | — | E | 48 | B | 54 |
| 3 | B | 61 | C | 53 | E | 49 | C | 59 |
| A | C | 94 | — | — | — | — | D | 99.6 |

TABLE 3-continued

| Compound | CCRF-CEM Ab EC$_{50}$ (μM) | Top Inh (%) | MOLT-4 Ab EC$_{50}$ (μM) | Top Inh (%) | K562 Ab EC$_{50}$ (μM) | Top Inh (%) | HL-60 Ab EC$_{50}$ (μM) | Top Inh (%) | RL Ab EC$_{50}$ (μM) | Top Inh (%) | RPMI-8226 Ab EC$_{50}$ (μM) | Top Inh (%) |
|---|---|---|---|---|---|---|---|---|---|---|---|---|
| Clofarabine | A | 98.7 | A | 84.1 | E | 23 | A | 97 | B | 77 | D | 89 |
| 1 | A | 98.7 | A | 82.7 | E | 24 | A | 97 | B | 70 | D | 91 |
| 2 | A | 98.7 | A | 98 | E | 29 | A | 98 | B | 65 | D | 92 |
| 3 | A | 99.6 | A | 96 | E | 24 | A | 97 | B | 63 | D | 91.6 |
| A | A | 99.4 | B | 93 | E | 32 | B | 97 | C | 99.8 | C | 97 |

TABLE 4

| Compound | HT29 Ab EC$_{50}$ (μM) | Top Inhibit % | HepG2 Ab EC$_{50}$ (μM) | Top Inhibit % | MCF-7 Ab EC$_{50}$ (μM) | Top Inhibit % | MOLT-4 Ab EC$_{50}$ (μM) | Top Inhibit % |
|---|---|---|---|---|---|---|---|---|
| Clofarabine | B | 68 | C | 57 | B | 54 | A | 94 |
| A | C | 86 | D | 99 | D | 99 | B | 100 |
| 9 | B | 70 | B | 53 | — | 45 | A | 92 |
| 10 | B | 70 | C | 55 | E | 51 | A | 93 |
| 11 | B | 69 | C | 58 | E | 57 | A | 91 |
| 12 | 0.37 | 71 | 0.29 | 54 | — | 44 | 0.04 | 91 |
| 13 | B | 68 | — | 49 | — | 49 | A | 89 |
| 14 | B | 71 | B | 52 | — | 48 | A | 95 |
| 15 | 0.33 | 69 | 0.37 | 51 | — | 47 | 0.03 | 90 |
| 16 | B | 71 | B | 53 | — | 47 | A | 97 |
| 17 | B | 69 | B | 52 | — | 46 | A | 88 |
| 18 | B | 66 | B | 53 | — | 44 | A | 88 |
| 19 | B | 68 | B | 51 | — | 47 | A | 90 |
| 20 | B | 69 | B | 54 | — | 48 | A | 89 |
| 21 | B | 69 | B | 53 | — | 49 | A | 90 |
| 22 | B | 69 | — | 47 | — | 50 | A | 89 |
| 23 | B | 68 | C | 51 | — | 48 | A | 89 |
| 24 | B | 70 | C | 54 | — | 49 | A | 88 |
| 25 | B | 67 | — | 49 | — | 43 | A | 86 |
| 26 | B | 64 | — | 49 | — | 44 | A | 84 |

| Compound | OVCAR 3 Ab EC$_{50}$ (μM) | Top Inhibit % | CCRF-CEM Ab EC$_{50}$ (μM) | Top Inhibit % | K 562 Ab EC$_{50}$ (μM) | Top Inhibit % | HL-60 Ab EC$_{50}$ (μM) | Top Inhibit % |
|---|---|---|---|---|---|---|---|---|
| Clofarabine | E | 42 | A | 99 | E | 32 | A | 97 |
| A | E | 94 | A | 99 | E | 85 | B | 97 |
| 9 | E | 43 | A | 99 | E | 40 | A | 96 |
| 10 | E | 42 | A | 99 | E | 37 | A | 96 |
| 11 | E | 70 | A | 99 | E | 50 | A | 96 |
| 12 | >198 | 41 | <0.02 | 99 | >198 | 40 | 0.07 | 96 |
| 13 | E | 80 | A | 99 | E | 44 | A | 96 |
| 14 | E | 43 | A | 99 | E | 36 | A | 96 |
| 15 | >198 | 41 | <0.02 | 99 | >198 | 36 | 0.06 | 96 |
| 16 | E | 44 | A | 99 | E | 33 | A | 96 |
| 17 | E | 47 | A | 99 | E | 37 | A | 96 |
| 18 | E | 47 | A | 99 | E | 40 | A | 96 |
| 19 | E | 51 | A | 99 | E | 37 | A | 95 |
| 20 | E | 49 | A | 99 | E | 35 | A | 96 |
| 21 | E | 47 | A | 99 | E | 32 | A | 96 |
| 22 | E | 73 | A | 99 | E | 62 | A | 95 |
| 23 | E | 63 | A | 99 | E | 35 | A | 96 |
| 24 | E | 67 | A | 99 | E | 49 | A | 95 |
| 25 | E | 24 | A | 99 | E | 33 | A | 95 |
| 26 | E | 62 | A | 99 | E | 69 | A | 95 |

TABLE 4-continued

| | KG-1 | | RL | | RPMI-8226 | |
|---|---|---|---|---|---|---|
| Compound | Ab EC$_{50}$ (μM) | Top Inhibit % | Ab EC$_{50}$ (μM) | Top Inhibit % | Ab EC$_{50}$ (μM) | Top Inhibit % |
| Clofarabine | A | 93 | B | 61 | E | 80 |
| A | B | 93 | C | 90 | C | 94 |
| 9 | A | 92 | B | 53 | E | 81 |
| 10 | A | 92 | — | 48 | E | 80 |
| 11 | A | 92 | — | 47 | E | 81 |
| 12 | 0.14 | 91 | — | 47 | 39.55 | 79 |
| 13 | A | 93 | — | 48 | E | 88 |
| 14 | A | 93 | — | 49 | E | 78 |
| 15 | 0.09 | 92 | — | 49 | 30.28 | 80 |
| 16 | A | 93 | — | 49 | E | 84 |
| 17 | A | 92 | — | 48 | E | 82 |
| 18 | A | 91 | — | 48 | E | 84 |
| 19 | A | 92 | B | 57 | E | 79 |
| 20 | A | 92 | B | 69 | E | 80 |
| 21 | A | 92 | C | 70 | E | 81 |
| 22 | A | 92 | — | 42 | C | 86 |
| 23 | A | 93 | — | 39 | E | 85 |
| 24 | A | 91 | — | 39 | E | 86 |
| 25 | A | 91 | — | 44 | C | 83 |
| 26 | A | 91 | E | 56 | C | 93 |

As can be seen from Tables 3 and 4, certain compounds of the invention were more active than the ProTide A against a range of different cancer cell lines.

Example 28—Metabolic Stability

The assay was performed according to the published procedure (Kuhnz, W.; Gieschen, H. *Drug Metab. Dispos.* 1998, 26, 1120-1127).

Pooled cryopreserved hepatocytes were thawed, washed, and re-suspended in Krebs-Henseleit buffer (pH 7.3). The reaction was initiated by adding the test compound (1 μM final concentration) into cell suspension and incubated in a final volume of 100 μL on a flat-bottom 96-well plate for 0 and 120 min, respectively, at 37° C./5% CO$_2$. The reaction was stopped by adding 100 μL of acetonitrile into the incubation mixture. Samples were then mixed gently and briefly on a plate shaker, transferred completely to a 0.8 mL V-bottom 96-well plate, and centrifuged at 2500×g for 15 min at room temperature. Each supernatant (150 μL) was transferred to a clean cluster tube, followed by HPLC-MS/MS analysis on a Thermo Electron triplequadrupole system.

For comparison, the parent nucleoside and a corresponding ProTide were tested in the same assay The results are shown in Tables 5 and 6:

TABLE 5

| Compound | Human hepatocytes Mean half-life (min.) |
|---|---|
| D | 53 |
| 5 | 18 |
| 8-Cl-Adenosine | >120 |
| B | 139 |
| 8 | 27 |
| Gemcitabine | — |
| C | 24 |
| 4 | 15 |
| FUDR | 69 |
| E | 90 |
| 7 | 27 |
| Cordycepin | 48 |

TABLE 6

| Compound | Human hepatocytes Mean half-life (min.) |
|---|---|
| A | 24 |
| 1 | In the range 20 to 100 |
| 2 | In the range 20 to 100 |
| 3 | In the range 20 to 100 |
| Clofarabine | >120 |

Example 29—Evaluation of Clofarabine and Selected Clofarabine Diphosphate Phosphoramidates in a KG1a Cell Line Model of Acute Myeloid Leukaemia (AML)

Summary

Clofarabine and Examples 1 and 2 were selected for analysis to determine whether: (1) the compounds of the invention possessed increased potency when compared to the parental compound and (2) the compounds of the invention preferentially targeted leukaemic stem cells (LSCs). In order to establish this, the acute myeloid leukaemia cell line, KG1a, was employed as it manifests a minor stem cell-like compartment with a distinct immunophenotype (Lin$^-$/CD34$^+$/CD38$^-$/CD123$^+$). The compounds were evaluated over an extended dose range. In addition, the effects of the compounds on the stem cell compartment were evaluated over the entire dose range. The mean clofarabine LD$_{50}$ (the concentration of drug required to kill 50% of the cells) was 1.69×10$^{-8}$M. Example 1 showed a similar mean LD$_{50}$ value (1.37×10$^{-8}$M), whereas Example 2 showed significantly increased mean LD$_{50}$ values (4.38×10$^{-8}$M and 7.10×10$^{-8}$M respectively).

Under normoxic conditions, the LSC (Lin$^-$/CD34$^+$/CD38$^-$/CD123$^+$) compartment constituted ~3.5% of the total cell line. However, under hypoxic conditions (1% and 5% oxygen) the proportion of LSCs showed a time-dependent increase (up to 23.7%). Furthermore, this was reversed when the cell line was transferred back into normoxic conditions. There was no significant difference in the fraction of LSCs in the cultures between 1% and 5% oxygen.

When considering the relative potency of the compounds under normoxic and hypoxic conditions (5% oxygen), clofarabine showed a significant increase in mean $LD_{50}$ under hypoxic conditions ($1.69\times10^{-8}$M to $5.31\times10^{-8}$M; P=0.01). In contrast, Example 1 showed no significant difference in mean $LD_{50}$ values.

Objectives
1. To generate a complete cytotoxicity dose-response curve for a series of selected compounds and their respective parental nucleoside in KG1a cells
2. To establish the effects of the tested compounds on the LSC compartment over the entire range of concentrations used
3. To compare the effects of the tested compounds under hypoxic conditions (1% and 5% oxygen)
4. To investigate the persistence of γH2A.X foci in LSCs and bulk tumour cells following treatment with clofarabine and the tested compounds under hypoxic conditions Materials and Methods KG1a Cell Culture Conditions The acute myeloid leukaemia (AML) KG1a cell line was maintained in RPMI medium (Invitrogen, Paisley, UK) supplemented with 100 units/mL penicillin, 100 μg/mL streptomycin and 20% foetal calf serum. Cells were subsequently aliquoted ($10^5$ cells/100 μL) into 96-well plates and were incubated at 37° C. in a humidified normoxic (20% oxygen) or hypoxic (1% or 5% oxygen) atmosphere for 48 h in the presence of clofarabine, or clofarabine diphosphate phosphoramidates of the invention ($1\times10^{-10}$M-$1\times10^{-6}$M). In addition, control cultures were carried out to which no drug was added. Cells were subsequently harvested by centrifugation and were analysed by flow cytometry using the Annexin V assay.

Measurement of In Vitro Apoptosis

Cultured cells were harvested by centrifugation and then resuspended in 195 μL of calcium-rich buffer. Subsequently, 5 μL of Annexin V (Caltag Medsystems, Botolph Claydon, UK) was added to the cell suspension and cells were incubated in the dark for 10 mins prior to washing. Cells were finally resuspended in 190 μL of calcium-rich buffer together with 10 μL of propidium iodide. Apoptosis was assessed by dual-colour immunofluorescent flow cytometry as described previously. Subsequently $LD_{50}$ values (the dose required to kill 50% of the cells in a culture) were calculated for each nucleoside analogue and diphosphate phosphoramidate.

Immunophenotypic Identification of the Leukaemic Stem Cell Compartment

KG1a cells were cultured for 48 h in the presence of a wide range of concentrations of each nucleoside analogue and their respective diphosphate phosphramidate. Cells were then harvested and labelled with a cocktail of anti-lineage antibodies (PE-cy7), anti-CD34 (FITC), anti-CD38 (PE) and anti-CD123 (PERCP cy5). The sub-population expressing a leukaemic stem cell (LSC) phenotype were subsequently identified and were expressed as a percentage of all viable cells left in the culture. The percentages of stem cells remaining were then plotted on a dose-response graph and the effects of the diphosphate phosphoramidate were compared with the parental nucleosides.

Cell Sorting

KG1a cells were grown under hypoxic conditions for 7 days in order to generate $10^7$ cells and increase the percentage of cells expressing an LSC phenotype. Subsequently, $Lin^-/CD34^+/CD38^-/CD123^+$ LSCs and $Lin^-/CD34^+/CD38^+/CD123^+$ 'bulk' tumour cells were purified by high speed cell sorting using a FACS Melody cell sorter (Becton Dickenson) and were placed back into hypoxic cell culture conditions prior to the addition of clofarabine or clofarabine diphosphate phosphoramidates.

γH2A.X Phosphorylation Assay

Phosphorylation of the histone variant γH2A.X occurs as a rapid response to double strand DNA breaks. The γH2A.X Phosphorylation Assay Kit (Flow cytometry) is a cell-based assay formatted for flow cytometric detection of levels of phosphorylated Histone γH2A.X (Merck, UK). LSC and 'bulk tumour' cells were cultured in 96-well plates in the presence of clofarabine or clofarabine diphosphate phosphoramidates. After 2 h of exposure to drug, the cells were harvested by centrifugation and then fixed and permeabilised in preparation for staining and detection. Histone γH2A.X phosphorylated at serine 139 is detected by the addition of the anti-phospho-Histone γH2A.X conjugated to APC. Cells were then run on a flow cytometer to quantitate the number of cells staining positive for phosphorylated Histone γH2A.X.

Statistical Analysis

The data obtained in these experiments were evaluated using one-way ANOVA. All data was confirmed as Gaussian or a Gaussian approximation using the omnibus K2 test. $LD_{50}$ values were calculated from the non-linear regression and line of best-fit analysis of the sigmoidal dose-response curves. All statistical analyses were performed using Graphpad Prism 6.0 software (Graphpad Software Inc., San Diego, Calif.).

Results

In Vitro Cytotoxicity Assay

The in vitro drug sensitivity of KG1a cells was assessed using the Annexin V/propidium iodide assay. The sigmoidal dose-response curves for each compound tested are shown in FIG. 1A-C. The results are summarised in Table 7.

TABLE 7

| Compound | Mean $LD_{50}$ (nM) |
| --- | --- |
| Clofarabine | 16.9 |
| Example 1 | 13.7 |
| Example 2 | 71.0 |

Clofarabine and the compounds of the invention showed potency in the nanomolar range; clofarabine and Example 1 had similar $LD_{50}$ values with Example 1 being slightly more potent.

The Fraction of KG1a Cells Expressing an LSC Phenotype is Modulated by Hypoxia

Figure 3:
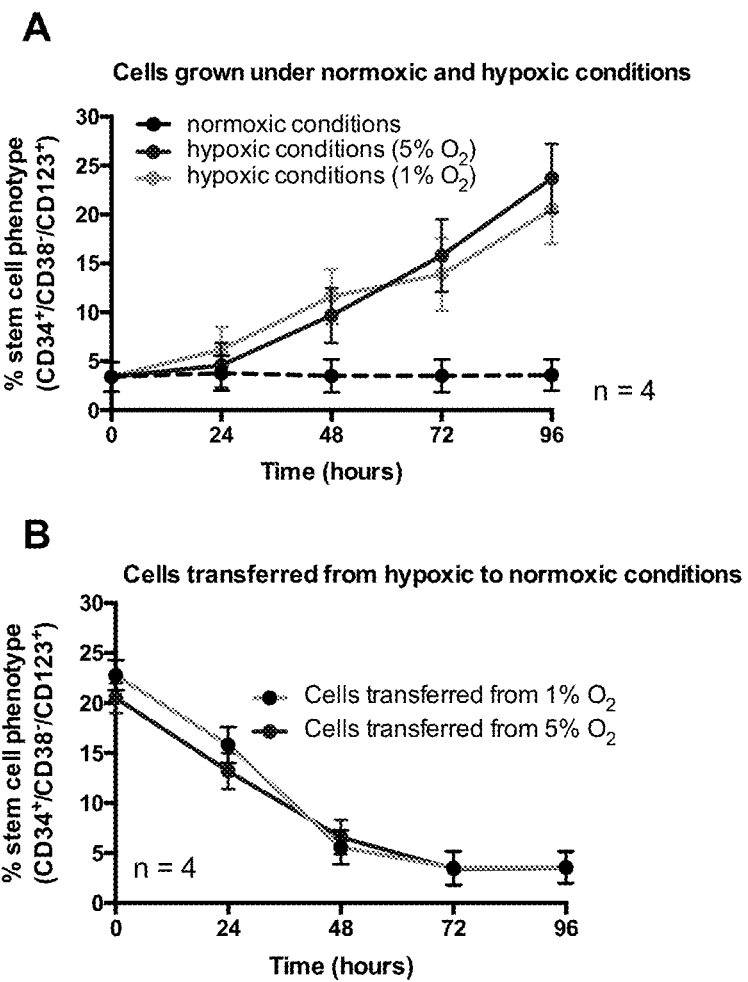
FIG. 3 shows comparison of the fraction of KG1a cells expressing an LSC phenotype under normoxic and hypoxic conditions. (A) KG1a cells show a time-dependent increase in cells expressing an LSC phenotype under hypoxic conditions, which was (B) reversed when the cells were transferred into normoxic culture conditions. All data are the mean (±SD) of four independent experiments.

KG1a cells were grown under normoxic and hypoxic conditions and the LSC phenotype was monitored over time. Under normoxic conditions, the LSC phenotype was stably maintained in approximately 3.5% of the cells in culture. In contrast, under hypoxic conditions, the fraction of the cells in culture expressing the LSC phenotype increased in a time-dependent manner (FIG. 3A). When cells were then transferred back into normoxic culture conditions, the fraction of cells expressing the LSC phenotype returned to ~3.5%, again in a time-dependent manner (FIG. 3B).

Figure 4:
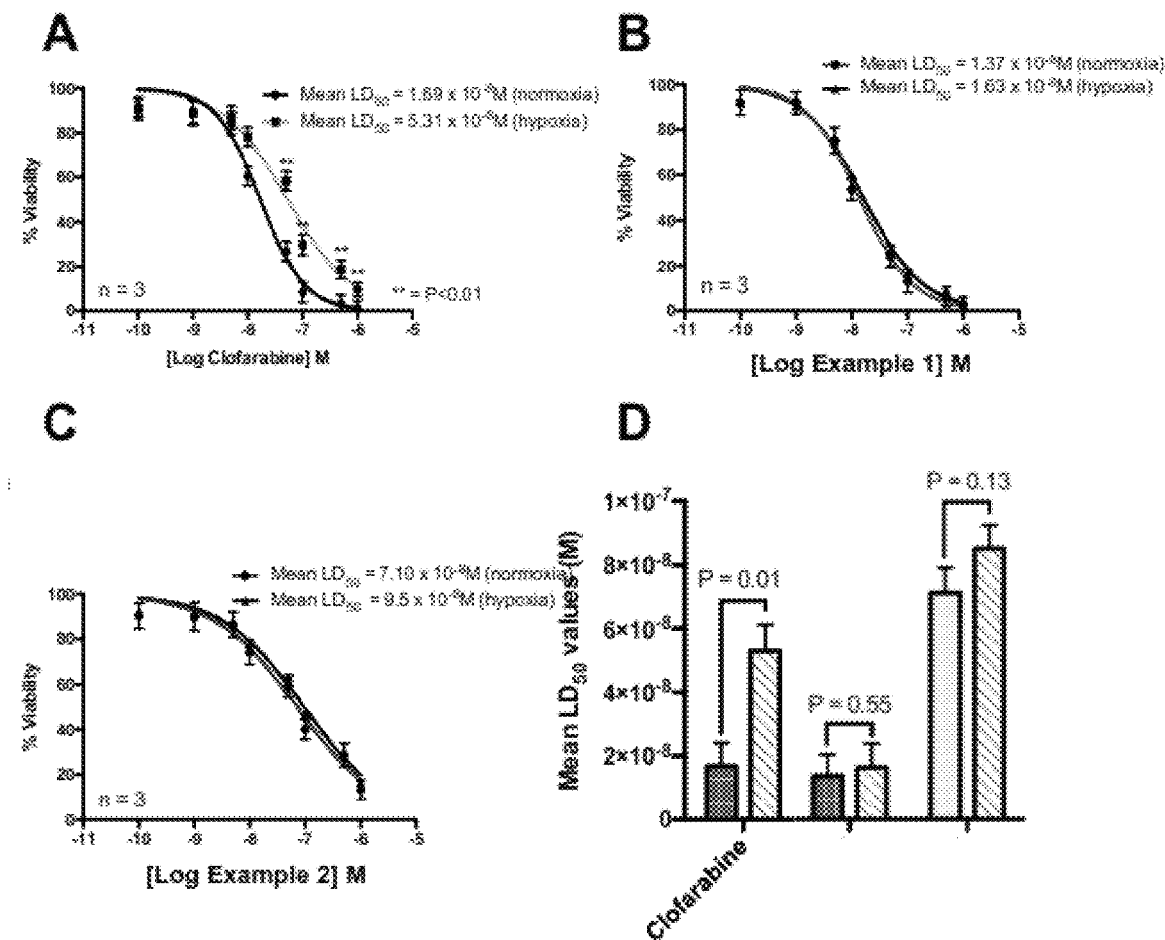
FIG. 4 shows comparison of the mean $LD_{50}$ values for (A) clofarabine, (B) Example 1, and (C) Example 2 under normoxic and hypoxic conditions. Clofarabine showed a significant loss in potency under hypoxic conditions. In contrast, the compounds of the invention maintained their potency under hypoxic conditions. All data are the mean (±SD) of three independent experiments.

Comparison of Clofarabine and Compounds of the Invention Under Normoxic and Hypoxic Conditions Given the observed increase in an LSC phenotype under hypoxic conditions, the relative potency of clofarabine and the compounds was assessed in KG1a cells cultured under normoxic and hypoxic (5% $O_2$) conditions. FIG. 4 shows the overlaid sigmoidal dose-response curves for clofarabine and the compounds of the invention. The results are summarised in Table 8:

| Compound | Normoxia Mean LD$_{50}$ (nM) | Hypoxia Mean LD$_{50}$ (nM) | Ratio Normoxia/Hypoxia |
|---|---|---|---|
| Clofarabine | 16.9 | 53.1 | 31.8 |
| Example 1 | 13.7 | 16.3 | 84.0 |
| Example 2 | 71.0 | 95.0 | 74.7 |

As can be seen, clofarabine showed a significant reduction in potency when used on cells cultured under hypoxic conditions. This reduction in potency was not observed when Examples 1 and 2 were used under the same hypoxic conditions.

Clofarabine Induces Significantly Less DNA Damage in LSCs than Bulk Tumour Cells Under Hypoxic Conditions In an attempt to understand why clofarabine-treated cells were less sensitive to the effects of the drug under hypoxic conditions, cells were grown under hypoxic conditions and then the LSC and bulk tumour fractions were purified using high-speed cell sorting. The purified cells were then exposed to drug for 2 hours and the amount of DNA damage was quantified using a γH2A.X phosphorylation assay. FIG. 5 shows that the level of DNA damage in the LSCs was significantly lower than the bulk tumour cells following treatment with clofarabine. In contrast, Examples 1 and 2 induced similar levels of DNA damage in both the LSCs and the bulk tumour cells.

1. In terms of stem cell targeting, all of the compounds tested showed evidence of stem cell targeting at concentrations above $10^{-8}$M. Example 1 showed a trend towards increased selectivity against Lin$^-$/CD34$^+$/CD38$^-$/CD123$^+$ LSCs.
2. The LSC phenotype was shown to be inducible under hypoxic conditions and this was reversed when the cells were reintroduced to normoxic culture conditions. The dynamics of the changes in LSC fraction suggests a plasticity in the phenotype rather than a selective expansion/contraction in a fixed LSC sub-population.
3. Clofarabine showed a significant reduction in potency when used on cells cultured under hypoxic conditions. This reduction in potency was not observed when Examples 1 and 2 were used under the same hypoxic conditions. Many cancers exist in a hypoxic state in the human body.
4. One explanation for the reduced clofarabine potency under hypoxic conditions is that there is a significant expansion of the LSC fraction under these conditions and LSCs showed significantly lower DNA damage, as measured by phosphorylation of γH2A.X, following short-term exposure to clofarabine. In contrast, Examples 1 and 2 induced similar levels of DNA damage in the bulk tumour cells and LSCs under the same conditions.

The invention claimed is:

1. A compound of formula (I), or a pharmaceutically acceptable salt thereof:

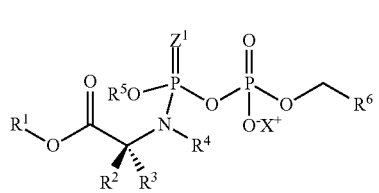

(I)

wherein

R$^1$ is selected from: C$_1$-C$_{24}$-alkyl, C$_3$-C$_{24}$-alkenyl, C$_3$-C$_{24}$-alkynyl, C$_0$-C$_4$-alkylene-C$_3$-C$_8$-cycloalkyl and C$_0$-C$_4$-alkylene-aryl;

R$^2$ and R$^3$ are independently selected from H, C$_1$-C$_6$-alkyl and C$_1$-C$_3$-alkylene-R$^7$; or R$^2$ and R$^3$ together with the atom to which they are attached form a 3- to 6-membered cycloalkyl or heterocycloalkyl group;

R$^4$ is selected from H or C$_1$-C$_4$-alkyl;

or R$^4$ is joined with a group selected from R$^2$ and R$^3$ to form a 3- to 6-membered heterocycloalkyl group;

R$^5$ is selected from aryl, 5-, 6-, 9- or 10-membered heteroaryl, C$_3$-C$_8$-cycloalkyl, 3- to 7-membered heterocycloalkyl, C$_1$-C$_3$-alkylene-R$^{5a}$ and C$_1$-C$_8$-alkyl, and wherein the aryl may be optionally fused to C$_6$-C$_8$-cycloalkyl;

R$^{5a}$ is selected from aryl, 5-, 6-, 9- or 10-membered heteroaryl, C$_3$-C$_8$-cycloalkyl, and 3- to 7-membered heterocycloalkyl, wherein the aryl may be optionally fused to C$_6$-C$_8$-cycloalkyl;

R$^6$ is selected from:

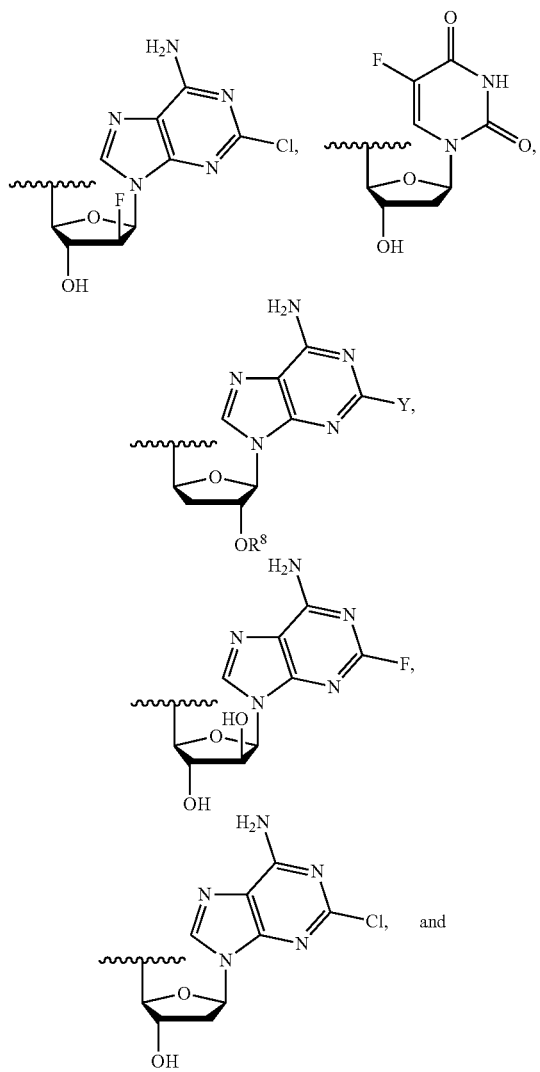

-continued

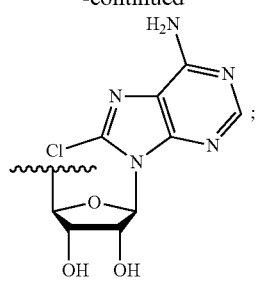

R⁷ is selected from aryl, imidazole, indole, $SR^a$, $OR^a$, $CO_2R^a$, $CO_2NR^aR^a$, $NR^aR^b$ and $NH(=NH)NH_2$;

R⁸ is selected from H and

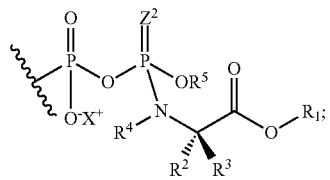

$Z^1$ and $Z^2$ are each independently selected from O and S;

Y is selected from H, F, Cl and OMe;

X is at each occurrence a pharmaceutically acceptable cation;

wherein any aryl group is either phenyl or naphthyl;

wherein where any of $R^1$, $R^2$, $R^3$, $R^4$, $R^5$ or $R^7$ is an alkyl, cycloalkyl, heterocycloalkyl, aryl or heteroaryl, that alkyl, cycloalkyl, heterocycloalkyl, aryl or heteroaryl group is optionally substituted with from 1 to 4 substituents selected from: halo, nitro, cyano, $NR^aR^a$, $NR^aS(O)_2R^a$, $NR^aC(O)R^a$, $NR^aCONR^aR^a$, $NR^aCO_2R^a$, $OR^a$, $SR^a$, $SOR^a$, $SO_3R^a$, $SO_2R^a$, $SO_2NR^aR^a$, $CO_2R^a$, $C(O)R^a$, $CONR^aR^a$, $CR^aR^a$ $NR^aR^a$, $C_1$-$C_4$-alkyl, $C_2$-$C_4$-alkenyl, $C_2$-$C_4$-alkynyl and $C_1$-$C_4$-haloalkyl;

wherein $R^a$ is independently at each occurrence selected from: H and $C_1$-$C_4$-alkyl; and $R^b$ is independently at each occurrence selected from: H, and $C_1$-$C_4$-alkyl and $C(O)$—$C_1$-$C_4$-alkyl.

2. The compound of claim 1, wherein $R^4$ is H.

3. The compound of claim 1, wherein $R^6$ is

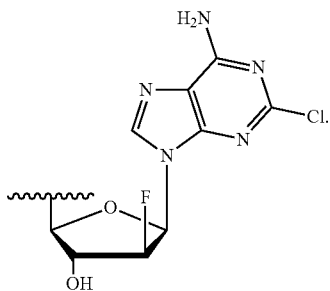

4. The compound of claim 1, wherein $R^6$ is

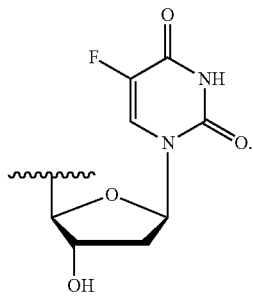 [SMILES: *[C@H]1O[C@@H](n2cc(F)c(=O)[nH]c2=O)C[C@H]1O]

5. The compound of claim 1, wherein $R^6$ is

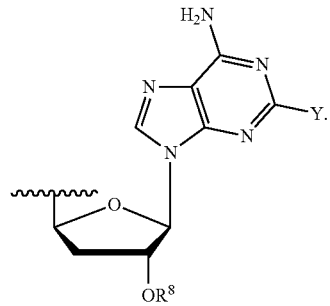

6. The compound of claim 5, wherein Y is H.

7. The compound of claim 5, wherein Y is F.

8. The compound of claim 5, wherein $R^8$ is H.

9. The compound of claim 5, wherein $R^8$ is

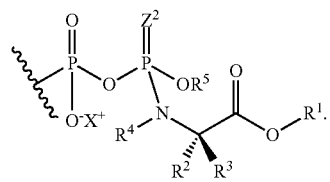

10. The compound of claim 9, wherein $Z^2$ is O.

11. The compound of claim 9, wherein $Z^2$ is S.

12. The compound of claim 1, wherein R⁶ is

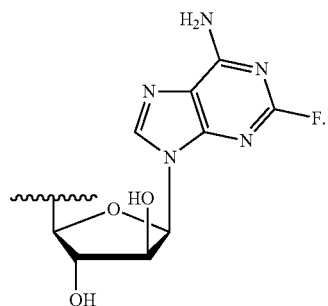

13. The compound of claim 1, wherein R⁶ is

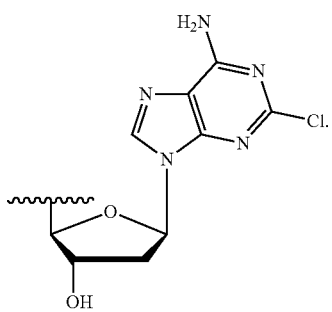 [SMILES: *[C@H]1O[C@@H](n2cnc3c(N)nc(Cl)nc32)C[C@H]1O]

14. The compound of claim 1, wherein R⁶ is

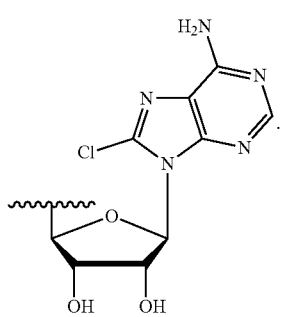

15. The compound of claim 1, wherein $R^1$ is selected from $C_5$-$C_7$-cycloalkyl, $C_1$-$C_8$-alkyl and benzyl.

16. The compound of claim 15, wherein $R^1$ is benzyl.

17. The compound of claim 15, wherein $R^1$ is $C_1$-$C_8$-alkyl.

18. The compound of claim 1, wherein $R^3$ is H.

19. The compound of claim 1, wherein $R^2$ is $C_1$-$C_4$-alkyl.

20. The compound of claim 1, wherein $R^2$ is H.

21. The compound of claim 1, wherein $R^5$ is phenyl.

22. The compound of claim 1, wherein $R^5$ is naphthyl.

23. The compound of claim 1, wherein the compound is selected from:

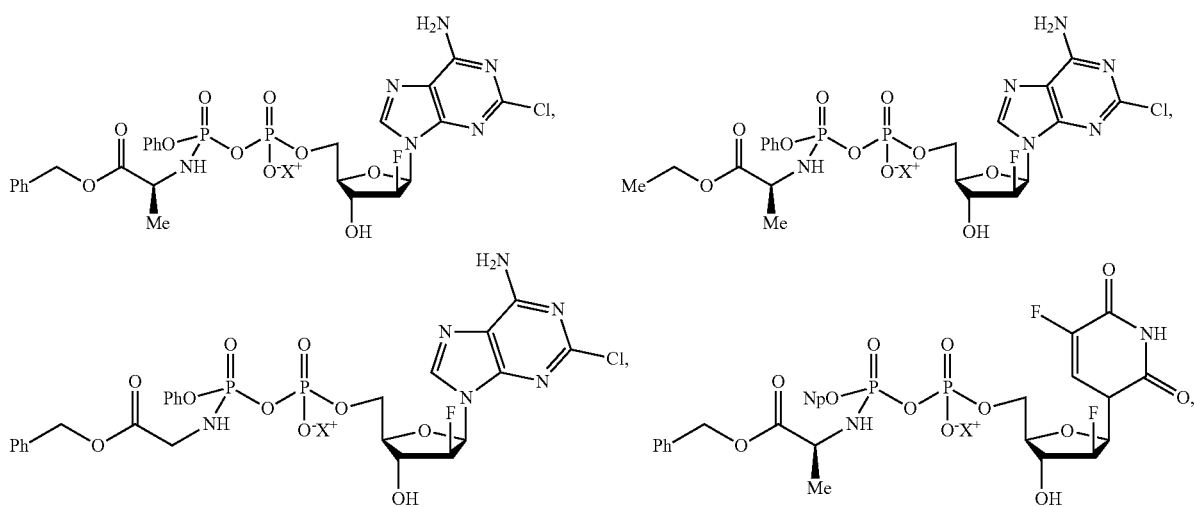

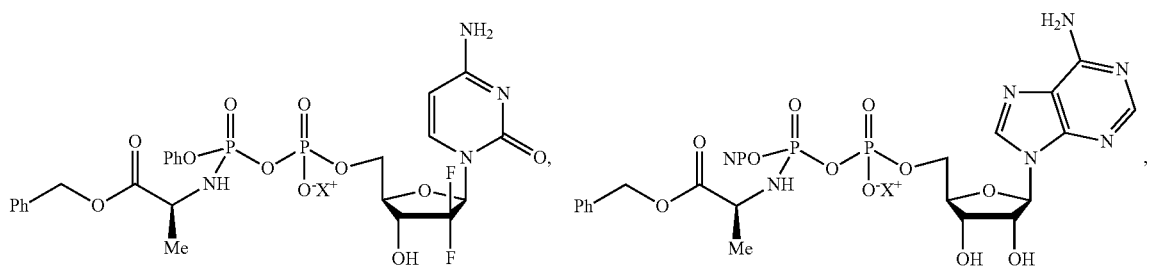

-continued
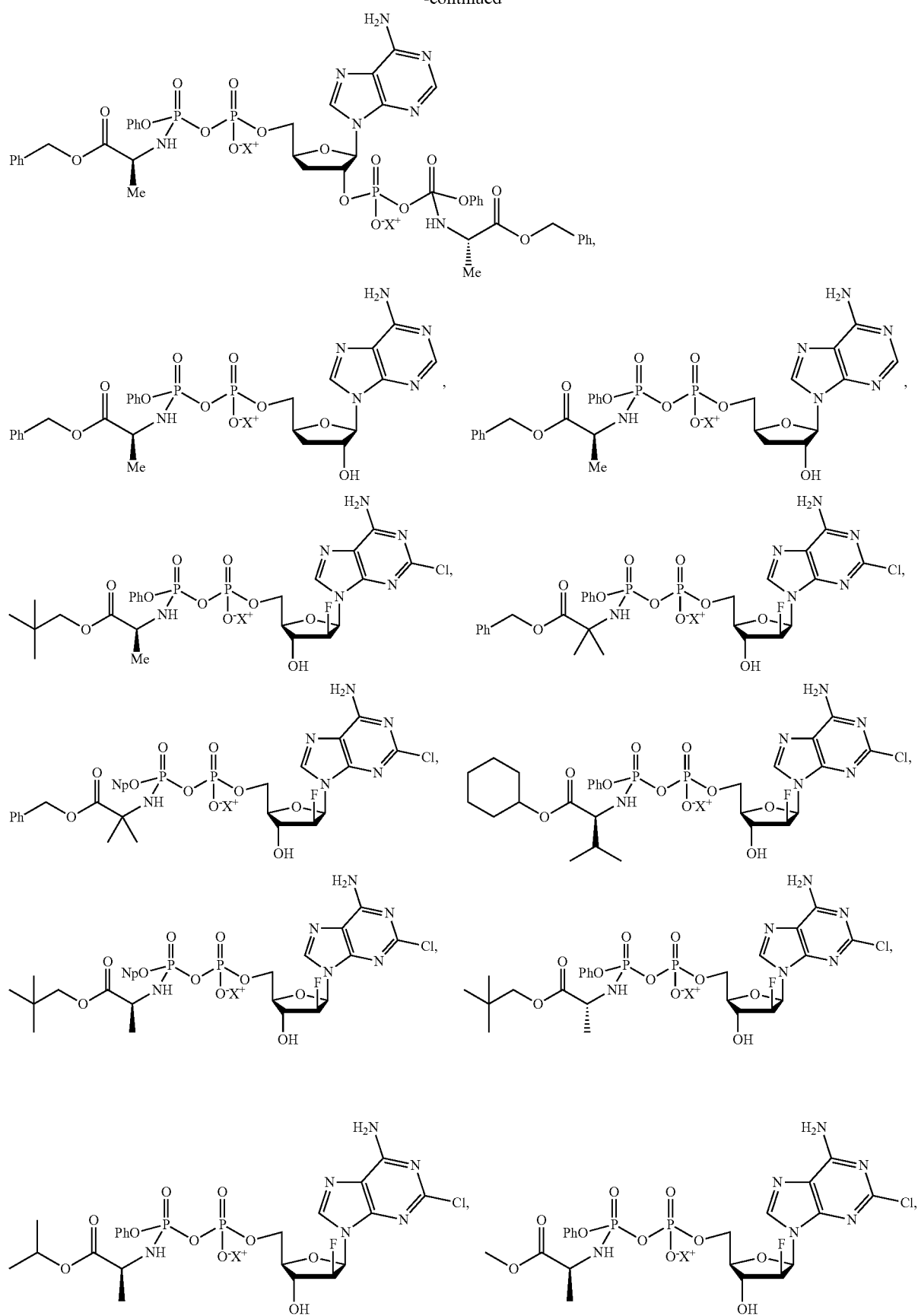

-continued

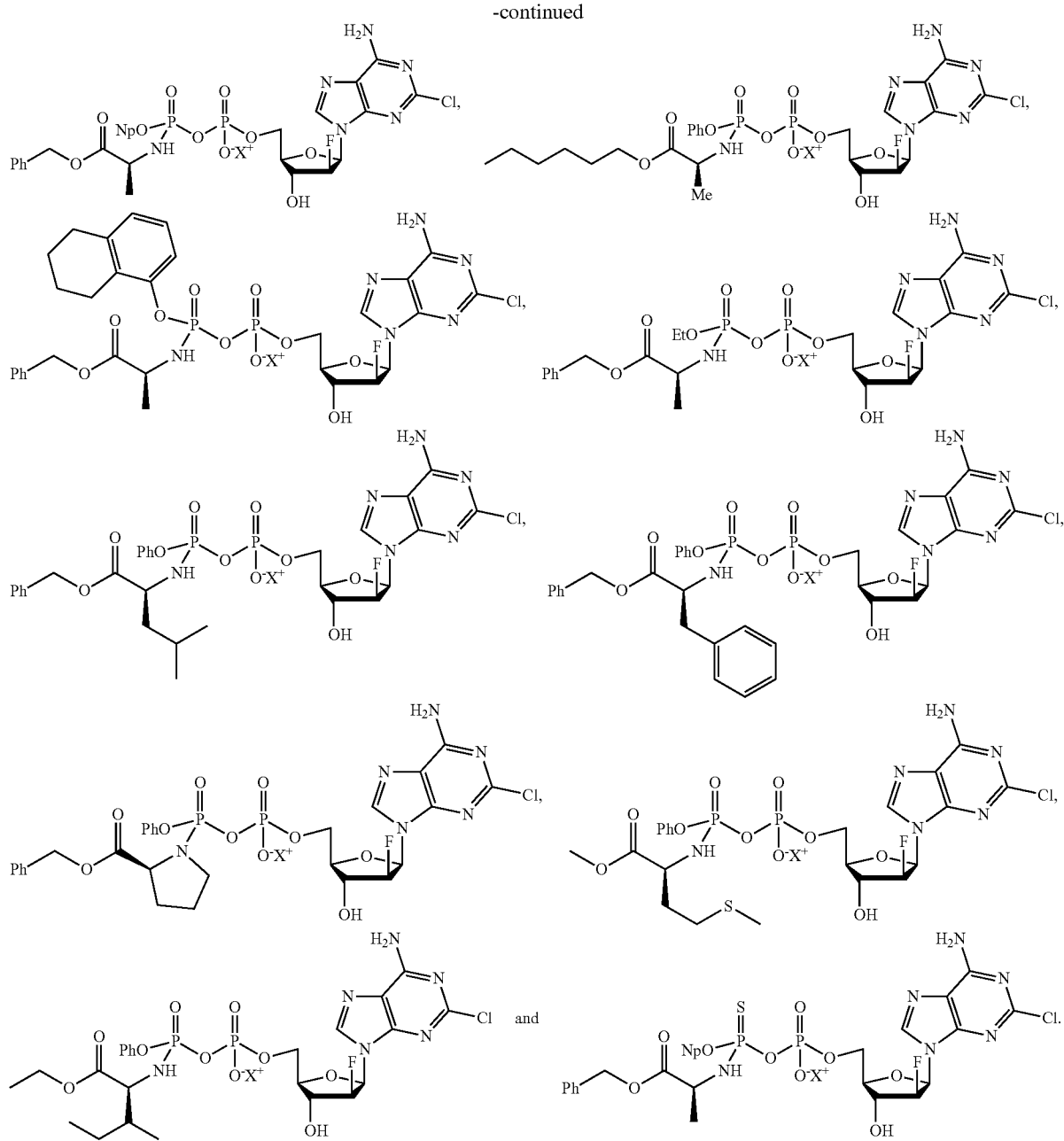

24. A method for treating cancer, comprising administering to a patient in need thereof a compound of claim 1, wherein the cancer is a leukaemia or a lymphoma.

25. The method of claim 24, wherein the cancer is a leukaemia selected from the group consisting of acute myeloid leukaemia (AML), acute lymphoid leukaemia (ALL), chronic myeloid leukaemia (CML), chronic lymphoid leukaemia (CLL) and biphenotypic acute leukaemia (BAL).

26. The method of claim 24, wherein the cancer is a lymphoma selected from the group consisting of Hodgkin's lymphoma and non-Hodgkin's lymphoma.

27. A pharmaceutical composition comprising the compound of claim 1; and at least one pharmaceutically acceptable excipient.

* * * * *